US012797458B2

(12) United States Patent
Steinmetz et al.

(10) Patent No.: US 12,797,458 B2
(45) Date of Patent: Nov. 17, 2026

(54) MODIFIED VIRAL THERAPEUTICS AND USES THEREOF

(71) Applicant: THE REGENTS OF THE UNIVERSITY OF CALIFORNIA, Oakland, CA (US)

(72) Inventors: Nicole Steinmetz, La Jolla, CA (US); Hui Cai, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1011 days.

(21) Appl. No.: 17/779,484

(22) PCT Filed: Nov. 19, 2020

(86) PCT No.: PCT/US2020/061202
§ 371 (c)(1),
(2) Date: May 24, 2022

(87) PCT Pub. No.: WO2021/108202
PCT Pub. Date: Jun. 3, 2021

(65) Prior Publication Data
US 2023/0038487 A1 Feb. 9, 2023

Related U.S. Application Data

(60) Provisional application No. 62/940,211, filed on Nov. 25, 2019.

(51) Int. Cl.
*A61K 39/12* (2006.01)
*A61K 31/7125* (2006.01)
(Continued)

(52) U.S. Cl.
CPC .......... *A61K 39/12* (2013.01); *A61K 31/7125* (2013.01); *A61K 39/39* (2013.01); *C12N 7/00* (2013.01)

(58) Field of Classification Search
None
See application file for complete search history.

(56) References Cited

U.S. PATENT DOCUMENTS 5,994,624 A 11/1999 Trolinder et al.
10,052,370 B2 8/2018 Savelyeva et al.
(Continued)

FOREIGN PATENT DOCUMENTS

WO WO-2007/053188 A2 5/2007
WO WO-2008/048288 A2 4/2008
(Continued)

OTHER PUBLICATIONS

Vollmer et al. (Immunology. 2004; 113:212-223).*
(Continued)

*Primary Examiner* — Shanon A. Foley
(74) *Attorney, Agent, or Firm* — FOLEY & LARDNER LLP

(57) ABSTRACT

Disclosed herein, in certain embodiments, are engineered virus-like particles and compositions that comprise an oligodeoxynucleotide (ODN) for the treatment of a disease or condition. In some embodiments, also disclosed herein are methods of inducing phagocytosis of a target cell and methods of immune modulation.

13 Claims, 18 Drawing Sheets

Specification includes a Sequence Listing.

(51) Int. Cl.
*A61K 39/39* (2006.01)
*C12N 7/00* (2006.01)

(56) References Cited

U.S. PATENT DOCUMENTS

| | | | | |
|---|---|---|---|---|
| 10,682,365 | B2 | 6/2020 | Krieg | |
| 2004/0219525 | A1 | 11/2004 | Haertel et al. | |
| 2005/0170336 | A1 | 8/2005 | Belcher et al. | |
| 2006/0216238 | A1 | 9/2006 | Manchester et al. | |
| 2007/0041999 | A1* | 2/2007 | Rasochova | A61P 31/12 435/235.1 |
| 2011/0296543 | A1 | 12/2011 | Chang et al. | |
| 2011/0318373 | A1 | 12/2011 | Sasikumar et al. | |
| 2012/0015899 | A1 | 1/2012 | Lomonossoff et al. | |
| 2012/0077205 | A1 | 3/2012 | Ohmiya et al. | |
| 2012/0174263 | A1 | 7/2012 | Saunders et al. | |
| 2013/0067807 | A1 | 3/2013 | Vezina et al. | |
| 2013/0330335 | A1 | 12/2013 | Bremel et al. | |
| 2014/0017239 | A1 | 1/2014 | Brown et al. | |
| 2014/0056933 | A1 | 2/2014 | Renner et al. | |
| 2014/0134202 | A1 | 5/2014 | Leclerc et al. | |
| 2015/0267196 | A1 | 9/2015 | Alsberg et al. | |
| 2016/0008397 | A1* | 1/2016 | Krams | A61K 40/418 424/278.1 |
| 2016/0194625 | A1 | 7/2016 | Hoge et al. | |
| 2017/0021003 | A1 | 1/2017 | Steinmetz et al. | |
| 2017/0211081 | A1 | 7/2017 | Hill et al. | |
| 2017/0312371 | A1 | 11/2017 | Bachmann et al. | |
| 2017/0348438 | A1 | 12/2017 | Steinmetz et al. | |
| 2018/0289789 | A1 | 10/2018 | Ali et al. | |
| 2018/0318365 | A1 | 11/2018 | Yeung et al. | |
| 2019/0030148 | A1 | 1/2019 | Steinmetz et al. | |
| 2019/0169236 | A1 | 6/2019 | Taylor | |
| 2020/0023045 | A1 | 1/2020 | Shimamura et al. | |
| 2020/0095320 | A1 | 3/2020 | Pan et al. | |
| 2020/0283738 | A1 | 9/2020 | Steinmetz et al. | |
| 2020/0392193 | A1 | 12/2020 | Inoue | |
| 2021/0060147 | A1 | 3/2021 | Steinmetz et al. | |
| 2021/0085777 | A1 | 3/2021 | Steinmetz et al. | |
| 2021/0189396 | A1 | 6/2021 | Steinmetz | |
| 2021/0254021 | A1 | 8/2021 | Csar et al. | |
| 2021/0369828 | A1 | 12/2021 | Steinmetz et al. | |
| 2022/0145316 | A1 | 5/2022 | Steinmetz et al. | |
| 2023/0038487 | A1* | 2/2023 | Steinmetz | A61K 39/12 |
| 2024/0066108 | A1 | 2/2024 | Steinmetz et al. | |
| 2024/0209325 | A1 | 6/2024 | Steinmetz et al. | |
| 2024/0261429 | A1 | 8/2024 | Steinmetz et al. | |
| 2024/0293335 | A1 | 9/2024 | Park et al. | |
| 2024/0350422 | A1 | 10/2024 | Steinmetz et al. | |
| 2025/0017991 | A1 | 1/2025 | Steinmetz et al. | |
| 2025/0127842 | A1 | 4/2025 | Steinmetz et al. | |
| 2025/0205331 | A1 | 6/2025 | Steinmetz et al. | |
| 2025/0213717 | A1 | 7/2025 | Steinmetz et al. | |
| 2025/0302975 | A1 | 10/2025 | Steinmetz et al. | |
| 2025/0325608 | A1 | 10/2025 | Steinmetz et al. | |
| 2025/0332234 | A1 | 10/2025 | Steinmetz et al. | |
| 2025/0332278 | A1 | 10/2025 | Steinmetz et al. | |

FOREIGN PATENT DOCUMENTS

| | | | |
|---|---|---|---|
| WO | WO-2009/047610 | A1 | 4/2009 |
| WO | WO-2011/149061 | A1 | 12/2011 |
| WO | WO-2015/155738 | A2 | 10/2015 |
| WO | WO-2018/107103 | A1 | 6/2018 |
| WO | WO-2018/165663 | A1 | 9/2018 |
| WO | WO-2018/208828 | A1 | 11/2018 |
| WO | WO-2018/226685 | A2 | 12/2018 |
| WO | WO-2019/195621 | A1 | 10/2019 |
| WO | WO-2020/111913 | A1 | 6/2020 |
| WO | WO-2020/180738 | A1 | 9/2020 |
| WO | WO-2021/108202 | A1 | 6/2021 |
| WO | WO-2021/211942 | A1 | 10/2021 |
| WO | WO-2022/150648 | A1 | 7/2022 |
| WO | WO-2022/150661 | A2 | 7/2022 |
| WO | WO-2022/221692 | A1 | 10/2022 |
| WO | WO-2022/266264 | A1 | 12/2022 |
| WO | WO-2023/009458 | A2 | 2/2023 |
| WO | WO-2023/034229 | A1 | 3/2023 |
| WO | WO-2023/086415 | A2 | 5/2023 |
| WO | WO-2023/183466 | A1 | 9/2023 |
| WO | WO-2023/192203 | A2 | 10/2023 |
| WO | WO-2023/200865 | A2 | 10/2023 |
| WO | WO-2023/230187 | A2 | 11/2023 |
| WO | WO-2024/026035 | A2 | 2/2024 |
| WO | WO-2024/026038 | A2 | 2/2024 |
| WO | WO-2024/054878 | A1 | 3/2024 |
| WO | WO-2024/211576 | A1 | 10/2024 |
| WO | WO-2024/233406 | | 11/2024 |
| WO | WO-2024/259377 | A2 | 12/2024 |
| WO | WO-2025/006780 | A1 | 1/2025 |
| WO | WO-2025/019513 | A2 | 1/2025 |
| WO | WO-2025/260018 | A1 | 12/2025 |

OTHER PUBLICATIONS

Jie et al. (International Journal of Molecular Sciences. Mar. 20, 2018; 19 (3): 920).*

Wang et al. (Advanced Materials. Aug. 2017; 29 (29): 1606036).*

Yildiz et al. (Journal of Controlled Release. 2013; 172: 568-578).*

Lizotte et al. (Nature nanotechnology. Mar. 2016;11 (3): 295-303).*

Hassani-Mehraban, et al., "Feasibility of Cowpea chlorotic mottle virus-like particles as scaffold for epitope presentations", BMC Biotechnology, 2015, 15:80, 17 pages.

International Search Report and Written Opinion dated Mar. 22, 2021, from application No. PCT/US2020/061202.

Lam, et al., "Delivery of siRNA therapeutics using cowpea chlorotic mottle virus-like particles", The Royal Society of Chemistry, 2019, 5 pages.

Lemke-Miltner, et al., "Antibody Opsonization of a TLR9 Agonist-Containing Virus-like Particle Enhances In Situ Immunization", The Journal of Immunology, Jan. 17, 2020, 10 pages.

Rohovie, et al., "Virus-like particles: Next-generation nanoparticles for targeted therapeutic delivery", Bioengineering & Translational Medicine, 2017, 2, pp. 43-57.

Shirota, et al., "CpG Oligonucleotides as Cancer Vaccine Adjuvants", Vaccines, 2015, 3, pp. 390-407.

Storni, et al., "Nonmethylated CG Motifs Packages into Virus-Like Particles Induce Protective Cytotoxic T Cell Responses in the Absence of Systemic Side Effects", The Journal of Immunology, 2004, 172, pp. 1777-1785.

Wang, et al., "CD47 Blockade and Cowpea Mosaic Virus Nanoparticle in situ Vaccination Synergistically Triggers Phagocytosis and Tumor Killing", 1-12 Adv. Healthc. Mater, Apr. 2019; abstract, p. 2, third paragraph; p. 4, third paragraph; p. 5, second paragraph.

Wen, et al., "Tropism of CPMV to Professional Antigen Presenting Cells Enables a Platform to Eliminate Chronic Infections", ACS Biomaterials Science & Engineering, 2015, 5 pages.

Ailincai et al., "Drug delivery systems based on biocompatible imino-chitosan hydrogels for local anticancer therapy", Drug Delivery, 2018. vol. 25, pp. 1080-1090.

Basak et al., "The encapsulation of hydrophobic drugs in Pluronic F127 micelles: the effects of drug hydrophobicity, solution temperature and pH", Lagnmuir, Mar. 2013, 23 pages.

Bayon et al., "A simple swell-and-click method for the covalent attachment of virus-like particles to polymer hydrogels" Materials Today Chemistry, 2024, vol. 38, 102100, pp. 1-10.

Bruckman et al. "Dual-Modal Magnetic Resonance and Fluorescence Imaging of Atherosclerotic Plaques in Vivo Using VCAM-1 Targeted Tobacco Mosaic Virus" Nano Letters, 2014 vol. 14, pp. 1551-1558.

Bruckman et al., Chemical Modification of the Inner and Outer Surfaces of Tobacco Mosaic Virus (TMV), in: Virus Hybrids as Nanomaterials. Methods in Molecular Biology, 2014, pp. 173-185.

Chan et al., "Biomimetic Virus-Like Particles as Severe Acute Respiratory Syndrome Coronavirus 2 Diagnostic Tools," ACS Nano, 2020, vol. 15, pp. 1259-1272.

Chan et al., "Isolation of a Peptide That Binds to Pseudomonas aeruginosa Lytic Bacteriophage," ACS Omega, 2022, vol. 7, pp. 38053-38060.

(56) References Cited

OTHER PUBLICATIONS

Chan et al., "Isolation of Cowpea Mosaic Virus-Binding Peptides," Biomacromolecules, Jul. 27, 2021, vol. 22, No. 8, pp. 3613-3623.
Chen et al., "Fusion Protein Linkers: Property, Design and Functionality," Advanced Drug Delivery Reviews, 2014, vol. 65, No. 10, pp. 1-32.
Cho et al., "Viral nanoparticles decorated with novel EGFL7 ligands enable intravital imaging of tumor neovasculature," Nanoscale, 2017, vol. 9(33), pp. 12096-12109.
Chung et al., "Development of a Modular NTA:His Tag Viral Vaccine for Co-delivery of Antigen and Adjuvent", Bioconjugate Chemistry, Jan. 6, 2023, vol. 34, pp. 269-278.
Genbank, NRPS Trichoderma atroviride, Accession: UKZ63969.I, Feb. 15, 2022.
Hodges et al., "The Many Roles of BAF (mSWI/SNF) and PBAF Complexes in Cancer," Cold Spring Harb Perspect Med, 2016, 6, a026930, 25 pages.
Hong et al., "Labeling Live Cells by Copper-Catalyzed Alkyne-Azide Click Chemistry," Bioconjug Chem. 2010, vol. 21, No. 10, pp. 1912-1916.
Horvati et al., "Surface Layer Modification of PLGA Nanoparticles with Targeting Peptide: A Convenient Synthetic Route for Pluronic F127—Tuftsin Conjugate", Bioconjug. Chem., May 2018, Abstract, 9 pages.
Hu et al., "Dysprosium-Modified Tobacco Mosaic Virus Nanoparticles for Ultra-High-Field Magnetic Resonance and Near-Infrared Fluorescence Imaging of Prostate Cancer," ACS Nano, 2017, vol. 11, pp. 9249-9258.
Hui et al., "Click-functionalized hydrogel design for mechanobiology investigations" Mol Syst Des Eng, 2021, vol. 6, pp. 670-707.
Kim et al., "Gelling hypotonic polymer solution for extended topical drug delivery to the eye", Nat Biomed Eng., Nov. 2020, 4(11), pp. 1053-1062.
Le et al., "Potato virus X, a filamentous plant viral nanoparticle for doxorubicin delivery in cancer therapy," Nanoscale 2017, vol. 9, pp. 2348-2357.
Leong et al., "Intravital imaging of embryonic and tumor neovasculature using viral nanoparticles," Nat Protoc, 2010, vol. 5, No. 8, pp. 1406-1417.
Luckanagul et al., "Porous Alginate Hydrogel Functionalized with Virus as Three-Dimensional Scaffolds for Bone Differentiation" BioMacromolecules, 2012, vol. 13, pp. 3949-3958.
Massa et al., Antitumor Activity of DNA Vaccines Based on the Human Papillomavirus-16 E7 Protein Genetically Fused to a Plant Virus Coat Protein, Human Gene Therapy, 2008, vol. 19, pp. 354-364.
Mazan-Mamczarz et al., "Role of microRNA deregulation in the pathogenesis of diffuse large B-cell lymphoma (DLBCL)," Leukemia Research, 2013, vol. 37, pp. 1420-1428.
Monroy-Borrego et al., "Three methods for inoculation of viral vectors into plants", Frontiers in Plant Science, Aug. 30, 2022, 11 pages.
Non-Final Office Action on U.S. Appl. No. 17/433,965 DTD Jan. 24, 2025.
Origene Arid2 siRNA, https://www.origene.com/catalog/rnai/sirna-oligo-duplexes/sr316272/arid2-human-sirna-oligo-duplex-locus-id-196528, retrieved Jun. 14, 2024.
Ortega-Rivera et al., "Production of cytoplasmic type citrus leprosis virus-like particles by plant molecular farming," Virology, Jan. 2023, vol. 578, pp. 7-12.
Park et al., "Site-Specific Antibody Conjugation Strategy to Functionalize Virus-Based Nanoparticles", Bioconjug Chem, May 20, 2020, 31(5), pp. 1408-1416.
Poyet et al., "A library of human gut bacterial isolates paired with longitudinal multiomics data enables mechanistic microbiome research," Nature Medicine, Sep. 2, 2019, vol. 25, No. 9, pp. 144-1452.
Shin et al., "Bioconjugation of Active Ingredients to Plant Viral Nanoparticles Is Enhances by Preincubation with a Pluronic F127 Polymer Scaffold", Applied Material & Interfaces, Dec. 2021, 15 pages.
Singla et al., "Temperature-Dependent Solubilization of the Hydrophobic Antiepileptic Drug Lamotrigine in Different Pluronic Micelles—A Spectroscopic, Heat Transfer Method Small-Angle Neutron Scattering, Dynamic Light Scattering, and in Vitro Release Study", ACS Omega, 2019, pp. 11251-11262.
Wen et al. "Design of virus-based nanomaterials for medicine, biotechnology, and energy," Chem. Soc. Rev, 2016. vol. 45, pp. 4074-4126.
Wen et al., "Interior Engineering of a Viral Nanoparticle and Its Tumor Homing Properties," Biomacromolecules 2012, vol. 13, pp. 3990-4001.
Yanai et al., "Effects of Ionic and Surfactant Agents on the Antimicrobial Activity of Polyhexamethylene Biguanide", Eye & Contact Lens, vol. 37, No. 2, Mar. 2011, pp. 85-89.
Zhao et al., "An efficient Potato virus X-based microRNA silencing in Nicotiana benthamiana," Scientific Reports, 2016, 20573, 20573, pp. 1-7.
Beiss et al., "Cowpea Mosaic Virus Outperforms Other Members of the Secoviridae as In Situ Vaccine for Cancer Immunotherapy," Molecular Pharmaceutics, May 2, 2022, vol. 19, No. 5, pp. 1573-1585 1573-1585. entire document.
Blakney et al., "An Update on Self-Amplifying mRNA Vaccine Development," Vaccines, 2021, pp. 1-26.
Chung et al., "Viral nanoparticles for drug delivery, imaging, immunotherapy, and theranostic applications", Advanced Drug Delivery Reviews, 2020, vol. 156, pp. 214-235.
Karan et al., "A replicon-based COVID-19 vaccine candidate delivered by tobacco mosaic virus-like particles" 1-10. Vaccine, 2025, pp. 1-10.
Karan et al., "A Self-Amplifying Human Papillomavirus 16 Vaccine Candidate Delivered by Tobacco Mosaic Virus-Like Particles" 1-18. ACS Appl Bio Mater. 2024, pp. 1-18.
Karan et al., "In vivo delivery of spherical and cylindrical in vitro reconstituted virus-like particles containing the same self-amplifying mRNA," Mol Pharm., 2024, pp. 1-32.
Long et al., "Species specific differences in use of ANP32 proteins by influenza A virus", eLIFE, Jun. 4, 2019, 22 pages.
Park et al., "S100A9-targeted tobacco mosaic virus nanoparticles exhibit high specificity toward atherosclerotic lesions in ApoE-/- mice", Journal of Materials Chemistry B., Feb. 13, 2019, vol. 7, No. 11, pp. 1842-1846.
Roder et al., "Small, Smaller, Nano: New Applications for Potato Virus X in Nanotechnology", Frontiers in Plant Science, Feb. 19, 2019 (Feb. 19, 2019), vol. 10: 158, pp. 1-17.
Stump et al., "Remission-Stage Ovarian Cancer Cell Vaccine with Cowpea Mosaic Virus Adjuvant Prevents Tumor Growth," Cancers, 2021, vol. 13, pp. 1-16.
Venkataraman, et al., "Plant Virus Nanoparticles for Anti-cancer Therapy," Frontiers in Bioengineering and Biotechnology, 2021, vol. 9, pp. 1-10.
Zhou et al. "HPV16 E6/E7-based mRNA vaccine is therapeutic in mice bearing aggressive HPV-positive lesions," Frontiers in Immunology, 2023, pp. 1-12.
Zhou et al., "Efficient transient expression of human GM-CSF protein in Nicotiana benthamiana using potato virus X vector" Applied Microbiology and Biotechnology, Apr. 13, 2006 (Apr. 13, 2006), vol. 72, No. 4, pp. 756-762.
Bindi Patel, Plant viral nanoparticle-based vaccine targeting NY-ESO-1+ tn'ple negative breast cancer, Master of Science Thesis, Case Western Reserve University, May 2018. (Year: 2018).
Dalakouras et al., "Delivery of Hairpin RNAs and Small RNAs Into Woody and Herbaceous Plants by Trunk Injection and Petiole Absorption," Frontiers in Plant Science, vol. 9, Article 1253, Aug. 24, 2018, pp. 1-11.
Hodge et al., "The Tipping Point for Combination Therapy: Cancer Vaccines with Radiation, Chemotherapy, or Targeted Small Molecule Inhibitors," Seminars in Oncology, vol. 39, No. 3, pp. 323-339, Jun. 2012.
International Search Report and Written Opinion for PCT/US2025/053209, dated May 28, 2026, 14 pages.
Lam et al., "Bioengineering of Tobacco Mosaic Virus to Create a Non-Infectious Positive Control for Ebola Diagnostic Assays," Scientific Reports, Mar. 31, 2016:23803, pp. 1-8.

(56) References Cited

OTHER PUBLICATIONS

Lindbo, "TRBO: A High-Efficiency Tobacco Mosaic Virus RNA-Based Overexpression Vector," Plant Physiology, vol. 145, Dec. 2007, pp. 1232-1240.
Patel et al., "Radiation therapy combined with cowpea mosaic virus nanoparticle in situ vaccination initiates immune-mediated tumor regression," ACS Omega, 3, 2018, pp. 3702-3707.
Zhang et al., "Abscopal Effects with Hypofractionated Schedules Extending into the Effector Phase of the Tumor-Specific T-Cell Response," International Journal of Radiation Oncology, vol. 101, No. 1, Jan. 2018 pp. 63-73.

* cited by examiner

MODIFIED VIRAL THERAPEUTICS AND USES THEREOF

CROSS-REFERENCE TO RELATED APPLICATIONS

This application is a U.S. National Stage Application under 35 U.S.C. § 371 of International Patent Application No. PCT/US2020/061202, filed on Nov. 19, 2020, which claims priority under 35 U.S.C. § 119(e) to U.S. Provisional Patent Application No. 62/940,211, filed Nov. 25, 2019, the contents of each of which are incorporated herein by reference in their entireties.

STATEMENT OF GOVERNMENT SUPPORT

This invention was made with government support under CA224605 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 10, 2026, is named 114198-9611_SL.txt and is 14,511 bytes in size.

INCORPORATION BY REFERENCE

All publications, patents, and patent applications mentioned in this specification and attached Appendices are herein incorporated by reference to the same extent as if each individual publication, patent, patent application or appendix, was specifically and individually indicated to be incorporated by reference.

BACKGROUND OF THE DISCLOSURE

Bacterial DNA and synthetic oligodeoxynucleotides (ODNs) containing CpG motifs exhibit immunostimulatory effects on various subsets of immune cells. These effects are caused by the presence of unmethylated CpG dinucleotides, which trigger signaling via Toll-like receptor 9 (TLR9). As such, CpG-ODNs have been used in immunotherapy in the treatment of allergy, infectious diseases, and cancer.

SUMMARY OF THE DISCLOSURE

Initial studies demonstrated the promising efficacy of CpG-ODNs in several preclinical tumor models, especially hematologic malignancies such as B cell leukemia and lymphoma. The CpG-ODNs triggered TLR9 signaling and the secretion of pro-inflammatory cytokines, inducing the activity of $CD4^+$ Th1 cells and eliciting a cytotoxic $CD8^+$ T cell response in vivo. Following these promising preclinical studies, several clinical trials explored the potential of CpG-ODNs as immunoadjuvants delivered as single agents or in combination with cancer vaccines. Although these trials failed to demonstrate sufficient antitumor efficacy, they nevertheless provided evidence that TLR9 agonists are well tolerated by cancer patients. Primary adverse effects included local immunostimulation and dose-dependent local reactions, as well as systemic influenza-like symptoms. There is also evidence that prolonged systemic treatment with CpG-ODNs causes liver and kidney toxicity, and may lead to autoimmune disorders.

The success of CpG-ODN therapy is also limited by the presence of nucleases in vivo, which reduce the half-life of ODN drugs and result in unfavorable pharmacokinetic profiles. A second barrier is the strong negative charge carried by CpG-ODNs, which inhibits their interactions with immune cells. Strategies to improve the immunomodulatory properties and efficacy of CpG ODNs include chemical modification with a phosphorothioate backbone, lipids, or G-rich DNA ligands to enhance chemical stability, and the encapsulation of ODNs using gold nanoparticles, DNA tetrahedra, or hydrogels to enhance delivery. Although these approaches can increase the preclinical efficacy of ODNs, they require complex chemical modifications, use synthetic delivery vehicles, or involve the assembly of complex DNA nanostructures.

Virus-like particles (VLPs) have been utilized as targeted delivery platforms of therapeutic nucleic acids. However, host immune response toward VLPs and manufacturing process provide challenges with the use of VLPs as a delivery platform on a large scale. Therefore, there is a need for alternative delivery platforms for targeted immunotherapy comprising, or consisting essentially of, or yet further consisting of CpG-ODNs.

Building on these discoveries, Applicant provides herein, in certain embodiments, engineered virus-like particles, compositions (e.g., pharmaceutical compositions), and lyophilized formulations that comprise, or consist essentially of, or yet further consist of, a therapeutically-efficacious short nucleic acids for the treatment of a disease or condition or an immune response. In some instances, the therapeutically-efficacious short nucleic acids are utilized for immunostimulation. In some embodiments, the therapeutically-efficacious short nucleic acids are or comprise an oligodeoxynucleotide (ODN).

In certain embodiments, disclosed herein is an engineered virus-like particle (VLP) comprising, or consisting essentially of, or yet further consisting of, an oligodeoxynucleotide (ODN) with less than 100 nucleotides encapsulated within the VLP, the ODN being optionally resistant to nuclease digestion. In some embodiments, also disclosed herein is a composition (e.g., a pharmaceutical composition) comprising, or consisting essentially of, or yet further consisting of, an engineered VLP comprising, or consisting essentially of, or yet further consisting of, an oligodeoxynucleotide (ODN) with less than 100 nucleotides encapsulated within the VLP, the ODN being optionally resistant to nuclease digestion, and a carrier. A non-limiting example of a carrier comprises a pharmaceutically acceptable carrier.

In some embodiments, also disclosed herein are methods of inducing phagocytosis of a target cell and methods of immune modulation. In an exemplary instances disclosed herein, Applicant discloses a method of treating a disease or condition or inducing an immune response in a subject in need thereof, the method comprising, or consisting essentially of, or yet further consisting of, administering to the subject an engineered virus-like particle (VLP) that comprises, or consists essentially of, or yet further consists of, an oligodeoxynucleotide (ODN) with less than 100 nucleotides encapsulated within the VLP, the ODN being optionally resistant to nuclease digestion or a composition comprising, or consisting essentially of, or yet further consisting of, an engineered VLP comprising, or consisting essentially of, or yet further consisting of, an oligodeoxynucleotide (ODN) with less than 100 nucleotides encapsulated within the VLP, the ODN being optionally resistant to nuclease digestion, and a carrier, such as for example, a pharmaceutically acceptable carrier.

In some embodiments, also disclosed herein is a method of modulating phagocytosis in a target cell, the method comprising, or consisting essentially of, or yet further consisting of, contacting the target cell or a plurality of target cells comprising, or consisting essentially of, or yet further consisting of, a macrophage with an engineered VLP comprising, or consisting essentially of, or yet further consisting of, an oligodeoxynucleotide (ODN) with less than 100 nucleotides encapsulated within the VLP, the ODN being optionally resistant to nuclease digestion or a composition comprising, or consisting essentially of, or yet further consisting of, an engineered VLP comprising, or consisting essentially of, or yet further consisting of, an oligodeoxynucleotide (ODN) with less than 100 nucleotides encapsulated within the VLP, the ODN being optionally resistant to nuclease digestion, and a carrier, that is optionally a pharmaceutically acceptable carrier for a first time sufficient to activate phagocytic activity of the macrophage; and contacting the activated macrophage with the target cell or population for a second time sufficient to induce phagocytosis of the target cell.

In additional embodiments, disclosed herein is a method of modulating M1 macrophage polarization, the method comprising, or consisting essentially of, or yet further consisting of, contacting a plurality of antigen presenting cells (APCs) that comprise, or consist essentially of, or yet further consist of, at least one macrophage with an engineered VLP comprising, or consisting essentially of, or yet further consisting of, an oligodeoxynucleotide (ODN) with less than 100 nucleotides encapsulated within the VLP, the ODN being optionally resistant to nuclease digestion or a composition comprising, or consisting essentially of, or yet further consisting of, an engineered VLP comprising, or consisting essentially of, or yet further consisting of, an oligodeoxynucleotide (ODN) with less than 100 nucleotides encapsulated within the VLP, the ODN being optionally resistant to nuclease digestion, and a carrier, optionally a pharmaceutically acceptable carrier for a time sufficient to induce secretion of a plurality of cytokines by the plurality of APCs, whereby the secretion of the plurality of cytokines modulate M1 activation of the macrophage.

In further embodiments, disclosed herein is a kit comprising, or consisting essentially of, or yet further consisting of, an engineered VLP comprising, or consisting essentially of, or yet further consisting of, an oligodeoxynucleotide (ODN) with less than 100 nucleotides encapsulated within the VLP, the ODN being optionally resistant to nuclease digestion or a composition comprising, or consisting essentially of, or yet further consisting of, an engineered VLP comprising, or consisting essentially of, or yet further consisting of, an oligodeoxynucleotide (ODN) with less than 100 nucleotides encapsulated within the VLP that is optionally resistant to nuclease digestion, and a carrier, and further optionally a pharmaceutically acceptable carrier, and optionally instructions for use.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A illustrates a schematic diagram of CCMV disassembly and reassembly. FIG. 1B shows an analysis of CCMV, eCCMV and CCMV-ODN1826 by UV-Vis absorbance spectrophotometry. FIG. 1C shows an analysis of CCMV, CCMV-ODN1826 and ODN1826 by native agarose gel electrophoresis. FIG. 1D shows an analysis of CCMV and CCMV-ODN1826 by size-exclusion chromatography (SEC). FIG. 1E shows an analysis of CCMV and CCMV-ODN1826 by dynamic light scattering (DLS). FIG. 1F shows an analysis of negatively stained CCMV and CCMV-ODN1826 by transmission electron microscopy (TEM). Scale bar=100 nm.

FIG. 2A shows the stability of CCMV and CCMV-ODN1826 under in vitro physiological conditions (PBS, pH 7.4) over time (0, 4 and 10 days). FIG. 2B shows the stability of CCMV-ODN1826 in PBS containing 5 U $mL^{-1}$ DNase.

FIG. 3A illustrates a gating strategy for the analysis of macrophages and tumor cells. TAMs were gated as CD45+CD11b$^+$ F4/80$^+$ cells, and tumor cells were gated as CD45$^-$ cells. FIG. 3B shows percentage of CY5$^+$ cells, confirming the uptake of ODN1826 or CCMV-ODN1826. FIG. 3C shows fold-change in the percentage of CY5$^+$ cells following incubation with CCMV-ODN1826 compared to free ON1826. FIG. 3D shows mean fluorescence intensity (MFICY5) of tumor cells and TAMs. FIG. 3E shows fold-change in the MFI following incubation with CCMV-ODN1826 compared to free ON1826. Values are means±stand deviations (n=3). Statistical significance was determined using a two-tailed Student's t-test: *p<0.05, p<0.01, *p<0.001, ****p<0.0001.

FIG. 4A shows in vitro phagocytosis of CFSE-labeled CT26 tumor cells by BMDMs stimulated with free ODN1826, CCMV-ODN1826 or control VLPs (eCCMV, CCMV, or CCMV-ODN2138). BMDMs were gated as F4/80$^+$ cells. FIG. 4B shows CT26-luc cell survival following coculture with BMDMs for 48 h in the presence of ODN1826 or the VLPs listed above. FIG. 4C shows the iNOS/Arg ratio of BMDMs following stimulation with ODN1826 or the VLPs listed above, with LPS and IL-4 as controls for M1 and M2 polarization, respectively. Values are means±standard deviations (n=3). Statistical significance was determined by one-way ANOVA with Tukey's test: *p<0.05, p<0.01, *p<0.001.

FIG. 6A illustrates an exemplary treatment schedule. FIG. 6B shows growth curves of CT26 tumors, showing mean tumor volumes±standard deviations (n=8-10). Statistical significance was determined by two-way ANOVA (***p<0.001). FIG. 6C shows tumor growth kinetics for each treatment group.

FIG. 6D shows survival curves. Statistical significance was determined using the long-rank (Mantel-Cox) test (*p<0.05). FIG. 6E shows CT26-luc cell survival following co-culture for 48 h with TAMs in the presence of free ODN1826 or VLPs. FIG. 6F shows the iNOS/Arg ratio in TAMs of CT26 tumors after treatment with ODN1826 or VLPs. Values are means±standard deviations (n=3-4). Statistical significance was determined by one-way ANOVA with Tukey's test (ns=not significant, *p<0.05, p<0.01, *p<0.001).

FIG. 7A shows an exemplary treatment schedule. FIG. 7B shows growth curves of melanoma tumors, showing mean tumor volumes±standard deviations (n=8-10). Statistical significance was determined by two-way ANOVA (*p<0.001). FIG. 7C shows tumor growth kinetics for each treatment group. FIG. 7D shows survival curves. Statistical significance was determined using the long-rank (Mantel-Cox) test (*p<0.001).

DETAILED DESCRIPTION OF THE DISCLOSURE

Definitions

Figure 1A:
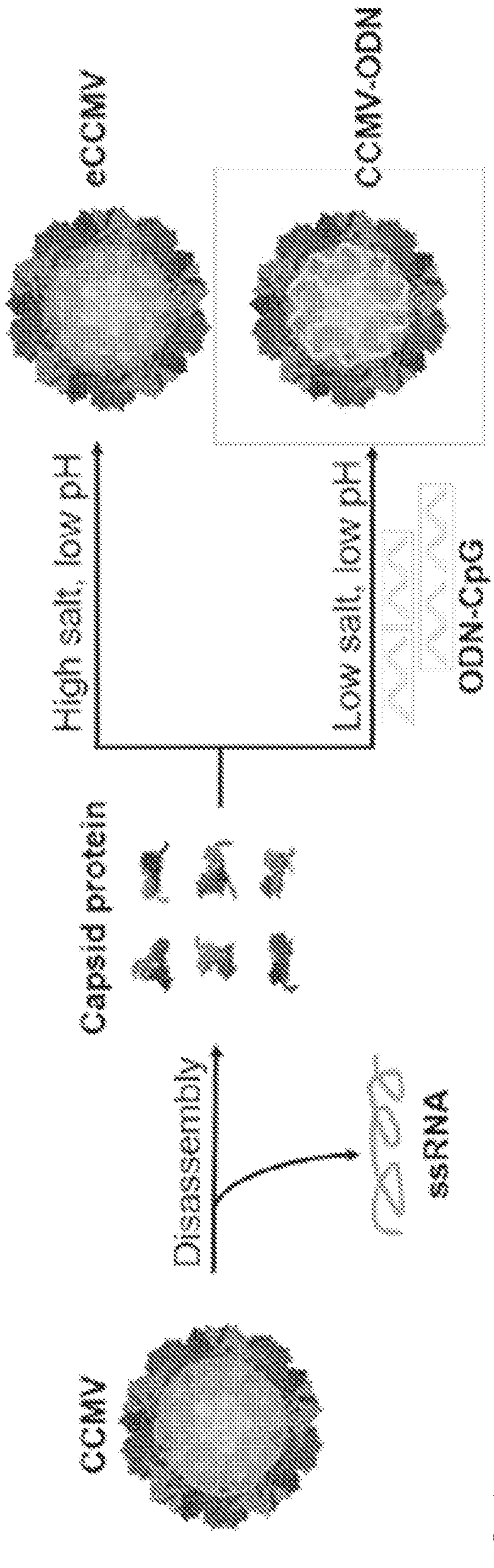
FIGS. 1A-1F illustrate preparation and characterization of CCMV-derived VLPs containing ODNs.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

As used herein, the term "comprising" is intended to mean that the methods include the recited steps or elements, but do not exclude others. "Consisting essentially of" shall mean rendering the claims open only for the inclusion of steps or elements, which do not materially affect the basic and novel characteristics of the claimed methods. "Consisting of" shall mean excluding any element or step not specified in the claim. Embodiments defined by each of these transition terms are within the scope of this disclosure.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the terms "treating," "treatment" and the like mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder. In one aspect, the term "treatment" excludes prophylaxis.

As used herein, to "treat" further includes systemic amelioration of the symptoms associated with the pathology and/or a delay in onset of symptoms. Clinical and subclinical evidence of "treatment" will vary with the pathology, the individual and the treatment. In one aspect, treatment excludes prophylaxis.

The term "ameliorate" means a detectable improvement in a subject's condition. A detectable improvement includes a subjective or objective decrease, reduction, inhibition, suppression, limit or control in the occurrence, frequency, severity, progression, or duration of a symptom caused by or associated with a disease or condition, such as one or more adverse symptoms, disorders, illnesses, pathologies, diseases, or complications caused by or associated with the disease or condition, or an improvement in an underlying cause or a consequence of the disease or condition, or a reversal of the disease or condition.

Treatment can therefore result in decreasing, reducing, inhibiting, suppressing, limiting, controlling or preventing a disease or condition, or an associated symptom or consequence, or underlying cause; decreasing, reducing, inhibiting, suppressing, limiting, controlling or preventing a progression or worsening of a disease, condition, symptom or consequence, or underlying cause; or further deterioration or occurrence of one or more additional symptoms of the disease condition, or symptom. Thus, a successful treatment outcome leads to a "therapeutic effect," or "benefit" of decreasing, reducing, inhibiting, suppressing, limiting, controlling or preventing the occurrence, frequency, severity, progression, or duration of one or more symptoms or underlying causes or consequences of a condition, disease or symptom in the subject, such as one or more adverse symptoms, disorders, illnesses, pathologies, diseases, or complications caused by or associated with a disease or condition. Treatment methods affecting one or more underlying causes of the condition, disease or symptom are therefore considered to be beneficial. Stabilizing a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial decrease, reduction, inhibition, suppression, limit, control or prevention in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, such as one or more adverse symptoms, disorders, illnesses, pathologies, diseases, or complications caused by or associated with the disease or condition, over a short or long duration of time (hours, days, weeks, months, etc.). In one aspect, prophylaxis or prevention is excluded from "treatment" or "therapeutic benefit."

As used herein, the disease or condition comprise, or consists essentially of, or yet further consists of, a cancer, e.g., a solid tumor or a hematologic malignancy. Exemplary solid tumors include, but are not limited to, bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, prostate cancer, or stomach cancer. Exemplary hematologic malignancy include, but are not limited to, chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Engineered Virus-Like Particles

In some embodiments, Toll-like-receptor 9 (TLR9), one of the TLR family members, recognizes unmethylated CpG motifs in pathogenic DNA leading to activation of immune cells. Oligodeoxynucleotide (ODN) comprising, or consisting essentially of, or yet further consisting of, unmethylated CpG motifs can mimick the effect of unmethylated CpG motifs of pathogenic DNA, thereby inducing activation of immune cells. In some instances, the ODN comprise, or consists essentially of, or yet further consists of, a nucleic acid molecule comprising, or consisting essentially of, or yet further consisting of, at least on CpG motif. In some instances, the ODN is a CpG-containing ODN (CpG ODN). In some instances, the CpG ODN is a Class A, Class B, Class C, Class P, or Class S ODN. In some instances, the CpG ODN is a Class A (Type D) ODN. Class A ODNs stimulate the production of Type I interferons, e.g., IFNα, induce maturation of plasmacytoid dendritic cells (pDCs), and indirectly activate NK cells via IFNα secretion.

In some instances, the CpG ODN is a Class B (Type K) ODN. Class B ODNs stimulate B cells and monocyte maturation and activates NK cells. In some instances, Class B ODNs also induce maturation of pDC but to a lesser extent than Class A ODNs.

In some instances, the CpG ODN is a Class C ODN. Class C ODNs stimulates pDC IFNα production, antigen-presenting cell (APC) activation and maturation, indirect NK cell activation, and direct B-cell stimulation.

In some instances, the CpG ODN is selected from Class P ODN or Class S ODN. In some instances, the CpG ODN is a Class P ODN. Class P ODNs induce IFNα production and stimulates B-cell activation. In some instances, the CpG ODN is a Class S ODN.

In some instances, the ODN is from about 15 nucleotides to about 30 nucleotides, from about 15 nucleotides to about 28 nucleotides, from about 15 nucleotides to about 25 nucleotides, from about 15 nucleotides to about 20 nucleotides, from about 18 nucleotides to about 30 nucleotides, from about 18 nucleotides to about 28 nucleotides, from about 18 nucleotides to about 25 nucleotides, from about 18 nucleotides to about 20 nucleotides, from about 20 nucleotides to about 30 nucleotides, from about 20 nucleotides to about 28 nucleotides, or from about 20 nucleotides to about 25 nucleotides in length.

In some cases, the ODN is less than or about 30 nucleotides. In some cases, the ODN is less than or about 29 nucleotides. In some cases, the ODN is less than or about 28 nucleotides. In some cases, the ODN is less than or about 27 nucleotides. In some cases, the ODN is less than or about 26 nucleotides. In some cases, the ODN is less than or about 25 nucleotides. In some cases, the ODN is less than or about 24 nucleotides. In some cases, the ODN is less than or about 23 nucleotides. In some cases, the ODN is less than or about 22 nucleotides. In some cases, the ODN is less than or about 21 nucleotides. In some cases, the ODN is less than or about 20 nucleotides. In some cases, the ODN is less than or about 19 nucleotides. In some cases, the ODN is less than or about 18 nucleotides. In some cases, the ODN is less than or about 17 nucleotides. In some cases, the ODN is less than or about 16 nucleotides. In some cases, the ODN is less than or about 15 nucleotides.

In some cases, the ODN is at least 10 nucleotides but no more than 100, 99, 95, or 90 nucleotides. In some cases, the ODN is at least 15 nucleotides. In some cases, the ODN is at least 18 nucleotides. In some cases, the ODN is at least 20 nucleotides. In some cases, the ODN is at least 23 nucleotides. In some cases, the ODN is at least 25 nucleotides. In some cases, the ODN is at least 28 nucleotides. In some cases, the ODN is at least 30 nucleotides. In some cases, the ODN is at least 35 nucleotides. In some cases, the ODN is at least 40 nucleotides. In some cases, the ODN is at least 50 nucleotides. In some cases, the ODN is at least 60 nucleotides. In some cases, the ODN is at least 70 nucleotides. In some cases, the ODN is at least 80 nucleotides.

In some embodiments, the oligodeoxynucleotide (ODN) comprises an ODN illustrated in Table 1 or an equivalent thereof. Note: Bases shown in capital letters are phosphodiester, and those in lower case are phosphorothioate (nuclease resistant). Palindrome is underlined and the center of the palindrome is indicated by ":".

| ODN | Sequence (5'-3') | Class | SEQ ID NO: |
|---|---|---|---|
| ODN1585 | ggGGTCAACGTTGAgggggg | A | 1 |
| ODN2216 | ggGGGACGA:TCGTCgggggg | A | 2 |
| ODN2336 | gggGACGAC:GTCGTGgggggg | A | 3 |
| ODN1826 | tccatgacgttcctgacgtt | B | 4 |
| ODN1668 | tccatgacgttcctgatgct | B | 5 |
| ODN2006 | tcgtcgttttgtcgttttgtcgtt | B | 6 |
| ODN2007 | tcgtcgttgtcgttttgtcgtt | B | 7 |
| ODN2142 | tcgcgtgcgttttgtcgttttgacgtt | B | 8 |
| ODN BW006 | tcgacgttcgtcgttcgtcgttc | B | 9 |
| ODN D-SL01 | tcgcgacgttcgcccgacgttcggta | B | 10 |
| ODN2395 | tcgtcgttttcggcgc:gcgccg | C | 11 |

-continued

| ODN | Sequence (5'-3') | Class | SEQ ID NO: |
|---|---|---|---|
| ODN M362 | tcgtcgtcgttc:gaacgacgttgat | C | 12 |
| ODN D-SL03 | tcgcgaacgttcgccgcgttcgaacgcgg | C | 13 |
| ODN10101 | TCGTCGTTTTCGCGCGCGCGCCG | C | 14 |
| ODN21798 | TCGTC:GACGATCGGCGC:GCGCCG | P | 15 |

In some embodiments, the oligodeoxynucleotide (ODN) comprises an ODN illustrated in Table 2 or an equivalent thereof.

| ODN | Therapeutic application | Class |
|---|---|---|
| ODN1585 | Cancer immunotherapy (melanoma), vaccine adjuvant, | A |
| ODN2216 | Inhibit tumor growth (pancreatic cancer), vaccine adjuvant | A |
| ODN2336 | Vaccine adjuvant | A |
| ODN1826 | Asthma, Inflammation, Allergic Rhinosinusitis, Cancer immunotherapy, Hepatitis B, vaccine adjuvant | B |
| ODN1668 | Infection prevention (*vibrio parahaemolyticus*, rock bream iridovirus), vaccine adjuvant | B |
| ODN2006 | | B |
| ODN2007 | Infectious prevention: *Edwardsiella tarda* infection in olive flounder (*Paralichthys olivaceus*), Zebrafish against *Vibrio vulnificus*-induced infectious | B |
| ODN2142 | Allergic asthma | |
| ODN BW006 | | B |
| ODN D-SL01 | | B |
| ODN2395 | Inflammatory, autoimmune diseases | C |
| ODN M362 | | C |
| ODN D-SL03 | | C |
| ODN10101 | Hepatitis C | C |
| ODN21798 | | P |

As used herein, the term "an equivalent thereof" in reference to an ODN include an ODN that comprises at least 80%, 90%, 95%, 96%, 97%, 98%, or 99% sequence identify to the respective ODN of which it is compared to, while still retaining a functional activity. In some instances, a functional activity refers to the modulation of an immunostimulatory effect on an immune cell. In some instances, the immunostimulatory effect comprise, or consists essentially of, or yet further consists of, s activation of phagocytosis of the immune cell, secretion of inflammatory cytokines, triggers TLR9 signaling, activation of $CD4^+$ Th1 cells, or eliciting a cytotoxic CD8+ T cell response.

In some embodiments, an ODN described herein comprise, or consists essentially of, or yet further consists of, one or more modified nucleotides. In some embodiments, the modified ODN comprise, or consists essentially of, or yet further consists of, a nucleotide analogue. Exemplary nucleotide analogues include, but are not limited to, morpholino, a peptide nucleic acid (PNA), a methylphosphonate nucleotide, a thiolphosphonate nucleotide, a 2'-fluoro N3-P5'-phosphoramidite, or a 1',5'-anhydrohexitol nucleic acid (THNA).

Exemplary nucleotide analogues can also include a modified base, such as, but not limited to, 5-propynyluridine, 5-propynylcytidine, 6-methyl adenine, 6-methylguanine, N,N,-dimethyl adenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O- and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some instances, the modified ODN has an increased stability relative to an ODN that is not modified.

As utilized herein, an engineered VLP is a non-native VLP that comprise, or consists essentially of, or yet further consists of, one or more viral particles, e.g., a capsid, derived from a plant virus. In some instances, the plant virus is from the genus *Bromovirus, Comovirus, Tymovirus*, or *Sobemovirus*. In some cases, the VLP is derived from Cowpea chlorotic mottle virus (CCMV), Cowpea mosaic virus (CPMV), Physalis mottle virus (PhMV), or Sesbania mosaic virus (SeMV).

In some instances, the engineered VLP comprise, or consists essentially of, or yet further consists of, a capsid protein derived from a plant virus. In some instances, the capsid protein is a wild-type protein derived from the plant virus. In other instances, the capsid protein is a variant of the wild-type protein derived from the plant virus. In additional instances, the capsid protein is a modified protein, either full-length or truncated version.

As used herein, the term "Virus-like particle" or "VLP" refers to a non-replicating, viral shell, derived from one or more viruses (e.g., one or more plant viruses described herein). VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. VLPs can also be engineered, e.g., comprising, or consisting essentially of, or yet further consisting of, one or more viral proteins that comprise, or consists essentially of, or yet further consists of, a modification. Methods for producing VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) Biophys. J. 60:1445-1456; and Hagensee et al. (1994) J. Viral. 68:4503-4505; Vincente, J Invertebr Pathol., 2011; Schneider Ohrum and Ross, Curr. Top. Microbial. Immunol., 354: 53073, 2012).

In some embodiments, the engineered VLP is derived from Cowpea chlorotic mottle virus (CCMV). CCMV is a spherical plant virus that belongs to the Bromovirus genus. Several strains have been identified and include, but not limited to, Car1 (Ali, et al., 2007. *J. Virological Methods* 141:84-86), Car2 (Ali, et al., 2007. *J. Virological Methods* 141:84-86, 2007), type T (Kuhn, 1964. *Phytopathology* 54:1441-1442), soybean (S) (Kuhn, 1968. *Phytopathology* 58:1441-1442), mild (M) (Kuhn, 1979. *Phytopathology* 69:621-624), Arkansas (A) (Fulton, et al., 1975. *Phytopathology* 65: 741-742), bean yellow stipple (BYS) (Fulton, et al., 1975. *Phytopathology* 65: 741-742), R (Sinclair, ed. 1982. Compendium of Soybean Diseases. 2nd ed. The American Phytopathological Society, St. Paul. 104 pp.), and PSM (Paguio, et al., 1988. *Plant Diseases* 72(9): 768-770).

In some instances, the engineered VLP from CCMV comprise, or consists essentially of, or yet further consists of, a plurality of capsid proteins. In some instances, the capsid protein is a wild-type CCMV capsid, optionally expressed by Car1, Car2, type T, soybean (S), mild (M), Arkansas (A), bean yellow stipple (BYS), R, or PSM strain. In other instances, the capsid protein is a modified capsid protein, e.g., comprising, or consisting essentially of, or yet further consisting of, one or more substitutions, insertions, and/or deletions. In some cases, the CCMV capsid comprise, or consists essentially of, or yet further consists of, s the sequence as set forth in the UniProtKB ID P03601:

MSTVGTGKLTRAQRRAAARKNKRN-TRVVQPVIVEPIASGQGKAIKAWTGYSV SKW-TASCAAAEAKVTSAITISLP-NELSSERNKQLKVGRVLLWLGLLPSVSGTVKSC-VTE TQTTAAASFQVALA-VADNSKDVVAAMYPEAFKGITLEQLTADLTIY-LYSSAALTEGDVI VHLEVEHVRPTFDDSFTPVY (SEQ ID NO: 16), or an equivalent thereof.

In some cases, the engineered VLP from CCMV is prepared by the method as described in Ali et al., "Rapid and efficient purification of Cowpea chlorotic mottle virus by sucrose cushion ultracentrifugation," *Journal of Virological Methods* 141: 84-86 (2007).

In some embodiments, the engineered VLP is derived from Cowpea mosaic virus (CPMV). CPMV is a non-enveloped plant virus that belongs to the Comovirus genus. CPMV strains include, but are not limited to, SB (Agrawal, H. O. (1964). *Meded. Landb. Hoogesch. Wagen.* 64:1) and Vu (Agrawal, H. O. (1964). *Meded. Landb. Hoogesch. Wagen.* 64:1).

In some instances, the engineered VLP from CPMV comprise, or consists essentially of, or yet further consists of, a plurality of capsid proteins. In some instances, CPMV produces a large capsid protein and a small capsid protein precursor (which generates a mature small capsid protein). In some cases, CPMV capsid is formed from a plurality of large capsid proteins and mature small capsid proteins. In some cases, the large capsid protein is a wild-type large capsid protein, optionally expressed by SB or Vu strain. In other instances, the large capsid protein is a modified large capsid protein, e.g., comprising, or consisting essentially of, or yet further consisting of, one or more substitutions, insertions, and/or deletions. In some cases, the large capsid protein comprise, or consists essentially of, or yet further consists of, the sequence as set forth in the UniProtKB ID P03599 (residues 460-833):

MEQNLFALSLDDTSSVRGSLLDTKFAQTRVLL-SKAMAGGDVLLDEYLYDVVN GQD-FRATVAFLRTHVITGKIKVTATTNISDNSGCCLM-LAINSGVRGKYSTDVYTICSQDS MTWNPGCKKNFSFTFNPNPCGDSWSAEMIS-RSRVRMTVICVSGWTLSPTTDVIAKLDW SIVNEKCEP-TIYHLADCQNWLPLNRWMGKLTFPQGVT-SEVRRMPLSIGGGAGATQAFL ANMPN-SWISMWRYFRGELHFEVTKMSSPYIKATVTFLI-AFGNLSDAFGFYESFPHRIVQF AEVEEKCTLVFSQQEFVTAWSTQVNPRTTLEAD-GCPYLYAIIHDSTTGTISGDFNLGVKL VGIKDFC-GIGSNPGIDGSRLLGAIAQ (SEQ ID NO: 17), or an equivalent thereof.

In some cases, the mature small capsid protein is a wild-type mature small capsid protein, optionally expressed by SB or Vu strain. In other instances, the mature small capsid protein is a modified mature small capsid protein, e.g., comprising, or consisting essentially of, or yet further consisting of, one or more substitutions, insertions, and/or deletions. In some cases, the mature small capsid protein comprise, or consists essentially of, or yet further consists of, s the sequence as set forth in the UniProtKB ID P03599 (residues 834-1022):

GPVCAEASDVYSPCMIASTP-PAPFSDVTAVTFDLINGKITPVGDDNWNTHIYNP PIMNVLRTAAWKSGTIHVQLNVR-GAGVKRADWDGQVFVYLRQSMNPESYDARTF-VIS QPGSAMLNFSFDIIGPNSGFEFAESP-WANQTTWYLECVATNPRQIQQFEVNMRFDPNFR VAGNILMPPFPLSTETPPL (SEQ ID NO: 18), or an equivalent thereof.

In some embodiments, the engineered VLP is derived from Physalis mottle virus (PhMV). PhMV is a single stranded RNA virus that belongs to the genus Tymovirus. In some instances, the engineered VLP from PhMV comprises, or consists essentially of, or yet further consists of, a plurality of coat proteins. In some instances, the coat protein is a wild-type PhMV coat protein. In other instances, the coat protein is a modified coat protein, e.g., comprising, or consisting essentially of, or yet further consisting of, one or more substitutions, insertions, and/or deletions. In some cases, the PhMV coat comprise, or consists essentially of, or yet further consists of, s the sequence as set forth in the UniProtKB ID P36351:

MDSSEVVKVKQASIPAPGSILSQPNTEQ-SPAIVLPFQFEATTFGTAETAAQVSLQ TADPITKLTAPYRHAQIVECKAILTPTDLAVSN-PLTVYLAWVPANSPATPTQILRVYGGQ SFVLG-GAISAAKTIEVPLNLDSVNRMLKDSVTYTDTPK-LLAYSRAPTNPSKIPTASIQISG RIRLSKPMLIAN (SEQ ID NO: 19), or an equivalent thereof.

In some embodiments, the engineered VLP is derived from Sesbania mosaic virus (SeMV). SeMV is a positive stranded RNA virus that belongs to the genus Sobemovirus. In some instances, the engineered VLP from SeMV comprise, or consists essentially of, or yet further consists of, s a plurality of capsid proteins. In some instances, the capsid protein is a wild-type SeMV capsid protein. In other instances, the capsid protein is a modified capsid protein, e.g., comprising, or consisting essentially of, or yet further consisting of, one or more substitutions, insertions, and/or deletions. In some cases, the SeMV capsid comprise, or consists essentially of, or yet further consists of, s the sequence as set forth in the UniProtKB ID Q9EB06:

MAKRLSKQQLAKAIANTLETPPQPK-AGRRRNRRRQRSAVQQLQPTQAGISMA PSAQGAMVRIRNPAVSSSRGGITVLTHSEL-SAEIGVTDSIVVSSELVMPYTVGTWLRGVA ANWSKYSWLSVRYTYIP-SCPSSTAGSIHMGFQYDMADTVPVSVNQLSNLR-GYVSGQV WSGSAGLCFINGTRCSDTSTAIST-TLDVSKLGKKWYPYKTSADYATAVGVDVNIAT-PLV PARLVIALLDGSSSTAVAAGRIYCTY-TIQMIEPTASALNN (SEQ ID NO: 20), or an equivalent thereof.

As used herein, the term "an equivalent thereof" in reference to a polynucleotide or a protein (e.g., a capsid or coat protein) include a polynucleotide or a protein that comprise, or consists essentially of, or yet further consists of, at least 80%, 85%, 90%, 95%, 96%, 97%, 98%, or 99% sequence identify to the respective polynucleotide or protein of which it is compared to, while still retaining a functional activity. In the instances with reference to a capsid or coat protein, a functional activity refers to the formation of a VLP.

As used herein, the term "modification" include, for example, substitutions, additions, insertions and deletions to the amino acid sequences, which can be referred to as "variants." Exemplary sequence substitutions, additions, and insertions include a full length or a portion of a sequence with one or more amino acids substituted (or mutated), added, or inserted, for example of a capsid derived from the plant virus. In some instances, a capsid described herein includes, e.g., a modified capsid comprising, or consisting essentially of, or yet further consisting of, at least 70%, 80%, 85%, 90%, 95%, 96%, 97%, 98%, 99%, or 100% sequence identity to its respective wild-type version.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared. A polynucleotide or polynucleotide region (or a polypeptide or polypeptide region) having a certain percentage (for example, 60%, 65%, 70%, 75%, 80%, 85%, 90%, 95%, 98% or 99%) of "sequence identity" to a reference sequence means that, when aligned, that percentage of bases (or amino acids) at each position in the test sequence are identical to the base (or amino acid) at the same position in the reference sequence. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLAST-N and BLASTP, using the following default parameters: Genetic code=standard; filter=none; strand==both; cutoff==60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nim.nih.gov/blast/Blast.cgi.

Modified capsid polypeptides include, for example, non-conservative and conservative substitutions of the capsid amino acid sequences.

As used herein, the term "conservative substitution" denotes the replacement of an amino acid residue by another, chemically or biologically similar residue. Biologically similar means that the substitution does not destroy a biological activity or function, e.g., assembly of a viral capsid.

Structurally similar means that the amino acids have side chains with similar length, such as alanine, glycine and serine, or a similar size. Chemical similarity means that the residues have the same charge or are both hydrophilic or hydrophobic. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. The term "conservative substitution" also includes the use of a substituted amino acid in place of an unsubstituted parent amino acid. Such proteins that include amino acid substitutions can be encoded by a nucleic acid. Consequently, nucleic acid sequences encoding proteins that include amino acid substitutions are also provided.

Modified proteins also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond.

Modified forms further include "chemical derivatives," in which one or more amino acids has a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide.

In some embodiments, an engineered VLP and ODN are formulated as a ratio. In some instances, the ratio is a w/w ratio. In some instances, the engineered VLP and ODN are formulated as a protein/ODN (w/w) ratio of 1:1, 2:1, 3:1, 4:1, 5:1, 6:1, 7:1, 8:1, 9:1, 10:1, 1:2, 1:3, 1:4, 1:5, 1:6, 1:7, 1:8, 1:9, or 1:10. In some cases, the engineered VLP and ODN are formulated as a protein/ODN (w/w) ratio of 1:1. In some cases, the engineered VLP and ODN are formulated as a protein/ODN (w/w) ratio of 2:1. In some cases, the engineered VLP and ODN are formulated as a protein/ODN (w/w) ratio of 3:1. In some cases, the engineered VLP and ODN are formulated as a protein/ODN (w/w) ratio of 4:1. In some cases, the engineered VLP and ODN are formulated as a protein/ODN (w/w) ratio of 5:1. In some cases, the engineered VLP and ODN are formulated as a protein/ODN (w/w) ratio of 6:1. In some cases, the engineered VLP and ODN are formulated as a protein/ODN (w/w) ratio of 7:1. In some cases, the engineered VLP and ODN are formulated as a protein/ODN (w/w) ratio of 8:1. In some cases, the engineered VLP and ODN are formulated as a protein/ODN (w/w) ratio of 9:1. In some cases, the engineered VLP and ODN are formulated as a protein/ODN (w/w) ratio of 10:1.

In some instances, an engineered VLP described herein further comprise, or consists essentially of, or yet further consists of, a label or a tag, e.g., such as a detectable label. A detectable label can be attached to, e.g., to the surface of a VLP or to an ODN encapsulated within the VLP.

Non-limiting exemplary detectable labels also include a radioactive material, such as a radioisotope, a metal or a metal oxide. Radioisotopes include radionuclides emitting alpha, beta or gamma radiation. In particular embodiments, a radioisotope can be one or more of: $^{3}H$, $^{10}B$, $^{18}F$, $^{11}C$, $^{14}C$, $^{13}N$, $^{18}O$, $^{15}O$, $^{32}P$, $P^{33}$, $^{35}S$, $^{35}Cl$, $^{45}Ti$, $^{46}Sc$, $^{47}Sc$, $^{51}Cr$, $^{52}Fe$, $^{59}Fe$, $^{57}Co$, $^{60}Cu$, $^{61}Cu$, $^{62}Cu$, $^{64}Cu$, $^{67}Cu$, $^{67}Ga$, $^{68}Ga$, $^{72}As$, $^{76}Br$, $^{77}Br$, $^{81m}Kr$, $^{82}Rb$, $^{85}Sr$, $^{89}Sr$, $^{86}Y$, $^{90}Y$, $^{95}Nb$, $^{94m}Tc$, $^{99m}Tc$, $^{97}Ru$, $^{103}Ru$, $^{105}Rh$, $^{109}Cd$, $^{111}In$, $^{113}Sn$, $^{113m}In$, $^{114}In$, $I^{125}$, $I^{131}$, $^{140}La$, $^{141}Ce$, $^{149}Pm$, $^{153}Gd$, $^{157}Gd$, $^{153}Sm$, $^{161}Tb$, $^{166}Dy$, $^{166}Ho$, $^{169}Er$, $^{169}Y$, $^{175}Yb$, $^{177}Lu$, $^{186}Re$, $^{188}Re$, $^{201}Tl$, $^{203}Pb$, $^{211}At$, $^{212}Bi$ or $^{225}Ac$.

Additional non-limiting exemplary detectable labels include a metal or a metal oxide. In particular embodiments, a metal or metal oxide is one or more of: gold, silver, copper, boron, manganese, gadolinium, iron, chromium, barium, europium, erbium, praseodynium, indium, or technetium. In additional embodiments, a metal oxide includes one or more of: Gd(III), Mn(II), Mn(III), Cr(II), Cr(III), Cu(II), Fe (III), Pr(III), Nd(III) Sm(III), Tb(III), Yb(III) Dy(III), Ho(III), Eu(II), Eu(III), or Er(III).

Further non-limiting exemplary detectable labels include contrast agents (e.g., gadolinium; manganese; barium sulfate; an iodinated or noniodinated agent; an ionic agent or nonionic agent); magnetic and paramagnetic agents (e.g., iron-oxide chelate); nanoparticles; an enzyme (horseradish peroxidase, alkaline phosphatase, β-galactosidase, or acetylcholinesterase); a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); or a bioluminescent material (e.g., luciferase, luciferin, aequorin).

Additional non-limiting examples of tags and/or detectable labels include enzymes (horseradish peroxidase, urease, catalase, alkaline phosphatase, beta-galactosidase, chloramphenicol transferase); enzyme substrates; ligands (e.g., biotin); receptors (avidin); GST-, T7-, His-, myc-, HA- and FLAG®-tags; electron-dense reagents; energy transfer molecules; paramagnetic labels; fluorophores (fluorescein, fluorscamine, rhodamine, phycoerthrin, phycocyanin, allophycocyanin); chromophores; chemi-luminescent (imidazole, luciferase, acridinium, oxalate); and bio-luminescent agents.

As set forth herein, a detectable label or tag can be linked or conjugated (e.g., covalently) to the VLP or ODN. In various embodiments a detectable label, such as a radionuclide or metal or metal oxide can be bound or conjugated to the agent, either directly or indirectly. A linker or an intermediary functional group can be used to link the molecule to a detectable label or tag. Linkers include amino acid or peptidomimetic sequences inserted between the molecule and a label or tag so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. The length of the linker sequence may vary without significantly affecting a function or activity.

Linkers further include chemical moieties, conjugating agents, and intermediary functional groups. Examples include moieties that react with free or semi-free amines, oxygen, sulfur, hydroxy or carboxy groups. Such functional groups therefore include mono and bifunctional cross-linkers, such as sulfo-succinimidyl derivatives (sulfo-SMCC, sulfo-SMPB), in particular, disuccinimidyl suberate (DSS), BS3 (Sulfo-DSS), disuccinimidyl glutarate (DSG) and disuccinimidyl tartrate (DST). Non-limiting examples include diethylenetriaminepentaacetic acid (DTPA) and ethylene diaminetetracetic acid.

Also provided herein is the engineered VLP as described herein further comprising, or consisting essentially of, or yet further consisting of an additional therapeutic agent.

In some cases, the additional therapeutic agent disclosed herein comprise, or consists essentially of, or yet further consists of, a chemotherapeutic agent, an immunotherapeutic agent, a targeted therapy, radiation therapy, or a combination thereof. Illustrative additional therapeutic agents include, but are not limited to, alkylating agents such as altretamine, busulfan, carboplatin, carmustine, chlorambucil, cisplatin, cyclophosphamide, dacarbazine, lomustine, melphalan, oxalaplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some cases, the engineered VLP with or without the additional therapeutic agent comprise, or consists essentially of, or yet further consists of, or is used as a first-line therapy. As used herein, "first-line therapy" comprises, or consists essentially of, or yet further consists of, a primary treatment for a subject with a cancer. In some instances, the cancer is a primary cancer. In other instances, the cancer is a metastatic or recurrent cancer. In some cases, the first-line therapy comprise, or consists essentially of, or yet further consists of, s chemotherapy. In other cases, the first-line treatment comprise, or consists essentially of, or yet further consists of, s radiation therapy. A skilled artisan would readily understand that different first-line treatments may be applicable to different type of cancers.

In some cases, the additional therapeutic agent comprise, or consists essentially of, or yet further consists of, or is used as a second-line therapy, a third-line therapy, a fourth-line therapy, or a fifth-line therapy. As used herein, a second-line therapy encompasses treatments that are utilized after the primary or first-line treatment stops. They can also be used as third-line, fourth-line or fifth line therapy. A third-line therapy, a fourth-line therapy, or a fifth-line therapy encompass subsequent treatments. As indicated by the naming convention, a third-line therapy encompass a treatment course upon which a primary and second-line therapy have stopped.

In some cases, the additional therapeutic agent comprise, or consists essentially of, or yet further consists of, a salvage therapy.

In some cases, the additional therapeutic agent comprise, or consists essentially of, or yet further consists of, a palliative therapy.

In some cases, the additional therapeutic agent comprise, or consists essentially of, or yet further consists of, an inhibitor of the enzyme poly ADP ribose polymerase (PARP). Exemplary PARP inhibitors include, but are not limited to, olaparib (AZD-2281, LYNPARZA®, from Astra Zeneca), rucaparib (PF-01367338, RUBRACA®, from Clovis Oncology), niraparib (MK-4827, ZEJULA®, from Tesaro), talazoparib (BMN-673, from BioMarin Pharmaceutical Inc.), veliparib (ABT-888, from Abb Vie), CK-102 (formerly CEP 9722, from Teva Pharmaceutical Industries Ltd.), E7016 (from Eisai), iniparib (BSI 201, from Sanofi), and pamiparib (BGB-290, from BeiGene).

In some cases, the additional therapeutic agent comprise, or consists essentially of, or yet further consists of, s an immune checkpoint inhibitor. Exemplary checkpoint inhibitors include:

- PD-L1 inhibitors such as Genentech's MPDL3280A (RG7446), anti-PD-L1 monoclonal antibody MDX-1105 (BMS-936559) and BMS-935559 from Bristol-Meyer's Squibb, MSB0010718C, and AstraZeneca's MEDI4736;
- PD-L2 inhibitors such as GlaxoSmithKline's AMP-224 (Amplimmune), and rHIgM12B7;
- PD-1 inhibitors such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANBO11, antibody MDX-1 106 (ONO-4538), Bristol-Myers Squibb's human IgG4 monoclonal antibody nivolumab (OPDIVO®, BMS-936558, MDX1106), AstraZeneca's AMP-514 and AMP-224, and Pidilizumab (CT-O11) from CureTech Ltd;
- CTLA-4 inhibitors such as Bristol Meyers Squibb's anti-CTLA-4 antibody ipilimumab (also known as YERVOY®, MDX-010, BMS-734016 and MDX-101), anti-CTLA4 antibody clone 9H10 from Millipore, Pfizer's tremelimumab (CP-675,206, ticilimumab), and anti-CTLA4 antibody clone BNI3 from Abeam;
- LAG3 inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12;
- B7-H3 inhibitors such as MGA271;
- KIR inhibitors such as Lirilumab (IPH2101);
- CD137 inhibitors such as urelumab (BMS-663513, Bristol-Myers Squibb), PF-05082566 (anti-4-1BB, PF-2566, Pfizer), or XmAb-5592 (Xencor);
- PS inhibitors such as Bavituximab; and inhibitors such as an antibody or fragments (e.g., a monoclonal antibody, a human, humanized, or chimeric antibody) thereof, RNAi molecules, or small molecules to TFM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some cases, the additional therapeutic agent comprise, or consists essentially of, or yet further consists of, s pembrolizumab, nivolumab, tremelimumab, or ipilimumab.

In some cases, the additional therapeutic agent comprise, or consists essentially of, or yet further consists of, s an antibody such as alemtuzumab, trastuzumab, ibritumomab tiuxetan, brentuximab vedotin, ado-trastuzumab emtansine, or blinatumomab.

In some cases, the additional therapeutic agent comprise, or consists essentially of, or yet further consists of, s a cytokine. Exemplary cytokines include, but are not limited to, IL-Iβ, IL-6, IL-7, IL-10, IL-12, IL-15, IL-21, or TNFα.

In some embodiments, the additional therapeutic agent comprise, or consists essentially of, or yet further consists of, a receptor agonist. In some instances, the receptor agonist comprise, or consists essentially of, or yet further consists of, s a Toll-like receptor (TLR) ligand. In some cases, the TLR ligand comprise, or consists essentially of, or yet further consists of, s TLR1, TLR2, TLR3, TLR4, TLR5, TLR6, TLR7, TLR8, or TLR9. In some cases, the TLR ligand comprise, or consists essentially of, or yet further consists of, s a synthetic ligand such as, for example, Pam3Cys, CFA, MALP2, Pam2Cys, FSL-1, Hib-OMPC, Poly I:C, poly A:U, AGP, MPL A, RC-529, MDF2p, CFA, or Flagellin.

In some cases, the additional therapeutic agent comprise, or consists essentially of, or yet further consists of, an adoptive T cell transfer (ACT) therapy. In one embodiment, ACT involves identification of autologous T lymphocytes in a subject with, e.g., anti-tumor activity, expansion of the autologous T lymphocytes in vitro, and subsequent reinfusion of the expanded T lymphocytes into the subject. In another embodiment, ACT comprise, or consists essentially of, or yet further consists of, use of allogeneic T lymphocytes with, e.g., anti-tumor activity, expansion of the T lymphocytes in vitro, and subsequent infusion of the expanded allogeneic T lymphocytes into a subject in need thereof.

In some instances, the additional therapeutic agent is, or can be used as a vaccine, optionally, an oncolytic virus. Exemplary oncolytic viruses include T-Vec (Amgen), G47A (Todo et al.), JX-594 (Sillajen), CG0070 (Cold Genesys), and Reolysin (Oncolytics Biotech).

In some instances, the VLP described herein is administered in combination with a radiation therapy.

In some instances, the VLP described herein is administered in combination with surgery.

As utilized herein, a pathogen comprise, or consists essentially of, or yet further consists of, a virus, a bacterium, protozoan, helminth, prion, or fungus. In some embodiments, the virus is a DNA virus or an RNA virus. The DNA viruses include single-stranded (ss) DNA viruses, double-stranded (ds) DNA viruses, or DNA viruses that contain both ss and ds DNA regions. The RNA viruses include single-stranded (ss) RNA viruses or double-stranded (ds) RNA viruses. In some cases, the ssRNA viruses are further classified into positive-sense RNA viruses or negative-sense RNA viruses.

Exemplary dsDNA viruses include viruses from the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

Exemplary ssDNA viruses include viruses from the family: Anelloviridae, Bacillariodnaviridae, Bidnaviridae, Circoviridae, Geminiviridae, Inoviridae, Microviridae, Nanoviridae, Parvoviridae, and Spiraviridae.

Exemplary DNA viruses that contain both ss and ds DNA regions include viruses from the group of pleolipoviruses. In some cases, the pleolipoviruses include Haloarcula hispanica pleomorphic virus 1, Halogeometricum pleomorphic virus 1, Halorubrum pleomorphic virus 1, Halorubrum pleomorphic virus 2, Halorubrum pleomorphic virus 3, and Halorubrum pleomorphic virus 6.

Exemplary dsRNA viruses include viruses from the family: Birnaviridae, Chrysoviridae, Cystoviridae, Endornaviridae, Hypoviridae, Megavirnaviridae, Partitiviridae, Picobirnaviridae, Reoviridae, Rotavirus, and Totiviridae.

Exemplary positive-sense ssRNA viruses include viruses from the family: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Marnaviridae, Mesoniviridae, Narnaviridae, Nodaviridae, Permutotetraviridae, Picornaviridae, Potyviridae, Roniviridae, Retroviridae, Secoviridae, Togaviridae, Tombusviridae, Tymoviridae, and Virgaviridae.

Exemplary negative-sense ssRNA viruses include viruses from the family: Arenaviridae, Bornaviridae, Bunyaviridae, Filoviridae, Nyamiviridae, Ophioviridae, Orthomyxoviridae, Paramyxoviridae, and Rhabdoviridae.

In some instances, an additional therapeutic agent in the context of a pathogenic infection comprise, or consists essentially of, or yet further consists of, an antibiotics or an antiviral treatments such as, but not limited to, acyclovir, brivudine, docosanol, famciclovir, foscarnet, idoxuridine, penciclovir, trifluridine, valacyclovir, and pritelivir.

In some instances, the pathogen is human immunodeficiency virus (HIV). In some cases, the additional therapeutic agent comprise, or consists essentially of, or yet further consists of, s an HIV antiretroviral therapy. Exemplary HIV antiretroviral therapy includes: nucleoside reverse transcriptase inhibitors (RTIs) such as abacavir, emtricitabine, lamivudine, tenofovir disoproxil fumarate, and zidovudine; non-nucleoside reverse transcriptase inhibitors (NNRTIs) such as efavirenz, etravirine, nevirapine, or rilpivirine; protease inhibitors (Pis) such as atazanavir, darunavir, fosamprenavir, ritonavir, saquinavir, and tipranavir; fusion inhibitors such as enfuvirtide; CCR5 antagonists such as maraviroc; integrase inhibitors such as dolutegravir and raltegravir; post-attachment inhibitors such as ibalizumab; pharmacokinetic enhancers such as cobicistat; and cocktails such as abacavir and lamivudine; abacavir, dolutegravir, and lamivudine; abacavir, lamivudine, and zidovudine; atazanavir and cobicistat; bictegravir, emtricitabine, and tenofovir alafenamide; darunavir and cobicistat; dolutegravir and rilpivirine; efavirenz, emtricitabine, and tenofovir disoproxil fumarate; efavirenz, lamivudine, and tenofovir disoproxil fumarate; efavirenz, lamivudine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and tenofovir disoproxil fumarate; lamivudine and zidovudine; and lopinavir and ritonavir.

In some instances, the pathogen is a hepatitis virus, e.g., hepatitis A, B, C, D, or E. In some cases, an additional therapeutic agent comprise, or consists essentially of, or yet further consists of, an antiviral therapy for hepatitis. Exemplary antiviral therapy for hepatitis include ribavirin; NS3/4A protease inhibitors such as paritaprevir, simeprevir, and grazoprevir; NS5A protease inhibitors such as ledipasvir, ombitasvir, elbasvir, and daclatasvir; NS5B nucleotide/nucleoside and nonnucleoside polymerase inhibitors such as sofosbuvir and dasabuvir; and combinations such as ledipasvir-sofosbuvir, dasabuvir-ombitasvir-paritaprevir-ritonavir; elbasvir-grazoprevir, ombitasvir-paritaprevir-ritonavir, sofosbuvir-velpatasvir, sofosbuvir-velpatasvir-voxilaprevir, and glecaprevir-pibrentasvir; and interferons such as peginterferon alfa-2a, peginterferon alfa-2b, and interferon alfa-2b.

Exemplary autoimmune disease or disorder include, but are not limited to, alopecia areata, autoimmune hemolytic anemia, autoimmune hepatitis, dermatomyositis, type 1 diabetes, juvenile idiopathic arthritis, glomerulonephritis, Graves' disease, Guillain-Barre syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjogren's syndrome, systemic lupus erythematosus, thyroiditis, uveitis, vitiligo, or Wegener's granulomatosis.

Exemplary additional therapeutic agents for the treatment of an autoimmune disease or disorder include, but are not limited to, corticosteroids such as prednisone, budesonide, or prednisolone; calcineurin inhibitors such as cyclosporine or tacrolimus; mTOR inhibitors such as sirolimus or everolimus; EVIDH inhibitors such as azathioprine, leflunomide, or mycophenolate; biologies such as abatacept, adalimumab, anakinra, certolizumab, etanercept, golimumab, infliximab, ixekizumab, natalizumab, rituximab, secukinumab, tocilizumab, ustekinumab, or vedolizumab; and monoclonal antibodies such as basiliximab, daclizumab, or muromonab.

Exemplary inflammatory conditions include, but are not limited to, asthma, chronic peptid ulcer, tuberculosis, rheumatoid arthritis, ulcerative colitis, and Crohn's disease.

Compositions

Also provided herein are compositions comprising the engineered VLP as described herein, alone or in combination with the additional therapeutic agents. In one aspect, the compositions further comprise, or consist essentially of, or yet further consist of, a carrier, such as a pharmaceutically acceptable carrier.

In another aspect, provided herein is a composition comprising, consisting essentially of, or consisting of the combination of compounds provided herein, and at least one pharmaceutically acceptable excipient.

In one embodiment, this technology relates to a composition comprising a combination of compounds as described herein and a carrier.

In another embodiment, this technology relates to a pharmaceutical composition comprising a combination of compounds as described herein and a pharmaceutically acceptable carrier.

In another embodiment, this technology relates to a pharmaceutical composition comprising an effective amount or a therapeutically effective amount of a combination of compounds as described herein and a pharmaceutically acceptable carrier.

Compositions, including pharmaceutical compositions comprising, consisting essentially of, or consisting of the engineered VLP alone or in combination of other therapeutic agents can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the combinations of compounds provided herein into preparations which can be used pharmaceutically.

In some embodiments, the pharmaceutical composition and formulations described herein are administered to a subject by multiple administration routes, including but not limited to, parenteral, oral, buccal, rectal, sublingual, or transdermal administration routes. In some cases, parenteral administration comprise, or consists essentially of, or yet further consists of, s intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration.

In some embodiments, the pharmaceutical formulations include, but are not limited to, lyophilized formulations, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995), Hoover, John E., Remington's Pharmaceutical Sciences, Mack Publishing Co., Easton, Pa. 1975, Liberman, H. A. and Lachman, L., Eds., Pharmaceutical Dosage Forms, Marcel Decker, New York, N.Y., 1980, and Pharmaceutical Dosage Forms and Drug Delivery Systems, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as AVICEL®, dibasic calcium phosphate, dicalcium phosphate dihydrate, tricalcium phosphate, calcium phosphate, anhydrous lactose, spray-dried lactose, pregelatinized starch, compressible sugar, such as Di-PAC® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or AMIJEL®, or sodium starch glycolate such as PROMOGEL® or EXPLOTAB®, a cellulose such as a wood product, methylcrystalline cellulose, e.g., AVICEL®, AVICEL® PH101, AVICEL® PH102, AVICEL® PH105, ELCEMA® P100, EMCOCEL®, VIVACEL®, MING TIA®, and SOLKA-FLOC®, methylcellulose, croscarmellose, or a cross-linked cellulose, such as cross-linked sodium carboxymethylcellulose (AC-DI-SOL®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as VEEGUM® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials.

Exemplary lubricants include, e.g., stearic acid, calcium hydroxide, talc, sodium stearyl fumerate, a hydrocarbon such as mineral oil, or hydrogenated vegetable oil such as hydrogenated soybean oil (STEROTEX®), higher fatty acids and their alkali-metal and alkaline earth metal salts, such as aluminum, calcium, magnesium, zinc, stearic acid, sodium stearates, glycerol, talc, waxes, STEAROWET®, boric acid, sodium benzoate, sodium acetate, sodium chloride, leucine, a polyethylene glycol (e.g., PEG-4000) or a methoxypolyethylene glycol such as CARBOWAX™, sodium oleate, sodium benzoate, glyceryl behenate, polyethylene glycol, magnesium or sodium lauryl sulfate, colloidal silica such as SYLOID™, CAB-O-SIL®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethyl citrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, poly sorb ate-20 or TWEEN® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., PLURONIC® (BASF), and the like. Additional surfactants include polyoxyethylene fatty acid glycerides and vegetable oils, e.g., polyoxyethylene (60) hydrogenated castor oil, and polyoxyethylene alkyl ethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

The pharmaceutical compositions for the administration of the combinations of compounds can be conveniently presented in dosage unit form and can be prepared by any of the methods well known in the art of pharmacy. The pharmaceutical compositions can be, for example, prepared by uniformly and intimately bringing the compounds provided herein into association with a liquid carrier, a finely divided solid carrier or both, and then, if necessary, shaping the product into the desired formulation. In the pharmaceutical composition, each compound of the combination provided herein is included in an amount sufficient to produce the desired therapeutic effect. For example, pharmaceutical compositions of the present technology may take a form suitable for virtually any mode of administration, including, for example, topical, ocular, oral, buccal, systemic, nasal, injection, infusion, transdermal, rectal, and vaginal, or a form suitable for administration by inhalation or insufflation.

For topical administration, the combination of compounds can be formulated as solutions, gels, ointments, creams, suspensions, etc., as is well-known in the art.

Systemic formulations include those designed for administration by injection (e.g., subcutaneous, intravenous, infusion, intramuscular, intrathecal, or intraperitoneal injection) as well as those designed for transdermal, transmucosal, oral, or pulmonary administration.

Useful injectable preparations include sterile suspensions, solutions, or emulsions of the compounds provided herein in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the combination of compounds provided herein can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the combination of compounds provided herein in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques well known to the skilled artisan. The pharmaceutical compositions of the present technology may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

In some embodiments, one or more compositions disclosed herein are contained in a kit. Accordingly, in some embodiments, provided herein is a kit comprising, consisting essentially of, or consisting of one or more compositions disclosed herein and instructions for their use.

Dosage and Dosage Formulations

In some embodiments, the compositions may be administered to a subject suffering from a condition as disclosed herein, such as a human, either alone or as part of a pharmaceutically acceptable formulation, once a week, once a day, twice a day, three times a day, or four times a day, or even more frequently.

Administration of the engineered VLPs alone or in combination with the additional therapeutic agent and compositions containing same can be effected by any method that enables delivery to the site of action. These methods include oral routes, intraduodenal routes, parenteral injection (including intravenous, subcutaneous, intramuscular, intravascular or infusion), topical, and rectal administration. Bolus doses can be used, or infusions over a period of 1, 2, 3, 4, 5, 10, 15, 20, 30, 60, 90, 120 or more minutes, or any intermediate time period can also be used, as can infusions lasting 3, 4, 5, 6, 7, 8, 9, 10, 12, 14 16, 20, 24 or more hours or lasting for 1-7 days or more. Infusions can be administered by drip, continuous infusion, infusion pump, metering pump, depot formulation, or any other suitable means.

Dosage regimens can be adjusted to provide the optimum desired response. For example, a single bolus can be administered, several divided doses can be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient can also be determined, as can the temporal requirements for administering each agent to provide a detectable therapeutic benefit to the patient. Accordingly, while certain dose and administration regimens are exemplified herein, these examples in no way limit the dose and administration regimen that can be provided to a patient in practicing the present disclosure.

It is to be noted that dosage values can vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining appropriate dosages and regimens for administration are well-known in the relevant art and would be understood to be encompassed by the skilled artisan once provided the teachings disclosed herein.

Diagnostic Methods

In some embodiments, one or more of the methods described herein further comprise, or consists essentially of, or yet further consists of, a diagnostic step. In some instances, a sample is first obtained from a subject suspected of having a disease or condition described above or for inducing an immune response in the subject. Exemplary samples include, but are not limited to, cell sample, tissue sample, tumor biopsy, liquid samples such as blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some instances, the sample is a tumor biopsy. In some cases, the sample is a liquid sample, e.g., a blood sample. In some cases, the sample is a cell-free DNA sample.

Various methods known in the art can be utilized to determine the presence of a disease or condition described herein or to determine whether an immune response has been induced in a subject. Assessment of one or more biomarkers associated with a disease or condition, or for characterizing whether an immune response has been induced, can be performed by any appropriate method. Expression levels or abundance can be determined by direct measurement of expression at the protein or mRNA level, for example by microarray analysis, quantitative PCR analysis, or RNA sequencing analysis. Alternatively, labeled antibody systems may be used to quantify target protein abundance in the cells, followed by immunofluorescence analysis, such as FISH analysis.

The compositions of the present disclosure can be administered by parenteral (e.g., intramuscular, intraperitoneal, intravenous, ICV, intracisternal injection or infusion, subcutaneous injection, or implant), oral, by inhalation spray nasal, vaginal, rectal, sublingual, urethral (e.g., urethral suppository) or topical routes of administration (e.g., gel, ointment, cream, aerosol, etc.) and can be formulated in suitable dosage unit formulations containing conventional non-toxic pharmaceutically acceptable carriers, adjuvants, excipients, and vehicles appropriate for each route of administration.

Uses of the Engineered VLPs and Compositions Containing Same

Provided herein is a method of treating a disease or condition or inducing an immune response in a cell or a subject in need thereof, comprising, or consisting essentially of, or yet further consisting of administering to the subject or cell (as appropriate) an engineered VLP or a composition as described herein. In one aspect, the cell or disease or condition is a cancer cell, or a cancer or tumor, e.g. a solid tumor. Non-limiting examples of a solid tumors or cells are bladder cancer, bone cancer, brain cancer, breast cancer, colorectal cancer, colon cancer, esophageal cancer, eye cancer, head and neck cancer, kidney cancer, lung cancer, melanoma, ovarian cancer, pancreatic cancer, prostate cancer, or stomach cancer. In a further aspect, the solid tumor is a colon cancer, pancreatic cancer or melanoma. In a further aspect, the cancer or cell is a hematologic malignancy, such as, for example, a lymphoma or leukemia. Non-limiting examples include a B-cell lymphoma, a T-cell lymphoma, a Hodgkin's lymphoma or a non-Hodgkin's lymphoma. The cancer can be primary or metastatic, e.g., Stage I, Stage II, Stage III or Stage IV. It also can be relapsed or refractory cancer. The cell can be a primary cell obtained from example, a biopsy or an established cell line obtained from example a commercial source such as the American Type Culture Collection (ATCC).

In one aspect, the method or VLP modulates, impedes, or inhibits the growth of a cancer cell or tumor growth. In a yet further aspect, the VLP promotes accumulation of tumor-infiltrating lymphocytes in the TME. In one aspect, the method is practiced in vitro and can serve as an assay to test new combination therapies or dosage regimens. It also can be used as a personalized assay by administering to a subject's cancer or tumor cell in vitro the VLP or composition containing same to the cell. One of skill in the art can use conventional assays, such as reduction in tumor size, tumor burden or a reduction in an appropriate cancer marker to determine if the method is appropriate for the subject in need of such treatment. The methods can be practiced clinically or in laboratory animals as an animal model to test for new combination therapies. One of skill in the art can use conventional assays, such as reduction in tumor size, tumor burden or a reduction in an appropriate cancer marker to determine if the method is appropriate for the subject in need of such treatment or if the treatment has been successful or requires repeating or a change in dosage.

In a further aspect, the VLP modulates secretion of a cytokine from the immune cell, optionally the macrophage, thereby to induce an immunostimulation. In one aspect, the cytokine is a pro-inflammatory cytokine. Non-limiting examples of cytokines are TNFα, IFNγ, IL-1, IL-12, IL-18, or GM-CSF. Methods to measure cytokines are known in the art.

In a further aspect, the method or VLP induces an immune response in the subject in need thereof. In one aspect, the method or VLP modulates activation of phagocytosis in the immune cell. In one aspect, the immune cell is the macrophage. In another aspect, the VLP modulates polarization of the macrophage toward a M1 phenotype. In a further aspect, the VLP decreases the macrophage toward a M2 polarization. In a yet further aspect, the VLP promotes accumulation of tumor-infiltrating lymphocytes in the TME. Methods to measure TIL are known in the art. The methods can be practiced clinically or in laboratory animals as an animal model to test for new combination therapies. One of skill in the art can use conventional assays for measuring immune responses.

In a further aspect, the VLP modulates secretion of a cytokine from the immune cell, optionally the macrophage, thereby to induce an immunostimulation. In one aspect, the cytokine is a pro-inflammatory cytokine. Non-limiting examples of cytokines are TNFα, IFNγ, IL-1, IL-12, IL-18, or GM-CSF. The methods can be practiced clinically or in laboratory animals as an animal model to test for new combination therapies. Methods to measure cytokines are known in the art.

The subject of these methods can be an animal, a mammal or a human in need of such treatment. When the methods are practiced in vitro, the cell can be an animal cell, a mammalian cell or a human cell. In one aspect an effective amount is administered which can be determined using conventional techniques. When the treatment relates to cancer therapy, the method or treatment can be a first-line, second-line, third-line or fourth-line therapy. In can be an adjuvant therapy and combined with other therapies as determined by the treating veterinarian or physician. Any appropriate means of administration can be used, also as determined by the treating veterinarian or physician. The treatments can be combined with diagnostic assessment before or after therapy. Thus, the therapy can be personalized to the subject in need of such treatment.

Provided herein is a method of treating an inflammatory condition in a subject in need thereof, comprising, or consisting essentially of, or yet further consisting of administering to the subject an engineered VLP or a composition as described herein. Further provided is a method of treating an autoimmune disease in a subject in need thereof, comprising, or consisting essentially of, or yet further consisting of administering to the subject an engineered VLP or a composition as described herein. The methods can be practiced clinically or in laboratory animals as an animal model to test for new combination therapies. Methods to measure inflammatory responses are known in the art.

Yet further provided is a method of treating an allergy in a subject in need thereof, comprising, or consisting essentially of, or yet further consisting of administering to the subject an engineered VLP or a composition as described herein. The disease or condition is an inflammatory condition. In one aspect, the allergy, comprises asthma, allergic asthma or allergic rhinosinusitis. The methods can be practiced clinically or in laboratory animals as an animal model to test for new combination therapies. Methods to measure allergic responses are known in the art.

Still further provided is a method of treating a pathogenic condition in a subject in need thereof, comprising, or consisting essentially of, or yet further consisting of administering to the subject an engineered VLP or a composition as described herein. In one aspect, the pathogen is a virus, e.g., human immunodeficiency virus (HIV) or a Hepatitis virus, optionally a Hepatitis B virus or a Hepatitis C virus. In another aspect, the pathogen is a bacterium, protozoan, helminth, prion, or fungus. Non-limiting examples of such include *Vibrio parahaemolyticus* or rock bream iridovirus, *Edwardsiella tarda*, or *Vibrio vulrifcus*. In additional aspects of the above disclosures, the VLP or composition containing the VLP comprises, or consists essentially of, or yet further consists of, a surface polypeptide that preferentially homes to a TME. In one aspect, the VLP targets a TAM.

The methods can be practiced clinically or in laboratory animals as an animal model to test for new combination therapies. Methods to measure pathogenic infection are known in the art.

Further provided is a method of modulating phagocytosis in a target cell, comprising, or consisting essentially of, or yet further consisting of contacting the target cell or a plurality of target cells comprising, or consisting essentially of, or yet further consisting of a macrophage with an engineered VLP or composition containing same for a first time sufficient to activate phagocytic activity of the macrophage and contacting the activated macrophage with the target cell for a second time sufficient to induce phagocytosis of the target cell. In one aspect, the macrophage has a M1 phenotype. In another aspect, the target cell or the plurality of cells are located in a tumor microenvironment (TME). In a further aspect, the cell or the plurality of cells comprise, or consists essentially of, or yet further consists of, antigen-presenting cells (APCs), non-limiting examples of such include dendritic cells, B cells, or a combination thereof. In a further aspect, the target cell or population comprise a cancer cell.

In one aspect, the target cell or population comprising the target cell comprises a cancer cell, or a cancer or tumor, e.g. a solid tumor. Non-limiting examples of a solid tumors or cells are bladder cancer, bone cancer, brain cancer, breast cancer, colorectal cancer, colon cancer, esophageal cancer, eye cancer, head and neck cancer, kidney cancer, lung cancer, melanoma, ovarian cancer, pancreatic cancer, prostate cancer, or stomach cancer. In a further aspect, the solid tumor is a colon cancer, pancreatic cancer or melanoma. In a further aspect, the cancer or cell is a hematologic malignancy, such as, for example, a lymphoma or leukemia. Non-limiting examples include a B-cell lymphoma, a T-cell lymphoma, a Hodgkin's lymphoma or a non-Hodgkin's lymphoma. The cancer can be primary or metastatic, e.g., Stage I, Stage II, Stage III or Stage IV. It also can be relapsed or refractory cancer. The cell can be a primary cell obtained from example, a biopsy or an established cell line obtained from example a commercial source such as the American Type Culture Collection (ATCC).

In one aspect, the method inhibits the growth of a cancer cell or tumor growth. In one aspect, the method is practiced in vitro and can serve as an assay to test new combination therapies or dosage regimens. It also can be used as a personalized assay by administering to a subject's cancer or tumor cell in vitro the VLP or composition containing same to the cell. One of skill in the art can use conventional assays, such as reduction in tumor size, tumor burden or a reduction in an appropriate cancer marker to determine if the method is appropriate for the subject in need of such treatment or if the treatment has been successful or requires repeating or a change in dosage. The methods can be practiced clinically or in laboratory animals as an animal model to test for new combination therapies. One of skill in the art can use conventional assays, such as reduction in tumor size, tumor burden or a reduction in an appropriate cancer marker to determine if the method is appropriate for the subject in need of such treatment.

The subject of these methods can be an animal, a mammal or a human in need of such treatment. When the methods are practiced in vitro, the cell can be an animal cell, a mammalian cell or a human cell. In one aspect an effective amount is administered which can be determined using conventional techniques. When the treatment relates to cancer therapy, the method or treatment can be a first-line, second-line, third-line or fourth-line therapy. In can be an adjuvant therapy and combined with other therapies as determined by the treating veterinarian or physician. Any appropriate means of administration can be used, also as determined by the treating veterinarian or physician. The treatments can be combined with diagnostic assessment before or after therapy. Thus, the therapy can be personalized to the subject in need of such treatment.

In another aspect, the target cell or plurality of target cells comprise a cell infected by a pathogen. In one aspect, the pathogen is a virus, e.g., human immunodeficiency virus (HIV) or a Hepatitis virus, optionally a Hepatitis B virus or a Hepatitis C virus. In another aspect, the pathogen is a bacterium, protozoan, helminth, prion, or fungus. Non-limiting examples of such include *Vibrio parahaemolyticus* or rock bream iridovirus, *Edwardsiella tarda*, or *Vibrio vulrificus*. The methods can be practiced clinically or in laboratory animals as an animal model to test for new combination therapies. Methods to measure pathogenic infection are known in the art.

Also provided is a method of modulating M1 macrophage polarization, comprising, or consisting essentially of, or yet further consisting of contacting a plurality of antigen presenting cells (APCs) comprising, or consisting essentially of, or yet further consisting of at least one macrophage with an engineered VLP or composition as described herein for a time sufficient to induce secretion of a plurality of cytokines by the plurality of APCs, whereby the secretion of the plurality of cytokines modulate M1 activation of the macrophage. In one aspect, the APCs are located within a tumor microenvironment. In another aspect, the plurality of cytokines comprise, or consists essentially of, or yet further consists of IFN$\gamma$, TNF$\alpha$, or a combination thereof. In a further aspect, the VLP or composition decreases M2 activation of the macrophage. In a yet further aspect, the APCs further comprise, or consists essentially of, or yet further consists of dendritic cells, B cells, or a combination thereof.

In one aspect, the method is practiced in vitro. In another aspect, the method is an in vivo method. In a further aspect, the method is an ex vivo method.

In one aspect, the method is practiced in vitro and can serve as an assay to test new combination therapies or dosage regimens. The methods can be practiced clinically or in laboratory animals as an animal model to test for new combination therapies. One of skill in the art can use conventional assays, to determine efficacy. The subject of these methods can be an animal, a mammal or a human in need of such treatment.

When the methods are practiced in vitro, the cell can be an animal cell, a mammalian cell or a human cell. In one aspect an effective amount is administered which can be determined using conventional techniques. When the treatment relates to cancer therapy, the method or treatment can be a first-line, second-line, third-line or fourth-line therapy. In can be an adjuvant therapy and combined with other therapies as determined by the treating veterinarian or physician. Any appropriate means of administration can be used, also as determined by the treating veterinarian or physician. The treatments can be combined with diagnostic assessment before or after therapy. Thus, the therapy can be personalized to the subject in need of such treatment.

In some embodiments as described herein, the VLP or compositions described herein are administered for clinical or therapeutic applications.

In some embodiments, the VLP or composition and/or formulation as described herein are administered to a subject by multiple administration routes, including but not limited to, parenteral, oral, buccal, rectal, sublingual, or transdermal administration routes. In some cases, parenteral administration comprise, or consists essentially of, or yet further consists of, intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration.

In some embodiments, the VLP, composition or formulation is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits

As used herein, a kit or article of manufacture described herein include a carrier, package, or container that is compartmentalized to receive one or more containers such as vials, tubes, and the like, each of the container(s) comprising, or consisting essentially of, or yet further consisting of, one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

These examples are provided for illustrative purposes only and not to limit the scope of the claims provided herein.

Example 1—The Antitumor Efficacy of CpG Oligonucleotides is Improved by Encapsulation in Plant Virus-Like Particles Preparation of CCMV and VLPs CCMV was propagated by molecular farming, purified as previously reported[45] and stored in 0.1 M sodium acetate/1 mM EDTA (pH 4.8). The VLPs were prepared according to our well-established procedures.[35, 37] Briefly, CCMV virions were dialyzed against disassembly buffer (0.5 M $CaCl_2$), 50 mM Tris-HCl pH 7.5, 1 mM EDTA, 1 mM DTT, 0.5 mM PMSF) at 4° C. for 24 h in a 3.5 kDa MWCO Slide-a-Lyzer dialysis cassette (Thermo Fisher Scientific) and centrifuged at 12,000×g for 30 min at 4° C. to pellet the precipitated viral RNA. The supernatant was then centrifuged at 220,000×g for 2 h at 4° C. to pellet any non-disassociated virus particles. The supernatant (capsid protein solution) was then dialyzed against protein buffer (1 M NaCl, 20 mM Tris pH 7.2, 1 mM EDTA, 1 mM DTT, 1 mM PMSF) as above and stored at 4° C. The concentration of the CCMV coat proteins was determined by measuring the absorbance at 280 nm (A280) using the extinction coefficient (F)=1.27 $\mu L\ g^{-1}cm^{-1}$, and the purity was determined by calculating the A280/A260 ratio. Values greater than 1.5 indicated the absence of nucleic acid contamination, and these particles were suitable for reassembly.

The encapsulated ODNs were prepared by mixing coat proteins and ODNs (ODN1826 and ODN2138, Invitrogen) at a 6:1 (w/w) ratio in protein buffer. The mixture was dialyzed against RNA assembly buffer (50 mM Tris-HCl pH 7.2, 50 mM NaCl, 10 mM KCl, 5 mM MgCl2, 1 mM DTT) and then immediately against virus suspension buffer (50 mM sodium acetate, 8 mM magnesium acetate, pH 4.5) in each case for at least 6 h at 4° C. using the equipment described above. The eCCMV sample was reassembled under high-salt conditions in the presence of $Mg^{2+}$ (0.9 M NaCl, 0.1 M sodium acetate pH 4.8, 10 mM MgCl2, 0.5 mM PMSF). The reassembled VLPs were purified by ultracentrifugation at 220,000×g for 1 h at 4° C. All VLPs were diluted in PBS immediately before in vitro and in vivo experiments.

Characterization of VLPs

The Quant-iT RiboGreen RNA Assay kit (Thermo Fisher Scientific) was used to quantify the encapsulated ODNs using the free ODNs as standards. UV-Vis spectra were acquired using a NanoDrop spectrophotometer (Thermo Fisher Scientific) at a concentration 0.5-1 mg $mL^{-1}$. About 5 μg of each VLP preparation was separated by 1.2% (w/v) agarose gel electrophoresis in 1×TAE running buffer, and imaged the gels before and after staining with Coomassie Brilliant Blue using the FluorChem R imaging system. SEC analysis was carried out using an AKTA Explorer chromatography system (GE Healthcare) fitted with a Suprose 6 Increase column. ~100 μg of each VLP preparation was loaded and carried out SEC at a flow rate 0.5 mL $min^{-1}$, measuring the absorbance at 260 and 280 nm. A DynaPro NanoStar (Wyatt Technology) was used for the analysis of VLPs by DLS at a concentration 0.3 mg $mL^{-1}$. VLPs negatively stained with uranyl acetate were observed using a FEI Tecnai F30 transmission electron microscope.

In Vitro Stability Analysis

Wild-type CCMV and CCMMV-ODN1826 were diluted in PBS (pH 7.4) at a concentration of 1 mg $mL^{-1}$ and incubated at 37° C., with 100-μL aliquots taken periodically for SEC analysis and PBS as the elution buffer. The ratio of intact to disassembled particles was determined by measuring the absorbance at 260 nm.

For resistance to DNase digestion, CCMV-ODN1826 was diluted in PBS (pH 7.4) at a concentration of 2 mg $mL^{-1}$. DNase I (Thermo Fisher Scientific) was added at final concentration of 5 U $mL^{-1}$, then incubated at 37° C. Aliquots were taken periodically for SEC analysis.

Cells and Mice

Mouse CT26 (ATCC) and CT26-luc cells (provided by Jeremy Rich, UCSD) were maintained in RPMI 1640 medium (Corning Life Sciences) supplemented with 10% (v/v) fetal bovine serum (Atlanta Biologicals) and 1% (v/v) penicillin/streptomycin (Thermo Fisher Scientific). B16F10 cells (ATCC) were maintained in DMEM (Corning Life Sciences) supplemented with 10% (v/v) fetal bovine serum and 1% (v/v) penicillin/streptomycin. The cells were incubated at 37° C. in a 5% C02 atmosphere. RAW-Blue cells (InvivoGen) were maintained in DMEM supplemented with 10% (v/v) fetal bovine serum, 1% (v/v) penicillin/streptomycin, 100 μg $mL^{-1}$ Normocin and Zeocin.

BALB/c and C57BL/6 mice were obtained from The Jackson Laboratory and were bred in-house at the Moores Cancer Center (UCSD). Animals were housed in groups with unlimited access to food and water. All mouse studies were performed in compliance with the Institutional Animal Care and Use Committee (IACUC) of UCSD.

Generation of BMDMs

BMDMs were derived by isolating bone marrow from BALB/c mice. Following treatment with ACK lysis buffer (Thermo Scientific Fisher), bone-marrow cells were cultured in Iscove's modified Eagle's medium (Thermo Scientific Fisher) supplemented with 10% (v/v) fetal bovine serum, 2 mM GlutaMAX, 10 ng $mL^{-1}$ gentamicin and 10 ng $mL^{-1}$ M-CSF (Peprotech) for 7-10 days. Before experiments, BMDMs were resuspended in the same medium without M-CSF.

Analysis of VLP Internalization by Macrophages and Tumor Cells

CT26 tumors were harvested and single-cell suspensions were prepared using the Tumor Dissociation Kit (Miltenyi Biotec) with the gentleMACS Octo Dissociator (Miltenyi Biotec). About $1\times10^6$ cells was suspended in RPMI 1640 medium supplemented with 10% (v/v) fetal bovine serum and 1% (v/v) penicillin/streptomycin and transferred the cells to six-well plates. About 0.2 μg ODN1826-CY5 or 2 μg CCMV-ODN1826-CY5 was then added and incubated the cells at 37° C. in a 5% $CO^2$ atmosphere for 1 h. The cells were harvested and treated with Fc-block (BioLegend), then stained with Zombie Aqua (BioLegend). The cells were then washed in FACS buffer (2% fetal bovine serum in PBS), and then stained with the following antibodies: Pacific Blue anti-mouse CD45, FITC anti-mouse CD11b, and PE anti-mouse F4/80 (all from BioLegend). After washing with FACS buffer, cells were acquired for immediate analysis using a BD LSR II flow cytometer (BD Biosciences). Data were analyzed using FlowJo v8.6.3 software. Tumor cells were gated as $CD45^-$ cells, and TAMs were gated as $CD45^+$ $CD11b^+$ $F4/80^+$ cells.

In Vitro Phagocytosis Assay

CT26 cells were labeled with 5 μM CFSE (Thermo Fisher Scientific) before seeding in transparent 12-well tissue culture plates at $2\times10^5$ cells per well. BMDMs were gathered as a single-cell suspension and seeded at $2\times10^5$ cells per well. ODN1826 (final concentration 50 μg $mL^{-1}$) or VLPs (final concentration 500 μg $mL^{-1}$) was then added and incubated the cells for 24 h as above. The cells were then harvested and stained with the following antibodies: Pacific Blue anti-mouse CD45, APC/Cy7 anti-mouse CD11b, and PE anti-mouse F4/80 (all from BioLegend). After washing with FACS buffer, the cells were acquired for immediate analysis as above. Unstimulated BMDMs were gated as $CD45^+$ $CD11b^+$ $F4/80^+$ cells, and phagocytic BMDMs were gated as $CD45^+$ $CD11b^+$ $F4/80^+$ $FITC^+$ cells.

In Vitro Antitumor Assay

CT26-luc cells were collected as a single-cell suspension and seeded into 96-well tissue culture plates at $5\times10^4$ cells per well. BMDMs were collected by mechanical detachment and seeded at a 1:1 macrophage-to-tumor-cell ratio. ODN1826 and the VLPs were then added as described above. After co-culture for 48 h, tumor cell survival was determined by luciferase assay (Goldbio), with luminescence measured using a Tecan microplate reader. Tumor cell survival was determined by normalizing the luminescence to tumor-only controls. CT26 tumors were collected and single-cell suspensions were prepared as described above. TAMs were isolated using Anti-F4/80 MicroBeads (Miltenyi Biotec). The antitumor assay using TAMs was performed as described above for BMDMs.

M1/M2 Polarization

BMDMs were collected as single-cell suspensions and seeded into 24-well tissue culture plates at $2\times10^5$ cells per well. ODN1826 (final concentration 50 μg $mL^{-1}$) or VLPs (final concentration 500 μg $mL^{-1}$) was then added and co-cultured the cells for 48 h as above. The cells were harvested and incubated for 10 min at 4° C. with an anti-mouse CD16/32 antibody (BioLegend) to block Fcγ receptors, washed with FACS buffer and stained with the antibodies against CD45, CD11b and F40-80 listed above. The cells were then fixed, permeabilized in Cytofix/Cytoperm Plus (BD Biosciences) and stained with PE/Cy7 anti-mouse iNOS (BD Biosciences) and AF488 anti-mouse Arg1 (BD Biosciences). After washing, the cells were acquired for immediate analysis by flow cytometry as described above. Macrophages were gated as $CD45^+CD11b^+$ $F4/80^+$ cells. The iNOS/Arg ratio was determined by dividing the number of iNOS' macrophages by the number of $Arg^+$ macrophages in each sample. For in vivo M1/M2 polarization, CT26 tumors were collected and single-cell suspensions were prepared as above, and the cells were stained and the data analyzed using the procedures described for BMDMs.

Cytokine Assay

BMDMs were collected as a single-cell suspension and seeded into 24-well tissue culture plates at $2\times10^5$ cells per well. ODN1826 (final concentration 50 μg $mL^{-1}$) or the VLPs (final concentration 500 μg $mL^{-1}$) was added and incubated the cells for 48 h. The presence of IFN-γ, IL-6, IL-1β, TNF-α, IL-12 p70 and CCL2 secreted by BMDMs was detected in the supernatant using cytokine kits from Thermo Fisher Scientific.

TRLs Activation

The TLR screening was run by InvivoGen. Briefly, in a 96-well plate (200 μL total volume) containing the appropriate cells (50,000 cells/well), 20 μL of the test article or the positive control ligand is added to the wells. The media added to the wells is designed for the detection of NF-κB induced SEAP expression. After a 20 hr incubation the optical density is read at 650 nm on a Molecular Devices SpectraMax 340PC absorbance detector.

Stimulation of TLRs in RAW-Blue Cells

RAW-Blue cells were mechanically detached and resuspended in test medium (DMEM supplemented with 10% (v/v) heat-inactivated FBS). Cells were plated on 96-well tissue plate (100000 cells in 180 μL test medium per well), then 20 μL of ODN or CCMV samples were added to the wells. 1 μg of VLPs per well or 0.1 μg ODN1826 were added. After 20 h incubation, 20 μL of the supernatant from each well were mixed with 180 μL of QUANTI-Blue solution on another 96-well plate. After 3 h incubation, SEAP levels were determined using a Tecan microplate reader (OD655 nm).

In Vivo Antitumor Efficacy

For the murine colon cancer model, CT26 cells were harvested and resuspended in RPMI-1640 medium at a concentration of $2\times10^6$ cells per mL and mixed 1:1 (v/v) with Matrigel (Corning) at 4° C. BALB/c mice were injected s.c. with 100 μL of the mixture ($1\times10^5$ cells) into the right flank. Tumors were allowed grow for 8-10 days until the volume reached 30-50 $mm^3$ before randomization and treatments. ODN1826 and the VLPs were administered i.t. with an injection volume of 20 μL. Three treatments in total were administered at intervals of 7 days. Tumors were measured at least every other day using digital calipers. The tumor size (in cubic millimeters) was calculated using the formula: $(\text{width}^2\times\text{length})/2$. When the tumor size reached 1000 $mm^3$, the mice were euthanized.

For the murine melanoma model, B16F10 cells were harvested and resuspended in PBS at a concentration of $5\times10^6$ cells per mL. C57BL/6 mice were injected i.d. with 30 μL of the mixture ($1.5\times10^5$ cells) into the right flank. Tumors were allowed grow for 8-10 days until the volume reached 30-50 $mm^3$ before randomization, treatments and measurements were carried out as described above.

Statistical Analysis

Data reported in the figures were analyzed and charts were generated using Prism 5 (GraphPad Software). Statistical significance was determined by two-way or one-way analysis of variance (ANOVA), unless otherwise stated. Survival data were compared using the Mantel-Cox (log-rank) test. In the figures, asterisks represent the following p values: *$p<0.05$, $p<0.01$, and *$p<0.001$.

Disassembly and Reassembly of CCMV to Encapsulate ODNs

CCMV particles were produced by molecular farming and purified by chloroform extraction, PEG precipitation and ultracentrifugation. The encapsulation of ODNs was achieved by pH/salt-dependent disassembly and reassembly (FIG. 1A).[37, 38] Briefly, wild-type CCMV particles were disassembled by increasing the pH and salt concentration of the buffer, which also precipitated the native viral genomic RNA. The resulting CCMV capsid protein solution was then mixed with therapeutic ODN1826 or the negative control ODN2138 at a 6:1 (w/w) ratio[38] and reassembled in a dilute, low-pH buffer in the presence of $Mg^{2+}$.[37] After reassembly, the CCMV-ODN VLPs were purified by ultracentrifugation to remove excess ODNs and capsid proteins. If the low-pH buffer contained a high concentration of salts, the CCMV capsid proteins reassembled without nucleic acids to form empty particles (eCCMV).

Figure 1B:
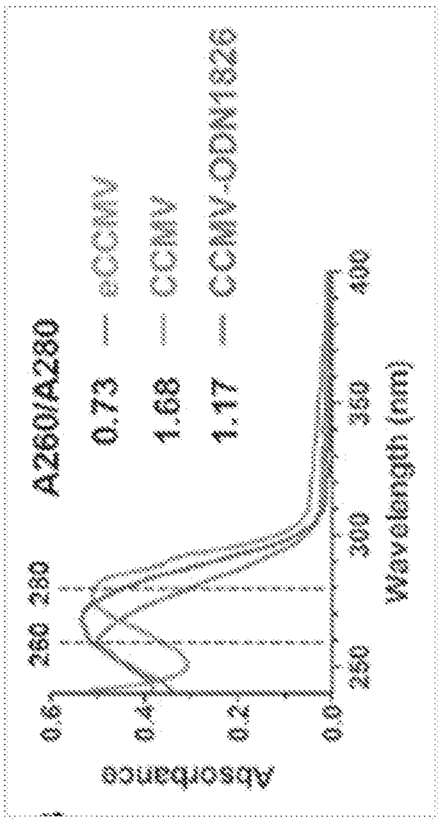
Figure 1C:
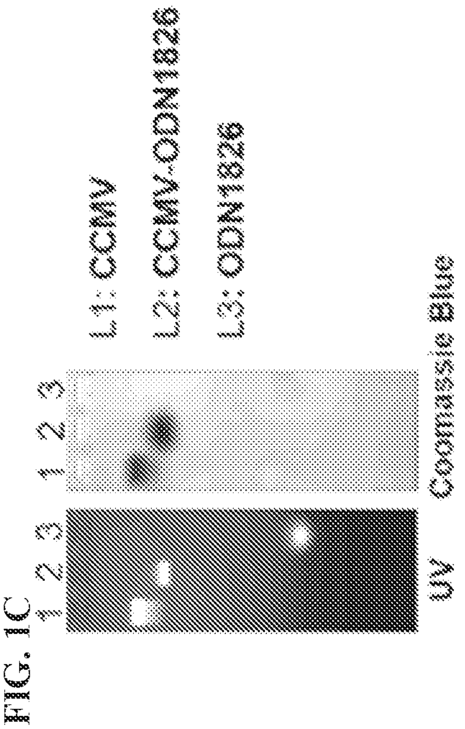
Figure 1D:
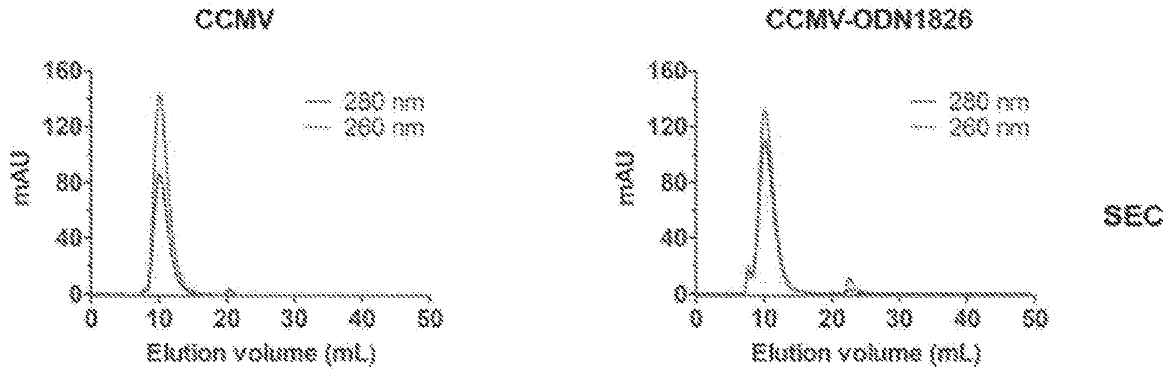
Figure 1E:
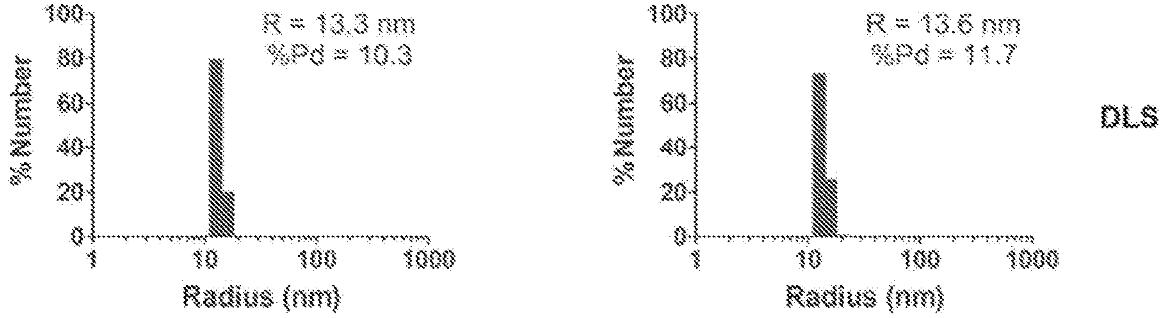
Figure 1F:
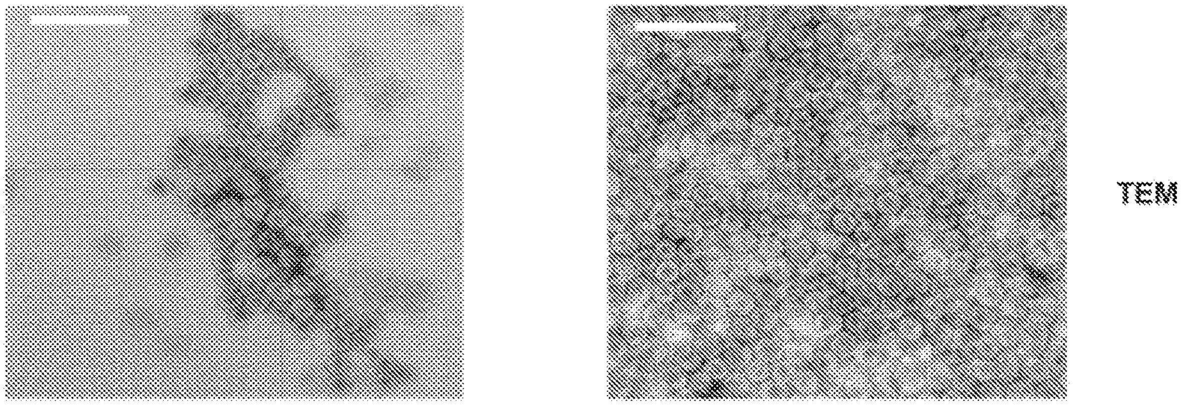

UV-Vis absorbance spectrophotometry (FIG. 1B) revealed that the A260/A280 ratio of the CCMV-ODN1826 VLPs was 1.17, which is similar to the native CCMV particles (1.68) and thus indicates the successful encapsulation of nucleic acids. In contrast, the A260/A280 ratio of the eCCMV particles was 0.73, reflecting the lack of nucleic acid, which absorbs strongly at 260 nm. The RiboGreen nucleic acid assay indicated that 50 CpG-ODNs were encapsulated per particle. This corresponds to 1100 nucleotides in total, whereas ~3200 nucleotides of RNA can be packaged (similar to the size of the wild-type CCMV genomic RNA).[38] CCMV therefore appears to package RNA more efficiently than ODNs. The presence of ODNs in the VLPs was further confirmed by native agarose gel electrophoresis (FIG. 1C) and the structural integrity of the particles was confirmed by size-exclusion chromatography (SEC) (FIG. 1D), with neither method showing any evidence of free ODNs in the VLP preparations. The precise size of the VLPs was determined by dynamic light scattering (DLS) (FIG. 1E) and transmission electron microscopy (TEM) (FIG. 1F). Both measurements confirmed that CCMV-ODN1826 was structurally similar to wild-type CCMV, revealing an icosahedral structure with a diameter of ~27 nm. This disassembly and reassembly approach is therefore a rapid and efficient way to prepare CCMV-ODN VLPs.

In Vitro Stability of CCMV-ODN VLPs

Figure 2A:
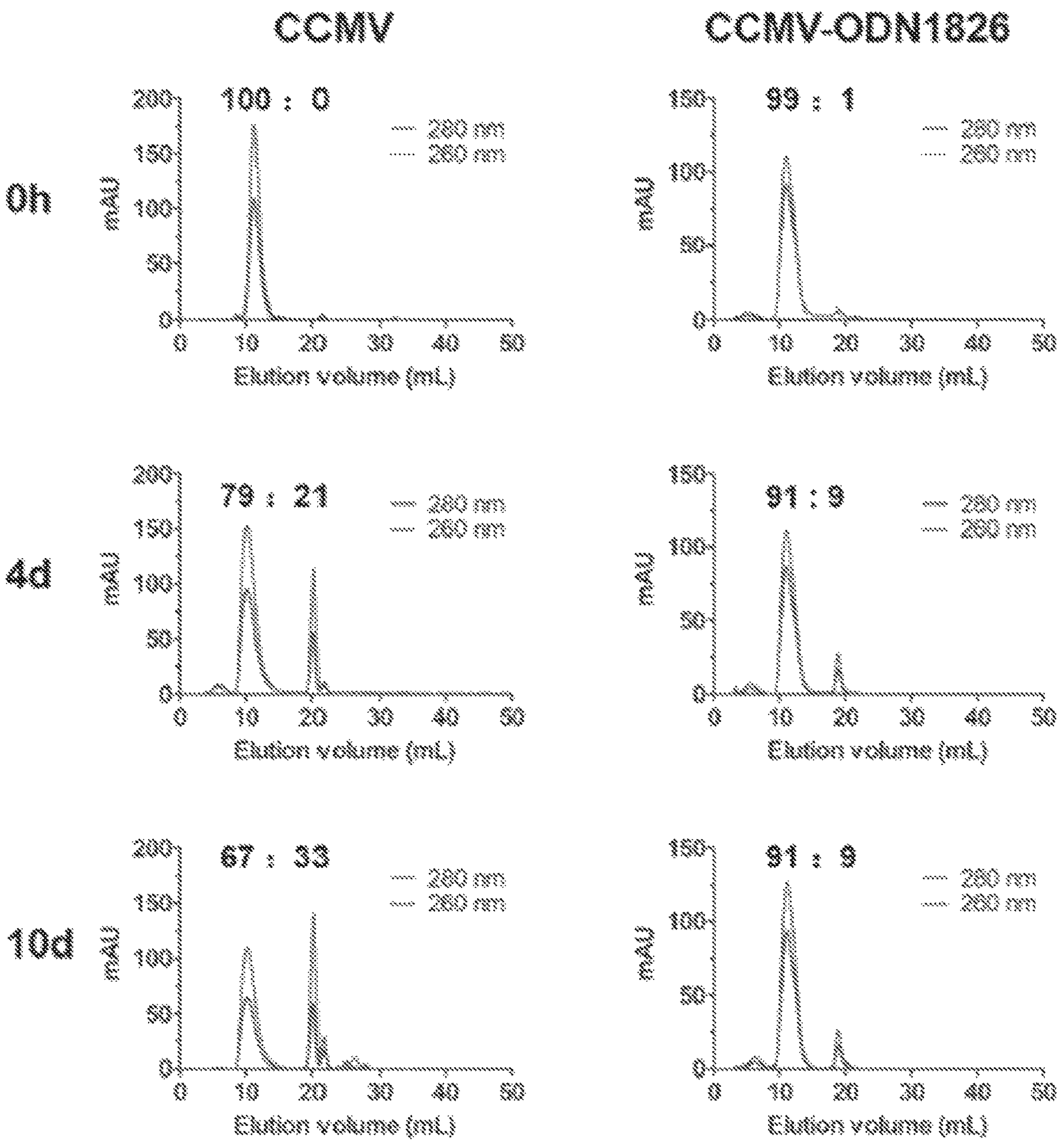
FIGS. 2A-2B illustrate stability of CCMV and CCMV-ODN VLPs under physiological conditions.
Figure 2B:
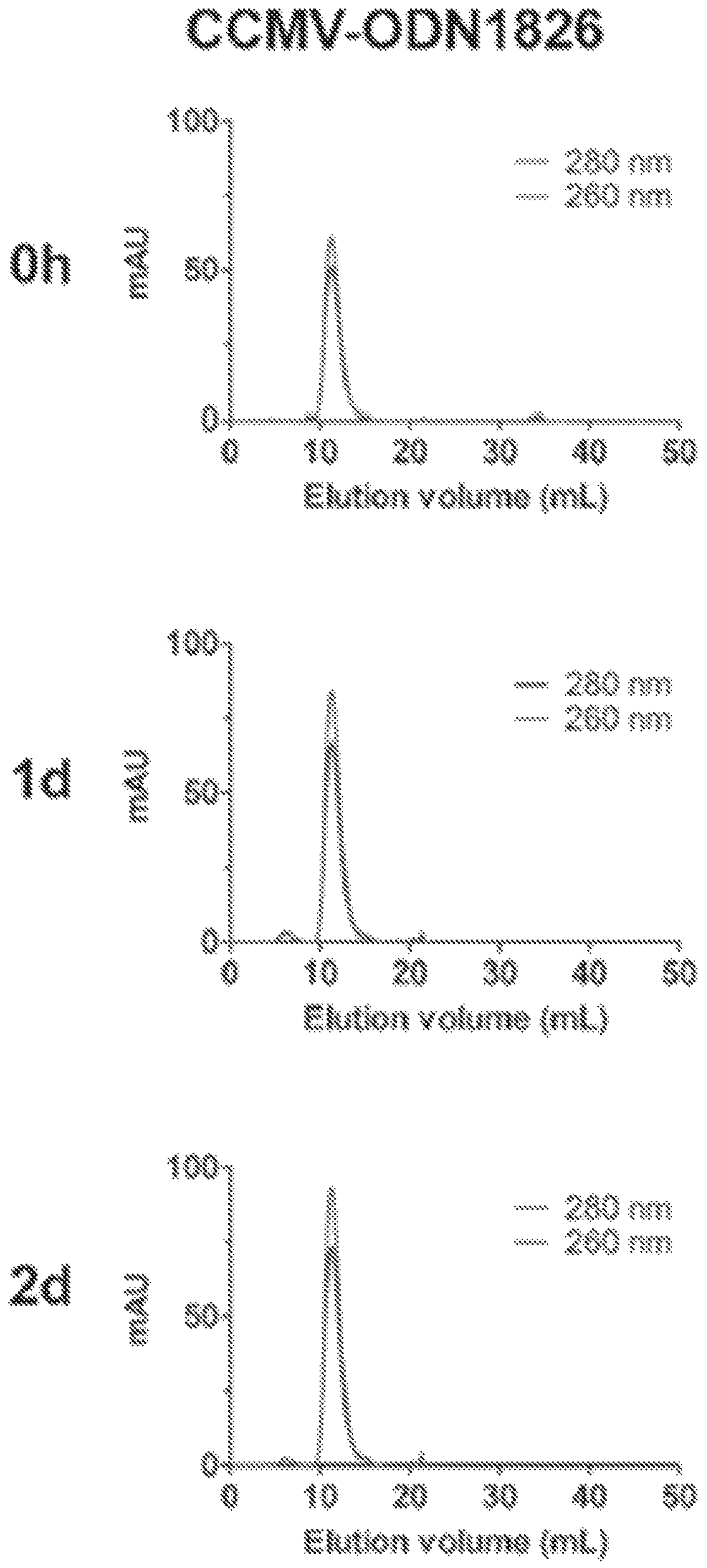

To exclude the possibility that the stability of the CCMV-ODN VLPs is limited to the conditions imposed during the disassembly and reassembly procedure, their stability under physiological conditions were tested. Wild-type CCMV and CCMV-ODN1826 were diluted to 1 mg mL-1 in phosphate buffered saline (PBS, pH 7.4) and incubated at 37° C. Samples were taken periodically for SEC analysis on a Superose 6 column, which eluted intact particles at 10 mL and capsid proteins at 20 mL. It was found that the CCMV-ODN1826 VLPs were stable under physiological conditions, with 90% of the particles remaining intact after 10 days (FIG. 2A). The wild-type CCMV particles were less stable than the VLPs under these conditions. Note that eCCMV is unstable under physiological conditions, and these particles were therefore not tested. CCMV-ODN1826 VLPs was treated with DNase I. There was no evidence of ODN digestion over 2 days, based on the unchanged A260/A280 ratio (FIG. 2B). This confirmed that the encapsulated ODNs are resistant to nuclease digestion.

Delivery of ODN1826 to Macrophages by VLPs

Figure 3A:
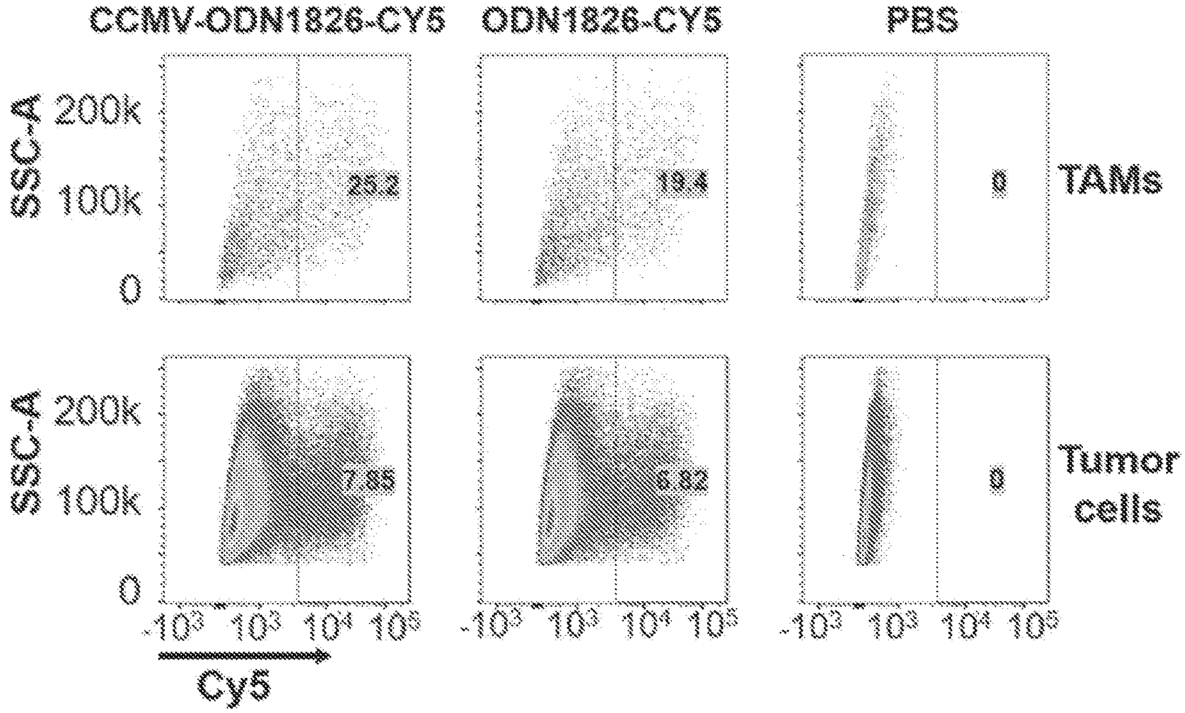
FIGS. 3A-3E illustrate internalization of ODN1826 and CCMV-ODN1826 by tumor cells and TAMs derived from single-cell suspensions of CT26 tumors.
Figure 3B:
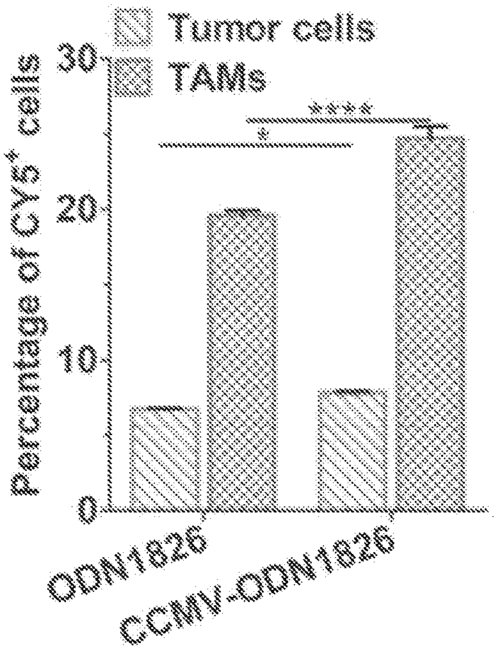
Figure 3C:
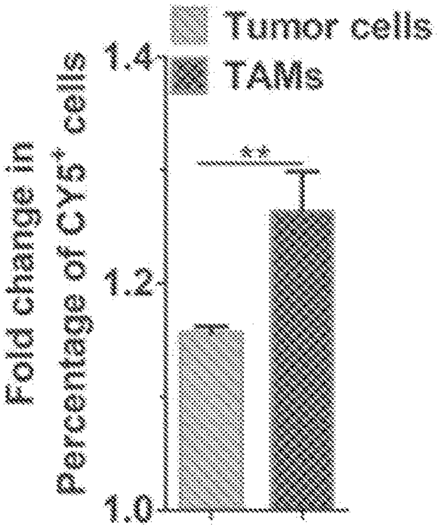
Figure 3D:
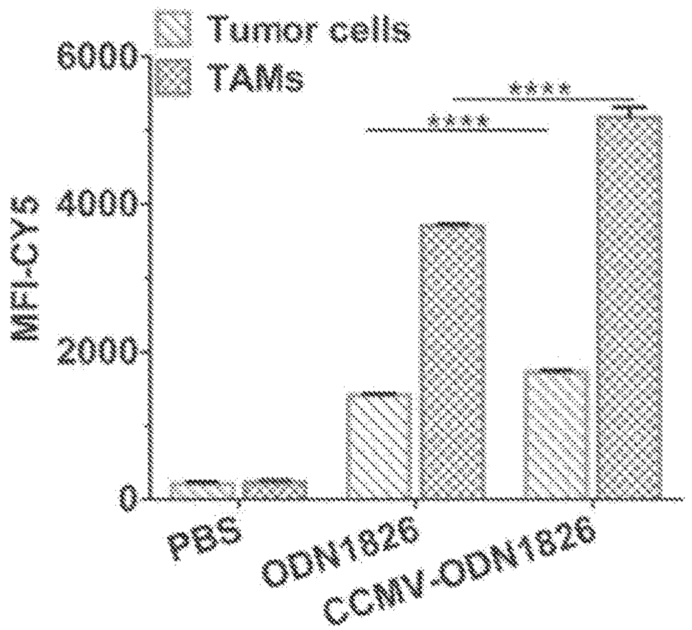
Figure 3E:
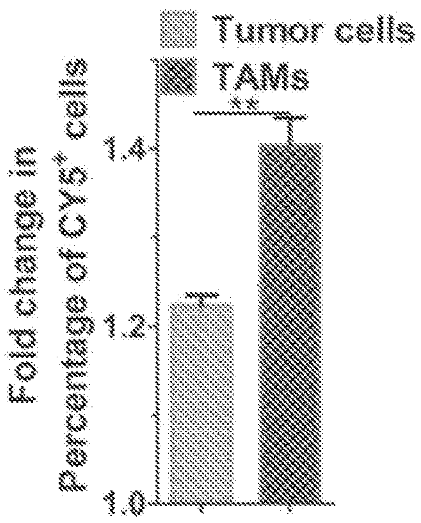

Next the up-take of CCMV-ODN VLPs by macrophages and cancer cells representing the TME was evaluated. ODN1826 labeled with cyanine 5 (CY5) was encapsulated during particle reassembly to prepare fluorescent VLPs (CCMV-ODN1826-CY5). Single-cell suspensions derived from murine subcutaneous colon cancer (CT26) were incubated with CCMV-ODN1826-CY5 particles or ODN1862-CY5 in its free form, then harvested and stained with fluorescent antibodies to differentiate TAMs and cancer cells prior to flow cytometry. As shown in FIG. 3A, both TAMs and tumor cells were able to take up CCMV-ODN1826-CY5 more efficiently than ODN1826-CY5. However, the encapsulation of ODN1826 increased the proportion of CY5-positive tumor cells from 6.8% to 7.8%, which is a non-significant change, but the proportion of CY5-positive TAMs increased significantly from 19% to 25% (FIG. 3A,B) resulting in a much higher fold-change in the number of CY5-positive TAMs compared to tumor cells (FIG. 3C). The mean fluorescence intensity (MFI) of the TAMs and tumor cells were also analyzed, and observed similar trends (FIG. 3D,E). Taken together, these data indicate that encapsulation significantly increases the uptake of ODNs by TAMs but not by tumor cells. This outcome indicates that the nanocarrier does not increase the uptake of CpG-ODNs by cancer cells. This is because CpG-ODNs activate immune cells and initiate antitumor responses, but if taken up by cancer cells they can also induce phosphoinositide 3-kinase (PI3K)/protein kinase B (Akt) signaling and therefore promote tumor progression.[39, 40]

In Vitro Activation of Macrophages

Figure 4A:
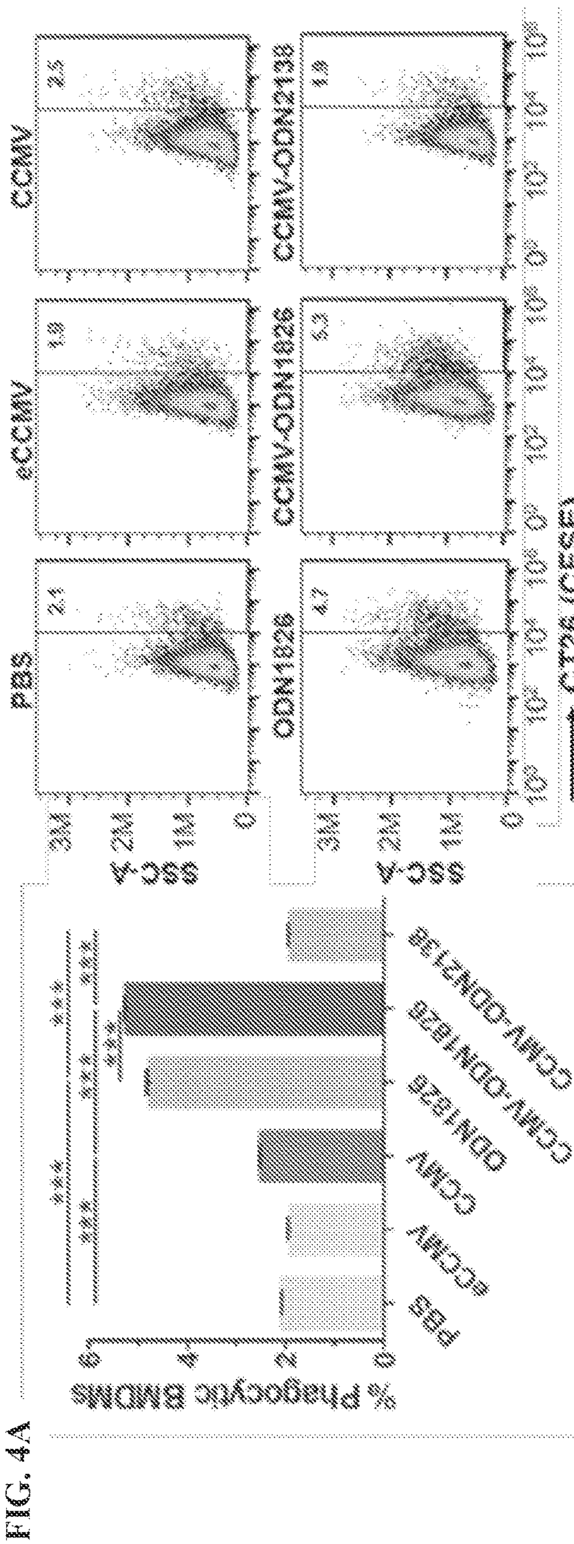
FIGS. 4A-4C illustrate activation of BMDMs by stimulation with ODNs and VLPs.

ODN1826 has been shown to increase the phagocytic activity of macrophages and thus enhance their effects against tumors.[36] Given the ability of CCMV-based VLPs to stabilize ODN1826 and promote its uptake specifically by macrophages in vitro, it was anticipated that CCMV-ODN1826 would activate macrophages and induce phagocytosis more efficiently than free ODN1826. To test this hypothesis in vitro, murine colon cancer CT26 cells were labeled with CFSE and co-cultured with bone-marrow derived macrophages (BMDMs). PBS, eCCMV, wild-type CCMV, free ODN1826, CCMV-ODN1826 or CCMV-ODN2138 was then added, the latter containing an inactive control ODN with the same properties as ODN1826 but with the CpG dinucleotides replaced by GpC. As expected, PBS, eCCMV, wild-type CCMV and CCMV-ODN2138 did not stimulate the BMDMs, whereas ODN1826 or CCMV-ODN1826 increased the number of BMDMs that attacked cancer cells and captured them by phagocytosis (FIG. 4A). The CCMV-ODN1826 treatment was much more efficacious than the free ODN1826 (FIG. 4A).

Figure 4B:
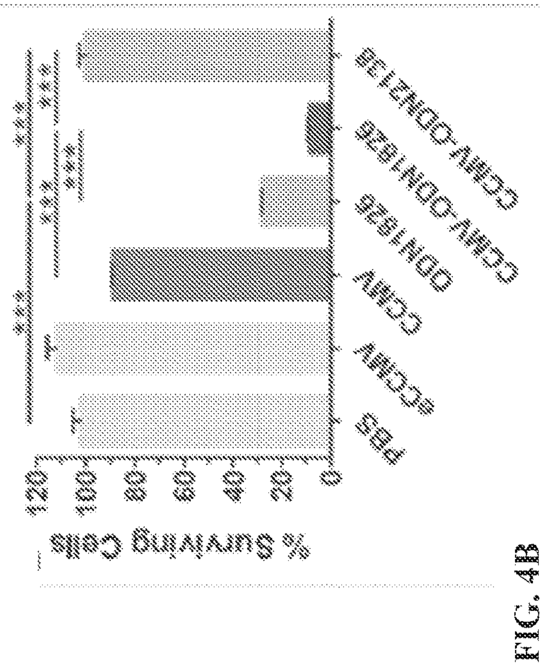

To determine whether the phagocytic capacity of the macrophages correlated with antitumor activity, BMDMs was co-cultured with luciferase-labeled CT26 (CT26-luc) cells and treated them with the same reagents listed above. Again, the control treatments did not have a significant effect on the number of surviving cancer cells, whereas both ODN1826 and CCMV-ODN1826 stimulated the antitumor activity of the BMDMs resulting in a decrease in tumor cell survival (FIG. 4B). As above, the efficacy of CCMV-ODN1826 was significantly greater than the free ODN1826 (FIG. 4B).

Figure 8A:
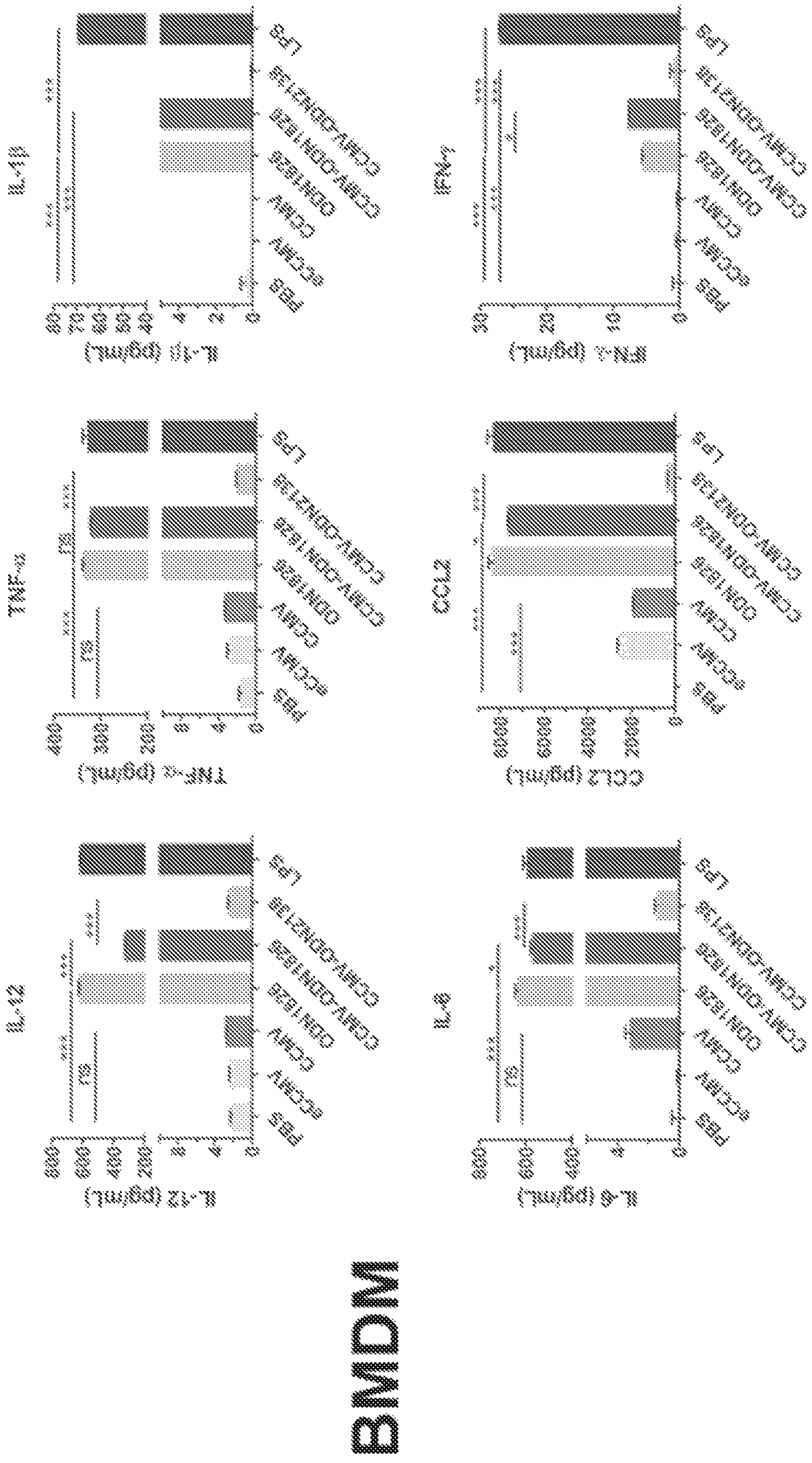
FIG. 8A illustrates the cytokine profiles after stimulating the BMDM with ODN1826 and CCMV VLPs.
Figure 8B:
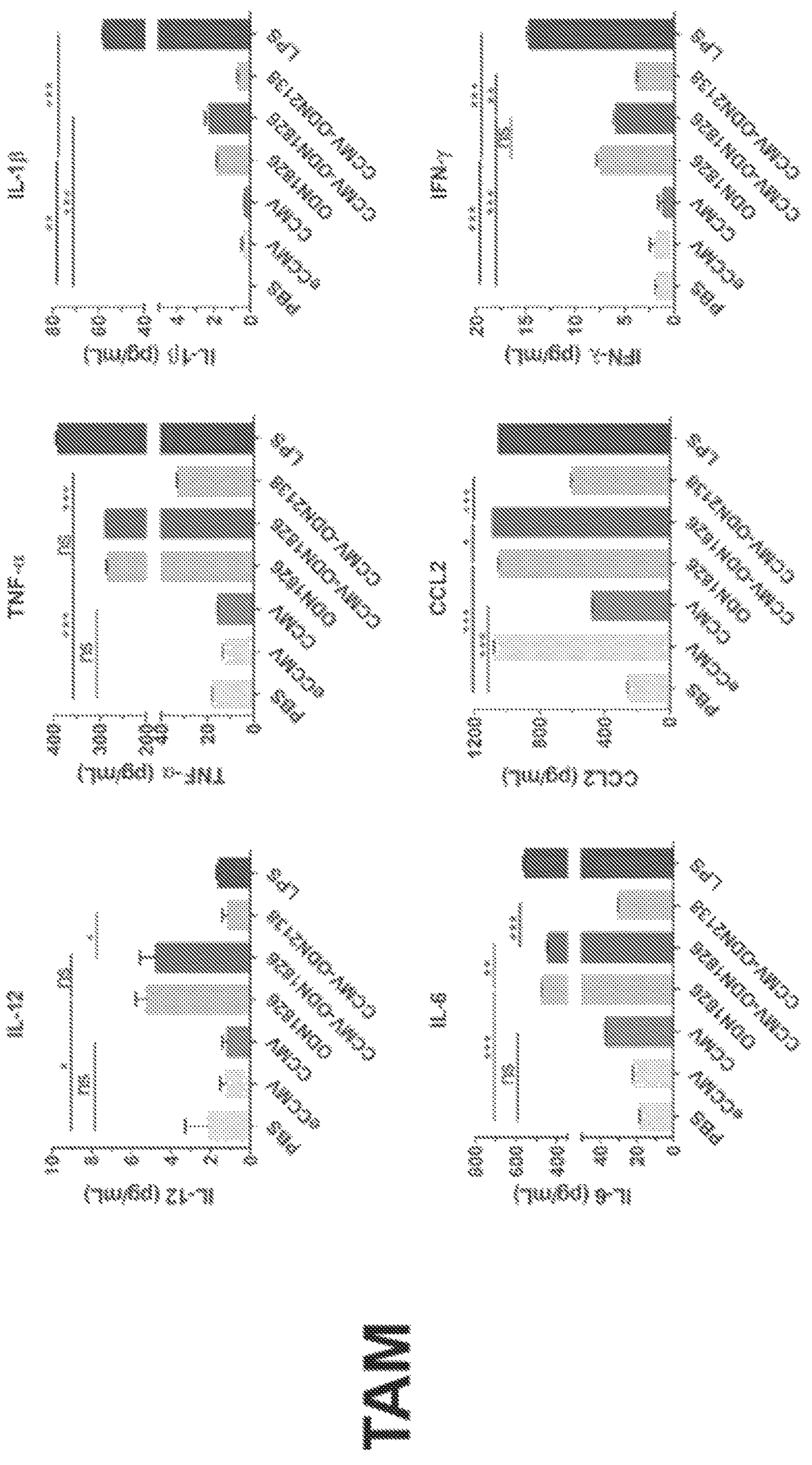
FIG. 8B illustrates the cytokine profiles after stimulating the TAM with ODN1826 and CCMV VLPs.
Figure 9:
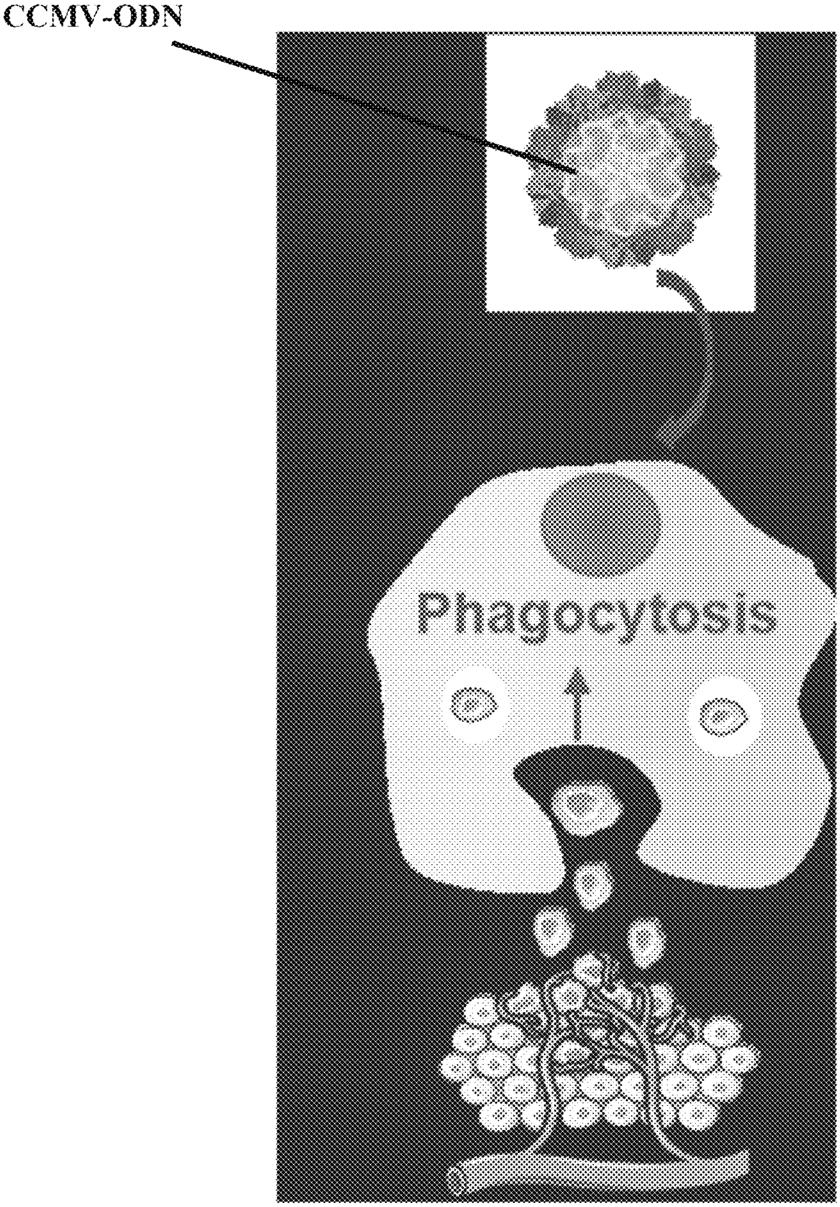
FIG. 9 illustrates a cartoon representation of a cell undergoing phagocytosis.

In addition to functions such as phagocytosis, immunostimulation often induces the secretion of cytokines, so the cytokine profile of BMDMs after stimulation with ODN1826 or CCMV-ODN1826 was also investigated. Both reagents increased the secretion of pro-inflammatory cytokines such as IL-12, TNF-α, IL-10, IL-6, CCL2 and IFN-λ (FIG. 8A-FIG. 8B). Interestingly, CCMV-ODN1826 induced the secretion of less IL-12, IL-6 and CCL2 but more IFN-λ than free ODN1826.

Figure 4C:
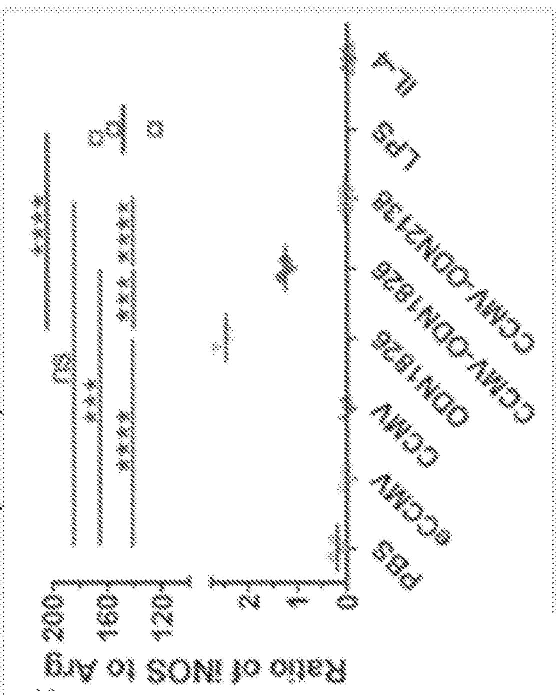

The cytokine profiles induced by ODN1826 and CCMV-ODN1826 were similar to those induced by lipopolysaccharides (LPS), which promote M1 polarization in macrophages and thus trigger pro-inflammatory and anti-tumor activity.[41] Immunotherapies that shift the polarization of TAMs toward the M1 phenotype have shown promising efficacy against cancer in preclinical models.[42, 43] BMDMs stimulated with ODN1826 or CCMV-ODN1826 was tested by flow cytometry for the presence of inducible nitric oxide synthase (iNOS), an M1 marker, and arginase 1 (Arg1), an M2 marker. LPS was used as a control for M1 polarization and IL4 as a control for M2 polarization, which suppresses inflammation and promotes tumor growth.[44] The ratio of iNOS/Arg reflected the balance of M1/M2 polarization, with LPS producing a high ratio and IL-4 producing a low ratio (FIG. 4C). The incubation of BMDMs with the control reagents (eCCMV, CCMV or CCMV-ODN2138) maintained the M2 polarity of the cells, whereas incubation with ODN1826 or CCMV-ODM1826 increased the iNOS/Arg ratio toward M1 polarization.

Figure 5A:
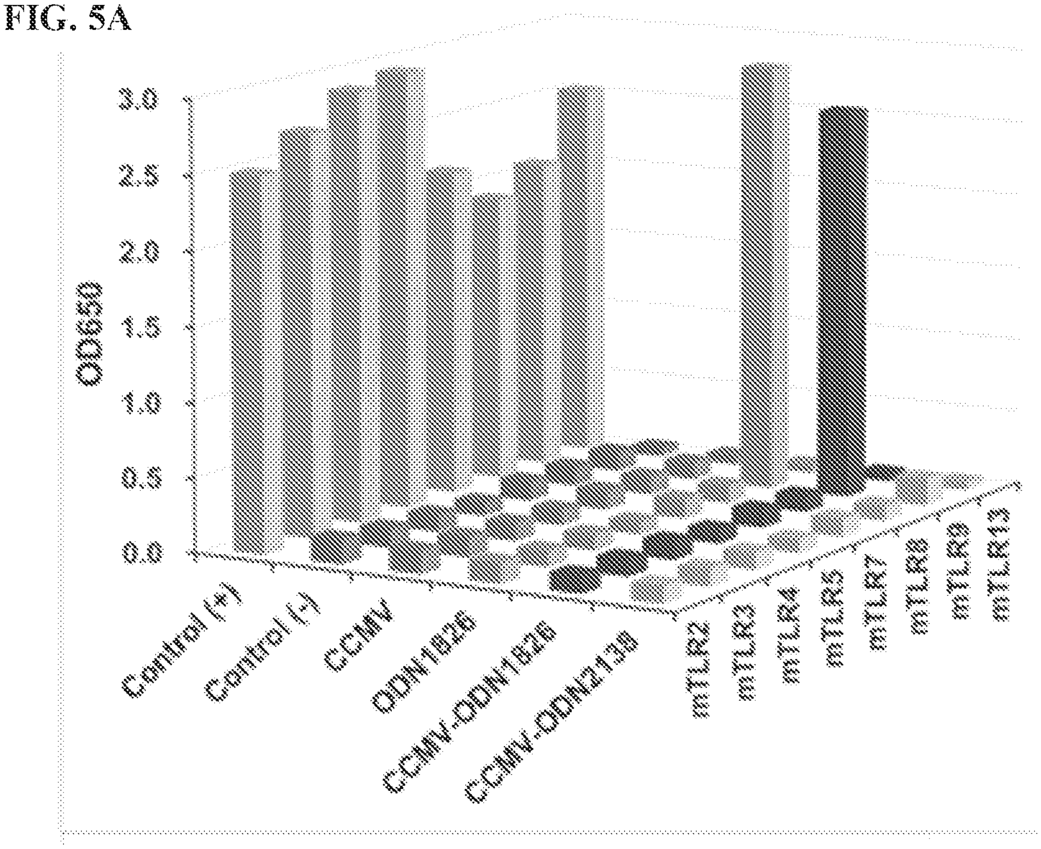
FIG. 5A illustrates NF-κB activation by stimulating HEK293 cells with free ODN1826, CCMV-ODN1826 or control VLPs (eCCMV, CCMV, or CCMV-ODN2138). Average of three independent experiments are shown.
Figure 5B:
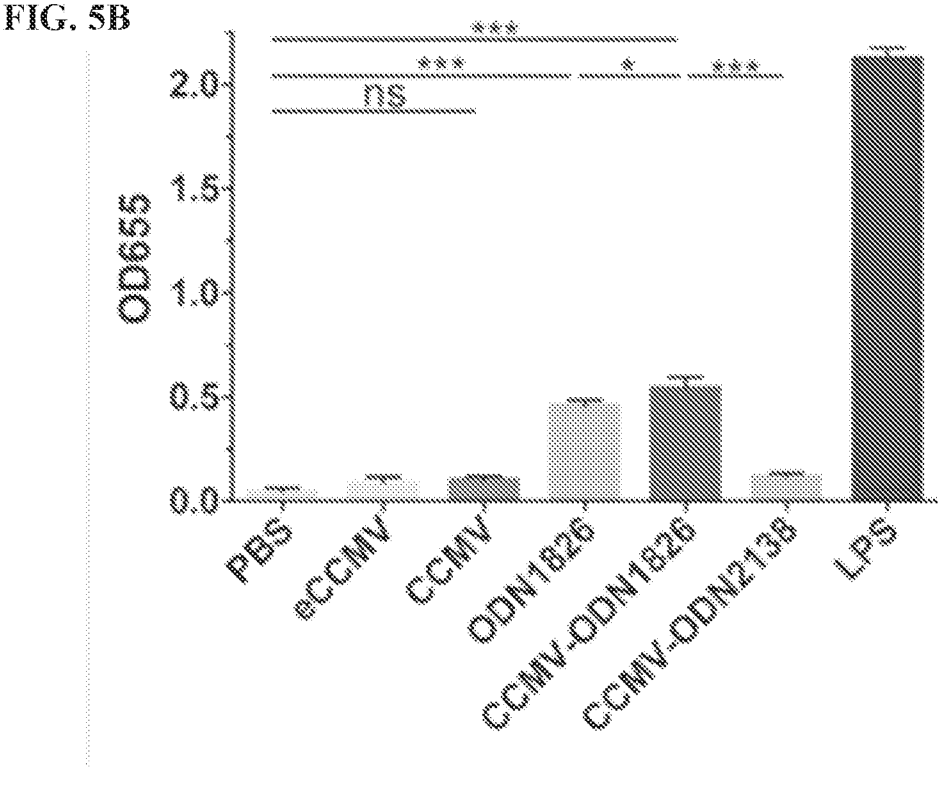
FIG. 5B shows stimulation of PRRs in RAW-Blue cells. RAW-Blue cells were stimulated with free ODN1826, CCMVODN1826 or control VLPs (eCCMV, CCMV, or CCMV-ODN2138). NF-κB or AP.1 activation was determined using QUANTI-Blue. Values are means±standard deviations (n=4). Statistical significance was determined by one-way ANOVA with Tukey's test: *p<0.05, p<0.01, *p<0.001.

Lastly, it was confirmed that ODN1826 and CCMV-ODN1826 activate and signal through TLR9; this was achieved by assessing NF-κB activation in HEK293 cells expressing a given TLRs (TLR2, 3, 4, 5, 7, 8, 9 and 13) (FIG. 5A). Both ODN1826 and CCMV-ODN1826 activated the TLR9 at the same level, but no activation to the other TLRs was observed (FIG. 5A). Neither wild-type CCMV nor CCMV-ODN2138 showed any TLR activation, consistent with the assayed antitumor activities of these VLPs and incubated in co-culture of BMDMs and tumor cells (see FIG. 4). To validate these observations, activation of RAW-Blue cells was assayed by incubation with CCMV-ODN and controls. RAW-Blue cells express many pattern recognition receptors (PRRs), TLRs, NOD-like receptors, RIG-I-like receptors, and type lectin receptors. Similar to the assays performed using the HEK293 cells, NF-κB and AP.1 activation is assayed to determine whether activation of any of the PRRs is achieved (the assay does not differentiate which pathways are activated). Similar to the results of TLRs activation using the HEK293 cells (FIG. 5A), only stimulation using ODN1826 or CCMV-ODN1826 led to signaling in RAW-Blue cells (FIG. 5B). Together, these data confirm that ODN1826 in free form or encapsulated in CCMV is effective to activate PRRs and signals through TLR9.

In Vivo Antitumor Activity

Figure 6A:
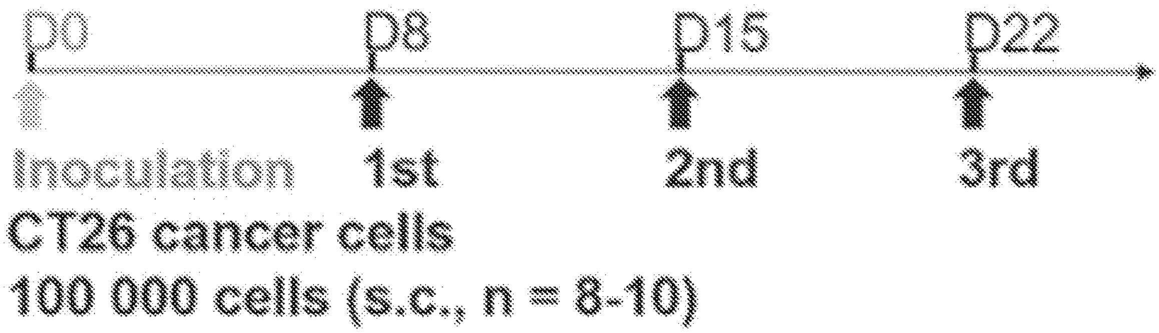
FIGS. 6A-6F illustrate in vivo antitumor efficacy of free ODN1826, CCMV-ODN1826 and control VLPs in a murine model of colon cancer.

Finally, it was investigated whether the in vitro results described above could be replicated in vivo, using the CT26 murine colon cancer model. CT26 cells were subcutaneously (s.c.) inoculated into the right flank of BALB/c mice, and tumor-bearing mice were randomized to one of six treatment groups: i) PBS, ii) eCCMV, iii) wild-type CCMV, iv) CCMV-ODN2138 (negative control), v) ODN1826, and vi) CCMV-ODN1826. All reagents were delivered intratumorally (i.t.) at doses of 100 μg for the VLPs or 10 μg for the free ODN per injection. Treatments were started when the tumor volume reached 30-50 $mm^3$, and three treatments were administered in total at weekly intervals (FIG. 6A). Wild-type CCMV, eCCMV and CCMV-ODN2138 showed no efficacy against CT26 tumors, as shown by the tumor growth curves (FIGS. 6B and C) and survival data (FIG. 6D), which were similar to the PBS group. Treatment with free ODN1826 slowed tumor growth (50% drop in the day 26 mean normalized tumor volume compared to the PBS group) and prolonged median survival from 26 days in the PBS group to 31 days. However, treatment with CCMV-ODN1826 was much more efficacious, significantly inhibiting tumor growth (80% drop in the day 26 mean normalized tumor volume compared to the PBS group) and significantly prolonging median survival from 26 days to 42 days.

Figure 6B:
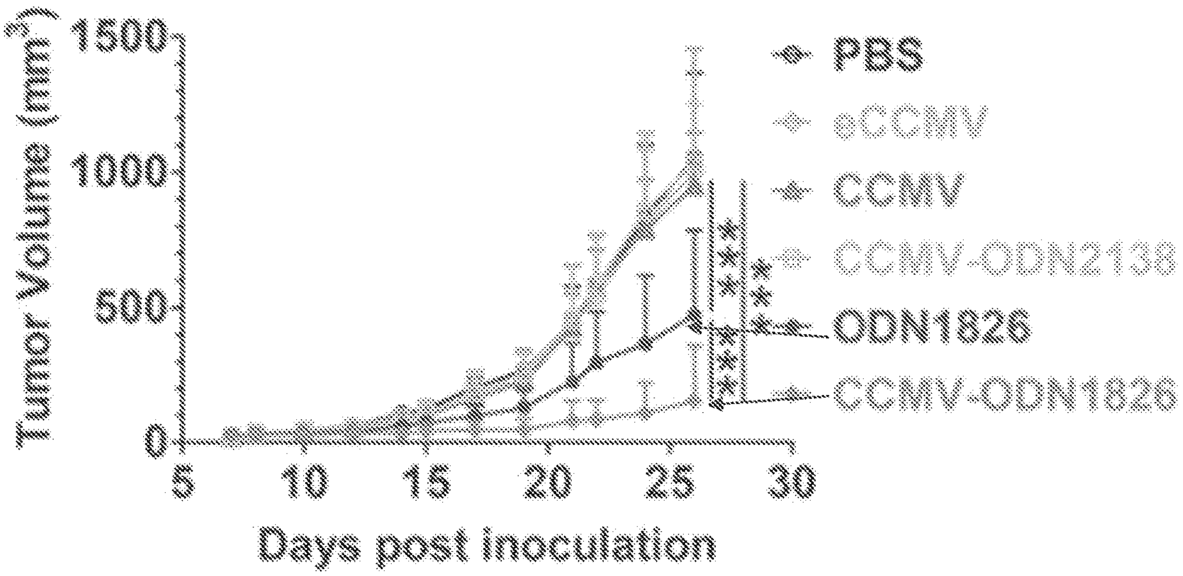
Figure 6C:
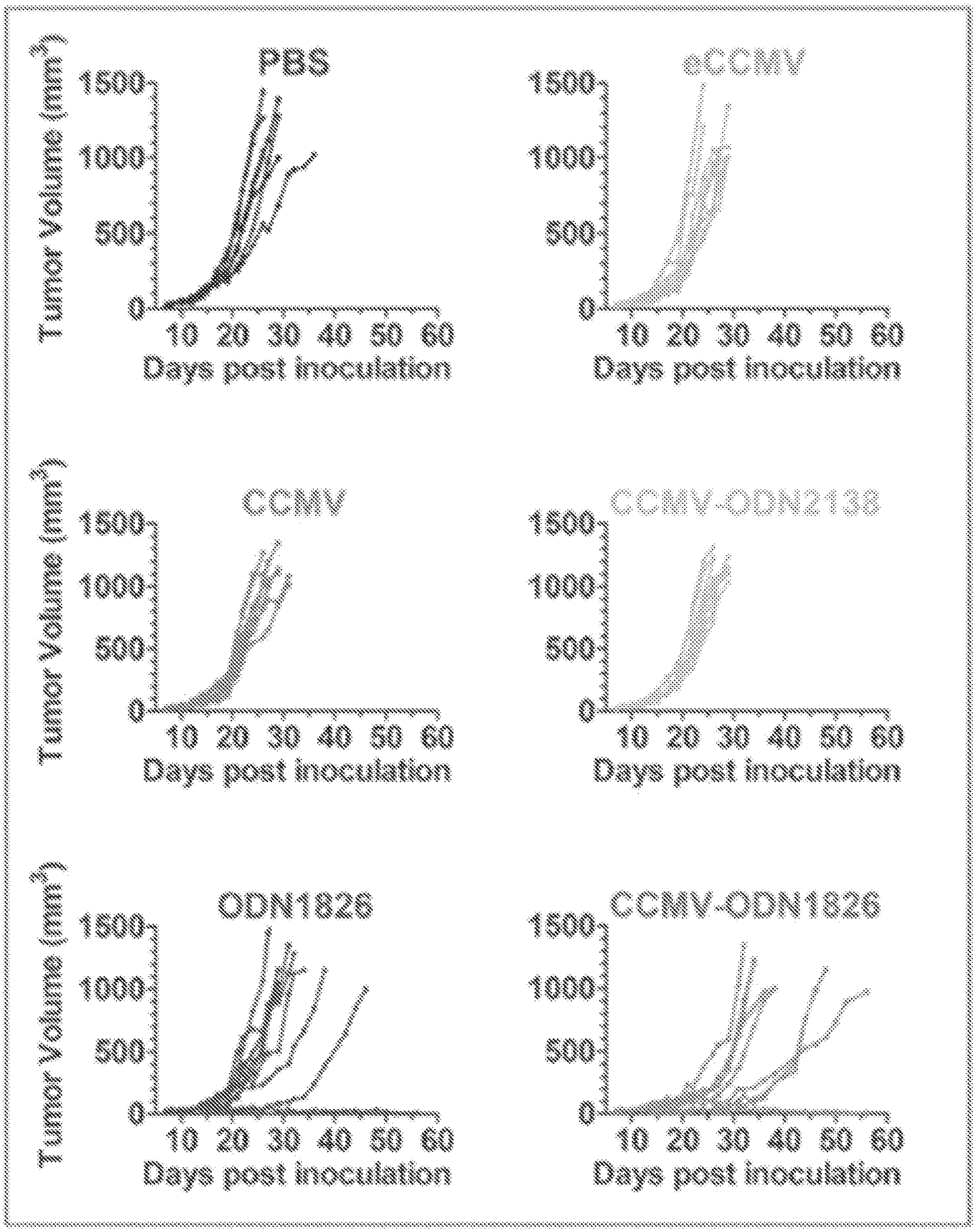
Figure 6D:
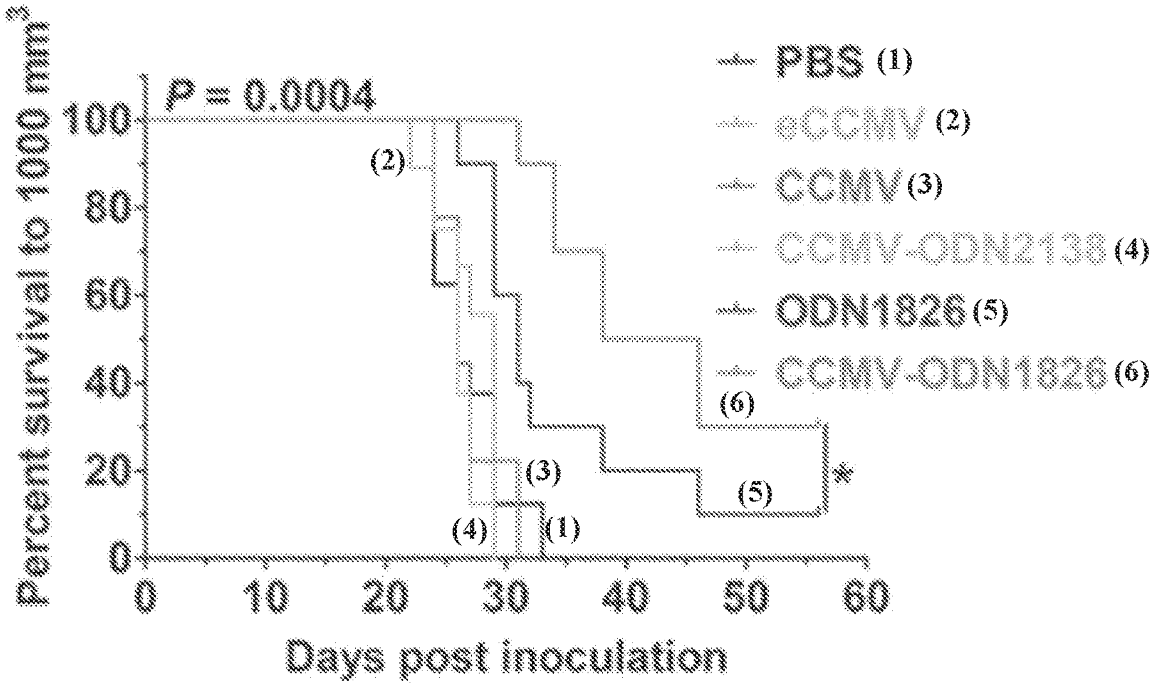
Figure 6E:
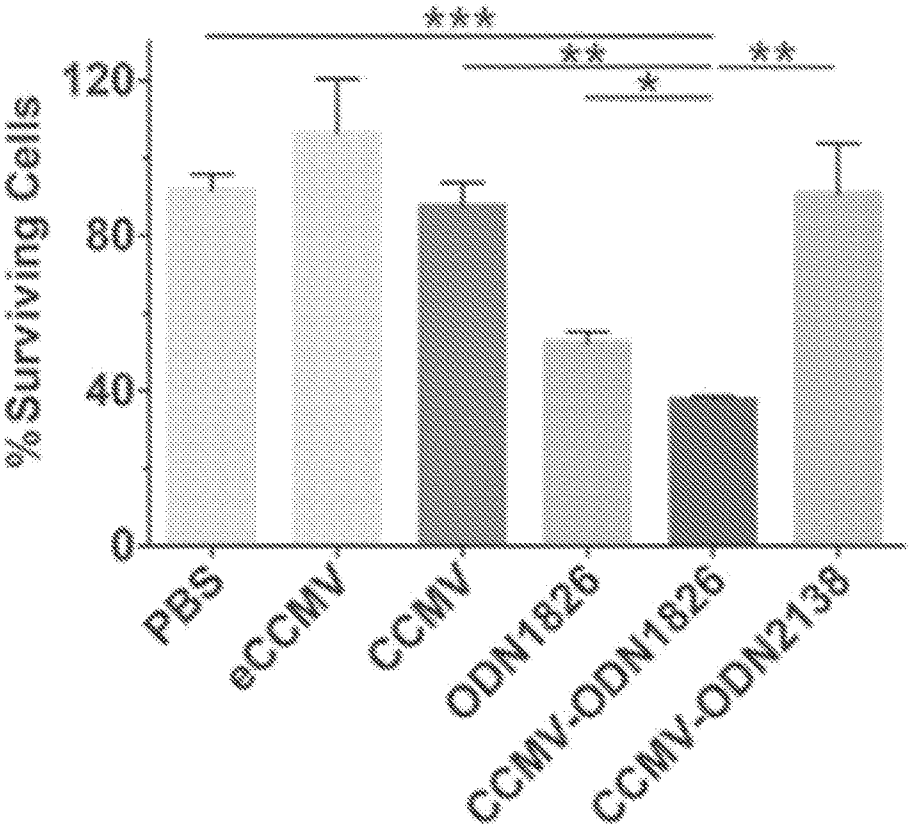
Figure 6F:
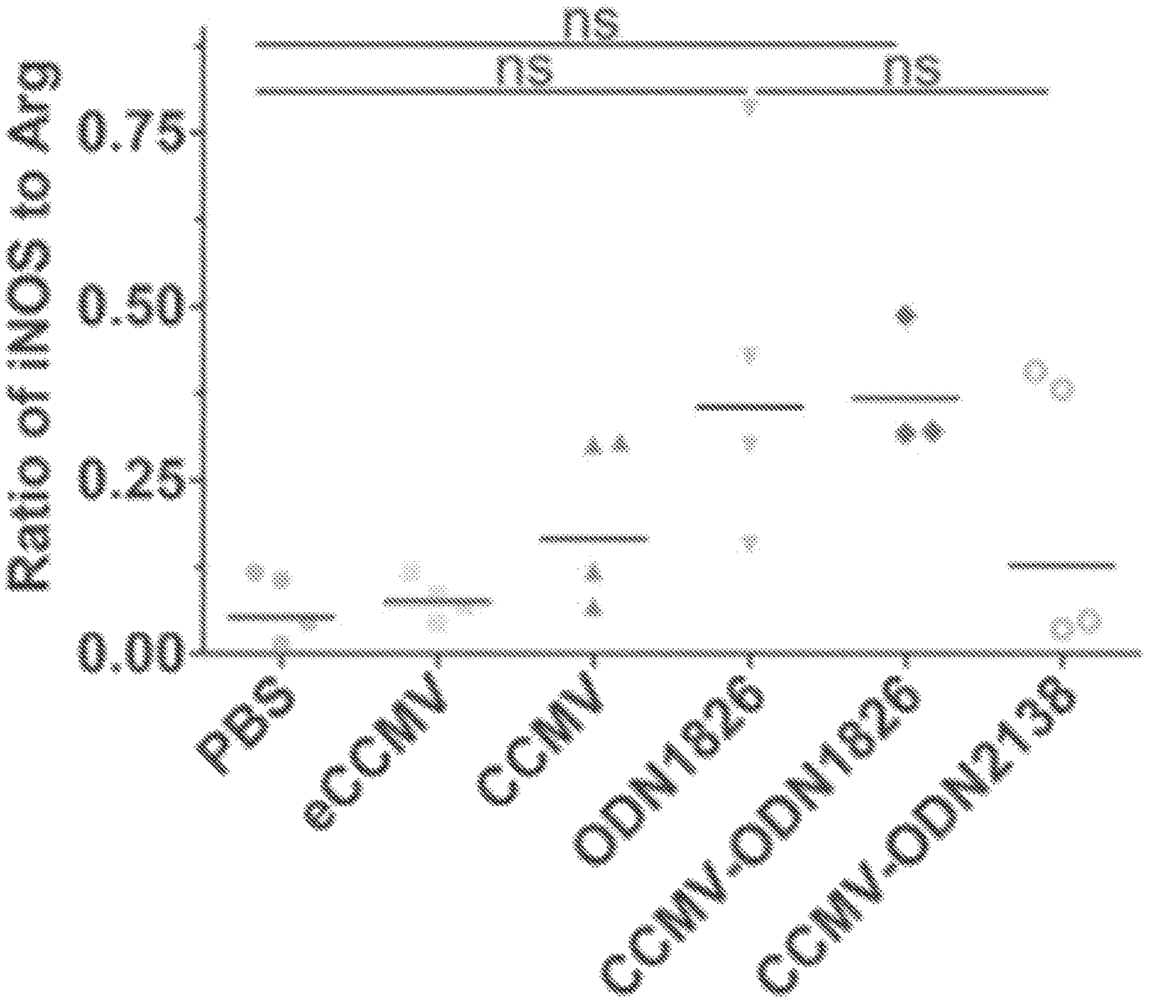

To confirm whether ODN1826 increased the phagocytic capacity of TAMs, the TAMs was isolated from the CT26 tumors and co-cultured them ex vivo with CT26-luc cells. The results (FIG. 6E) were similar to those reported above for the BMDM cells (FIG. 4B). Free ODN1826 stimulated moderate phagocytic activity, whereas CCMV-ODN1826 stimulated substantial phagocytic activity. The ex vivo phagocytic capacity of the TAMs correlated with the tumor growth curves (FIG. 6B, E). Cytokine secretion by the TAMs was monitored and it was found that ODN1826 and CCMV-ODN1826 induced the same palette of pro-inflammatory cytokines reported above for BMDMs (FIG. 8A and FIG. 8B). M1/M2 polarization in the TME was also evaluated following the treatment of CT26 tumor-bearing mice on day 12 with free ODN1826, CCMV-ODN1826 and the panel of control VLPs. Tumors were harvested after 24 h and single-cell suspensions were prepared. The iNOS/Arg ratio was measured by flow cytometry, and again the results with ex vivo TAMs (FIG. 6F) were similar to those reported above for BMDMs (FIG. 4F), with both free ODN1826 and CCMV-ODN1826 triggering a slight increase in the iNOS/Arg ratio indicating polarization toward M1. However, the magnitude of the response was not as high as that observed for the BMDMs.

Figure 7A:
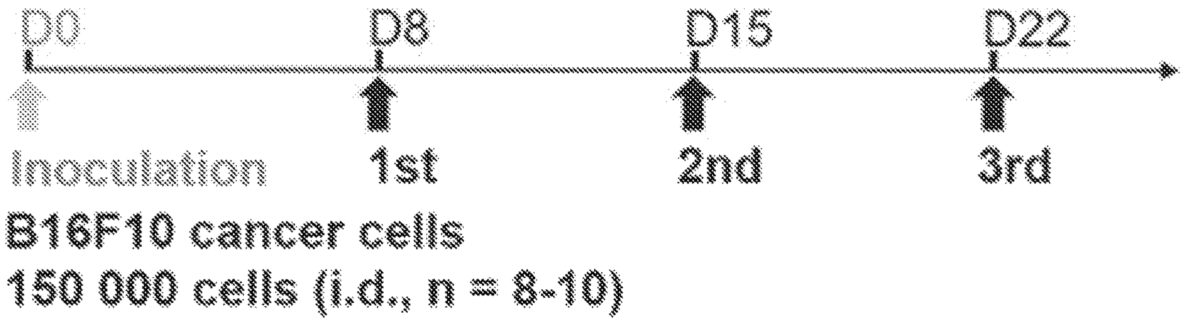
FIGS. 7A-7D illustrate in vivo antitumor efficacy of free ODN1826, CCMV-ODN1826 and control VLPs in a murine model of melanoma.
Figure 7B:
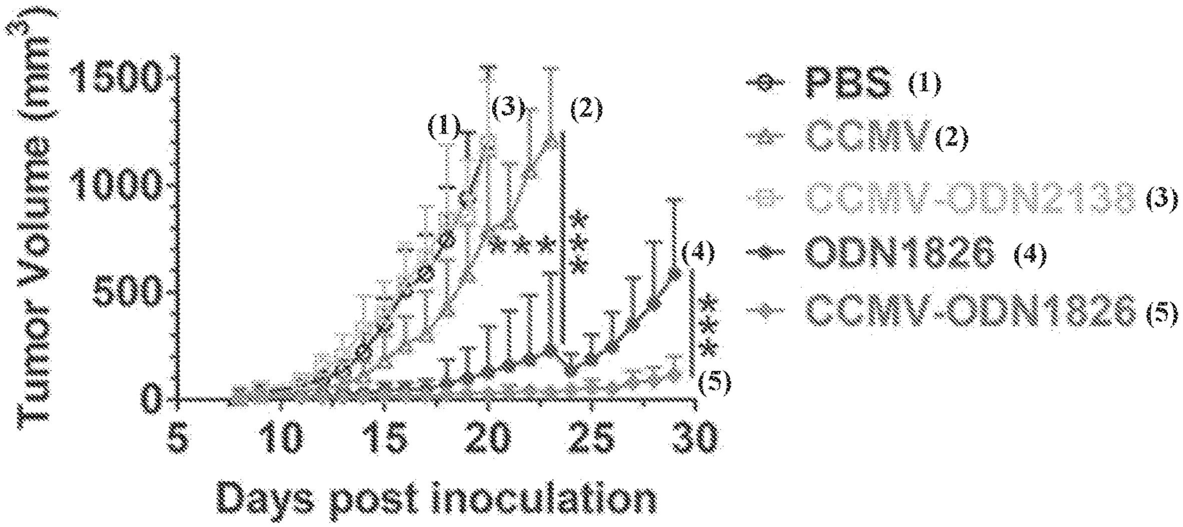
Figure 7C:
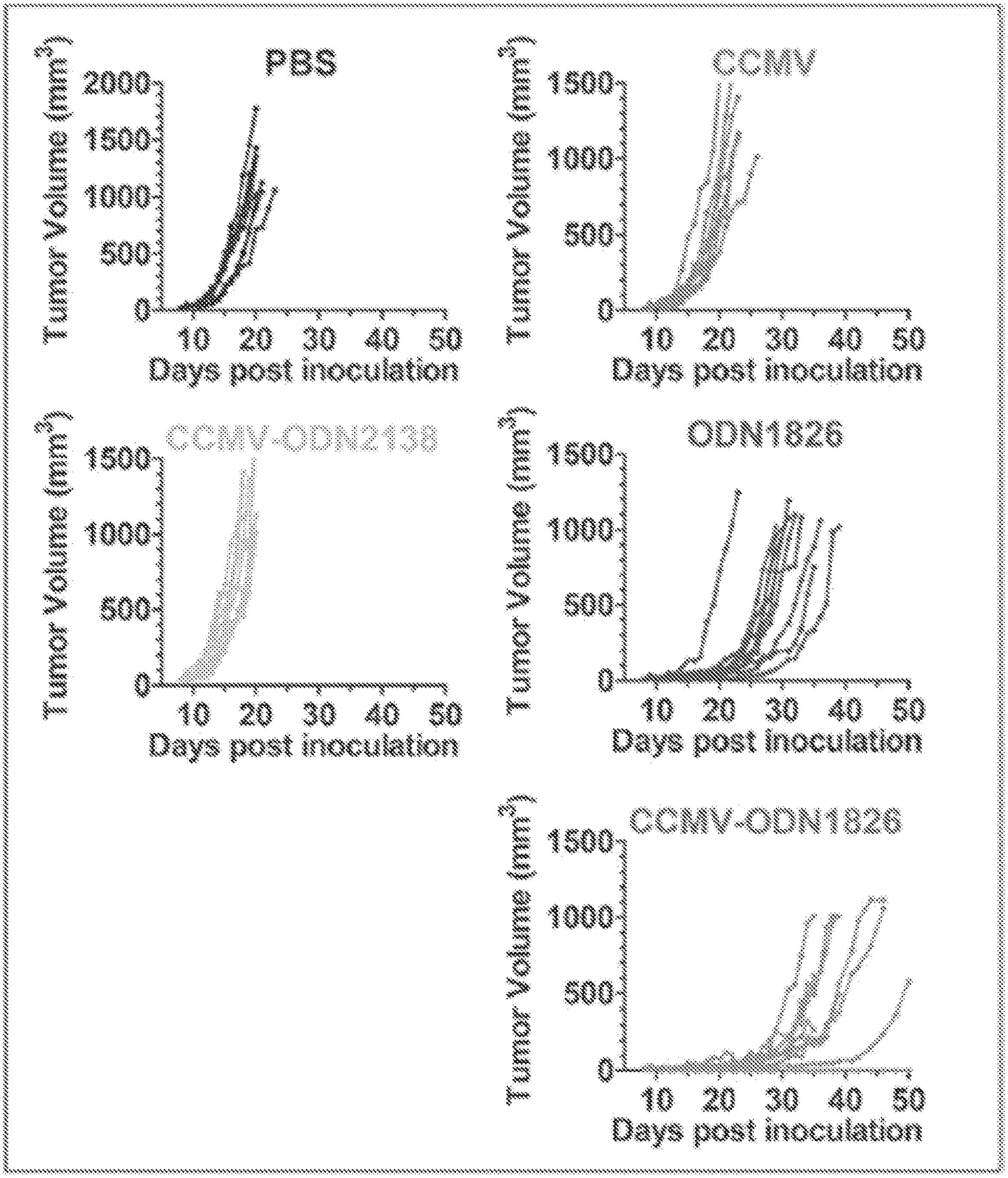
Figure 7D:
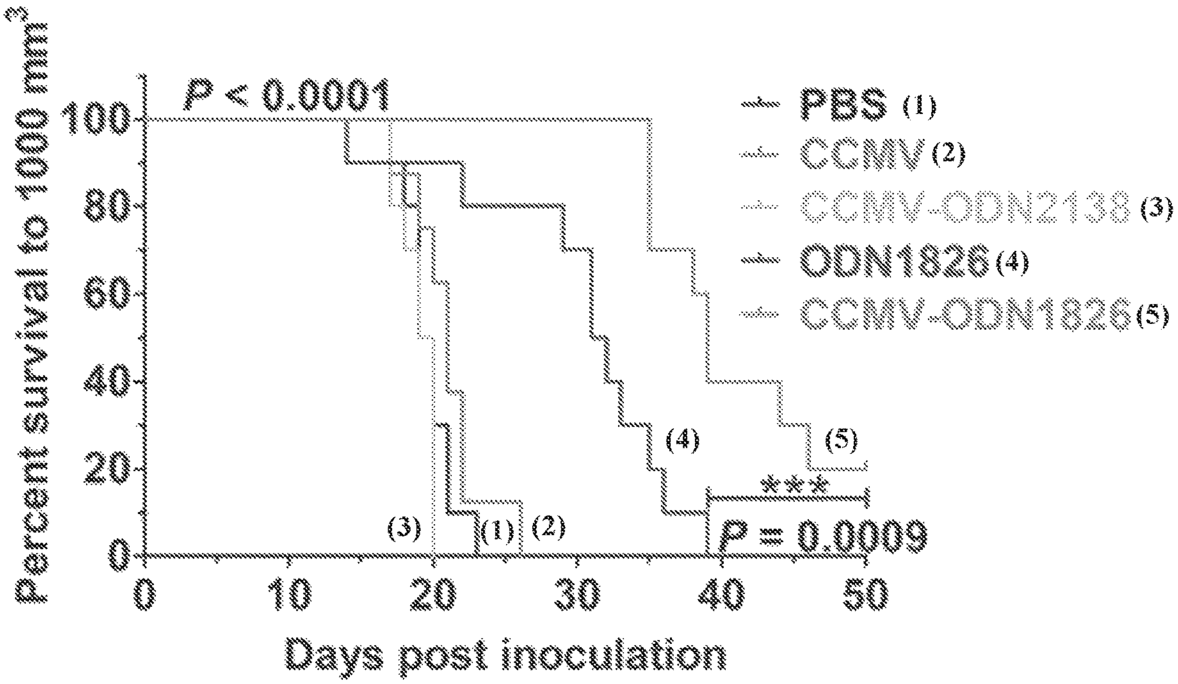

To determine whether CCMV-ODN1826 can enhance the in vivo antitumor activity of macrophages in other tumor models, a second study was carried out using the B16F10 murine melanoma model. B16F10 cancer cells were inoculated intradermally (i.d.). Tumor-bearing mice were treated with free ODN1826, CCMV-ODN1826 or the control VLPs listed above (except eCCMV) following the same schedule as the CT26 tumor model (FIG. 7A). Unlike the CT26 model, treatment with wild-type CCMV showed some efficacy against B16F10 melanoma, resulting in slower tumor growth than the PBS treatment and CCMV-ODN2138 control (FIGS. 7B and C), but there was no significant extension of survival (FIG. 7D). Both free ODN1826 and CCMV-ODN1826 showed efficacy in the melanoma model, but the CCMV-ODN1826 treatment was much more efficacious (80% drop in the day 28 mean normalized tumor volume compared to the free ODN1826 group). Encapsulation of the ODN also prolonged survival, with the ODN1826 group showing a median survival of 31 days but the CCMV-ODN1826 group extending that to 39 days. The greater in vivo anti-tumor efficacy achieved by the encapsulation of ODN1826 for the treatment of melanoma was therefore consistent with that in colon cancer.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

Embodiments

Embodiment 1: An engineered virus-like particle (VLP) comprising, or consisting essentially of, or yet further consisting of, an oligodeoxynucleotide (ODN) having less than 100 nucleotides encapsulated within the VLP, is the ODN being optionally resistant to nuclease digestion. In some embodiments, the ODN is less than or about 30 nucleotides. In some cases, the ODN is less than or about 29 nucleotides. In some cases, the ODN is less than or about 28 nucleotides. In some cases, the ODN is less than or about 27 nucleotides. In some cases, the ODN is less than or about 26 nucleotides. In some cases, the ODN is less than or about 25 nucleotides. In some cases, the ODN is less than or about 24 nucleotides. In some cases, the ODN is less than or about 23 nucleotides. In some cases, the ODN is less than or about 22 nucleotides. In some cases, the ODN is less than or about 21 nucleotides. In some cases, the ODN is less than or about 20 nucleotides. In some cases, the ODN is less than or about 19 nucleotides. In some cases, the ODN is less than or about 18 nucleotides. In some cases, the ODN is less than or about 17 nucleotides. In some cases, the ODN is less than or about 16 nucleotides. In some cases, the ODN is less than or about 15 nucleotides. Alternatively, in some cases, the ODN is at least 10 nucleotides but no more than 100, 99, 95, or 90 nucleotides. In some cases, the ODN is at least 15 nucleotides. In some cases, the ODN is at least 18 nucleotides. In some cases, the ODN is at least 20 nucleotides. In some cases, the ODN is at least 23 nucleotides. In some cases, the ODN is at least 25 nucleotides. In some cases, the ODN is at least 28 nucleotides. In some cases, the ODN is at least 30 nucleotides. In some cases, the ODN is at least 35 nucleotides. In some cases, the ODN is at least 40 nucleotides. In some cases, the ODN is at least 50 nucleotides. In some cases, the ODN is at least 60 nucleotides. In some cases, the ODN is at least 70 nucleotides. In some cases, the ODN is at least 80 nucleotides.

Embodiment 2: The engineered VLP of embodiment 1, wherein the ODN is a CpG-containing ODN (CpG ODN).

Embodiment 3: The engineered VLP of embodiment 2, wherein the CpG ODN is a Class A (Type D) ODN.

Embodiment 4: The engineered VLP of embodiment 2, wherein the CpG ODN is a Class B (Type K) ODN.

Embodiment 5: The engineered VLP of embodiment 2, wherein the CpG ODN is a Class C ODN.

Embodiment 6: The engineered VLP of embodiment 2, wherein the CpG ODN is a Class P ODN.

Embodiment 7: The engineered VLP of embodiment 2, wherein the CpG ODN is a Class S ODN.

Embodiment 8: The engineered VLP of any one of the embodiments 1-7, wherein the ODN is less than or about 90 nucleotides, less than or about 80 nucleotides, less than or about 70 nucleotides, less than or about 60 nucleotides, less than or about 50 nucleotides, less than or about 40 nucleotides, less than or about 35 nucleotides, less than or about 30 nucleotides, less than or about 28 nucleotides, less than or about 25 nucleotides, less than or about 23 nucleotides, less than or about 20 nucleotides, less than or about 18 nucleotides, less than or about 15 nucleotides, or less than or about 10 nucleotides.

Embodiment 9: The engineered VLP of any one of the embodiments 1-8, wherein the ODN is less than or about 30 nucleotides, less than or about 29 nucleotides, less than or about 28 nucleotides, less than or about 27 nucleotides, less than or about 26 nucleotides, less than or about 25 nucleotides, less than or about 24 nucleotides, less than or about 23 nucleotides, less than or about 22 nucleotides, less than or about 21 nucleotides, less than or about 20 nucleotides, less than or about 19 nucleotides, less than or about 18 nucleotides, less than or about 17 nucleotides, less than or about 16 nucleotides, or less than or about 15 nucleotides.

Embodiment 10: The engineered VLP of any one of the embodiments 1-7, wherein the ODN is at least 10 nucleotides, at least 15 nucleotides, at least 18 nucleotides, at least 20 nucleotides, at least 23 nucleotides, at least 25 nucleotides, at least 28 nucleotides, at least 30 nucleotides, at least 35 nucleotides, at least 40 nucleotides, at least 50 nucleotides, at least 60 nucleotides, at least 70 nucleotides, or at least 80 nucleotides and no more than about 90, 95, or 99 nucleotides.

Embodiment 11: The engineered VLP of any one of the embodiments 1-7 or 10, wherein the ODN is at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, or at least 30 nucleotides and no more than about 90, 95, or 99 nucleotides.

Embodiment 12: The engineered VLP of any one of the embodiments 1-7, wherein the ODN is from about 15 nucleotides to about 30 nucleotides, from about 15 nucleotides to about 28 nucleotides, from about 15 nucleotides to about 25 nucleotides, from about 15 nucleotides to about 20 nucleotides, from about 18 nucleotides to about 30 nucleotides, from about 18 nucleotides to about 28 nucleotides, from about 18 nucleotides to about 25 nucleotides, from about 18 nucleotides to about 20 nucleotides, from about 20 nucleotides to about 30 nucleotides, from about 20 nucleotides to about 28 nucleotides, or from about 20 nucleotides to about 25 nucleotides in length.

Embodiment 13: The engineered VLP of any one of the embodiments 1-12, wherein the CpG ODN comprise, or consists essentially of, or yet further consists of, s an ODN illustrated in Table 1 or an equivalent thereof.

Embodiment 14: The engineered VLP of any one of the embodiments 1-12, wherein the CpG ODN comprises, or consists essentially of, or yet further consists of, an ODN illustrated in Table 2 or an equivalent thereof.

Embodiment 15: The engineered VLP of any one of the embodiments 1-12, wherein the CpG ODN is an ODN illustrated in Table 1.

Embodiment 16: The engineered VLP of any one of the embodiments 1-12, wherein the CpG ODN is an ODN illustrated in Table 2.

Embodiment 17: The engineered VLP of any one of the embodiments 1-16, wherein the ODN comprises, or consists essentially of, or yet further consists of, or consist of ODN1826.

Embodiment 18: The engineered VLP of any one of the embodiments 1-17, wherein the ODN comprises, or consists essentially of, or yet further consists of, at least one modified internucleotide linkage.

Embodiment 19: The engineered VLP of embodiment 18, wherein the at least one modified internucleotide linkage comprise, or consists essentially of, or yet further consists of, s a phosphorothioate linkage or a phosphorodithioate linkage.

Embodiment 20: The engineered VLP of any one of the embodiments 1-19, wherein the ODN comprises, or consists essentially of, or yet further consists of, at least one 2' modified nucleotide.

Embodiment 21: The engineered VLP of embodiment 20, wherein the at least one 2' modified nucleotide comprise, or consists essentially of, or yet further consists of, s 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethyl-aminopropyl (2'-O-DMAP), 2'-O-dimethylaminoethyloxy-ethyl (2'-O-DMAEOE), or 2'-O—N-methylacetamido (2'-O-NMA) modified nucleotide.

Embodiment 22: The engineered VLP of embodiment 20, wherein the at least one 2' modified nucleotide comprises, or consists essentially of, or yet further consists of, locked nucleic acid (LNA) or ethylene nucleic acid (ENA).

Embodiment 23: The engineered VLP of any one of the embodiments 1-22, wherein the VLP is derived from a plant virus.

Embodiment 24: The engineered VLP of embodiment 23, wherein the plant virus is from the genus *Bromovirus, Comovirus*, or *Tymovirus*.

Embodiment 25: The engineered VLP of embodiment 23 or 24, wherein the plant virus is Cowpea chlorotic mottle virus (CCMV).

Embodiment 26: The engineered VLP of embodiment 23 or 24, wherein the plant virus is Cowpea mosaic virus (CPMV).

Embodiment 27: The engineered VLP of embodiment 23 or 24, wherein the plant virus is Physalis mottle virus (PhMV).

Embodiment 28: The engineered VLP of any one of the embodiments 1-27, wherein the VLP comprises, or consists essentially of, or yet further consists of, a capsid protein, optionally a modified capsid protein, further optionally from CCMV, CPMV, PhMV, or a combination thereof.

Embodiment 29: The engineered VLP of any one of the embodiments 1-28, wherein the VLP comprises, or consists essentially of, or yet further consists of, an extracellular or transmembrane polypeptide that specifically binds to a receptor expressed on a target cell, optionally an immune cell.

Embodiment 30: The engineered VLP of embodiment 29, wherein the immune cell is an antigen presenting cell.

Embodiment 31: The engineered VLP of embodiment 29 or 31, wherein the immune cell is a macrophage, B cell, or dendritic cell.

Embodiment 32: The engineered VLP of embodiment 29, wherein the immune cell is a nature killer (NK) cell.

Embodiment 33: The engineered VLP of any one of the embodiments 29, 31, or 32, wherein the macrophage is a tumor-associated macrophage (TAM).

Embodiment 34: The engineered VLP of any one of the embodiments 29, 31, 32, or 33, wherein the macrophage, optionally TAM, is located within a tumor microenvironment (TME).

Embodiment 35: The engineered VLP of any one of the embodiments 1-34, wherein the VLP increases uptake of the ODN in a macrophage, optionally a TAM, compared to an uptake rate of an ODN by the macrophage, optionally the TAM, not encapsulated by the engineered VLP.

Embodiment 36: The engineered VLP of embodiment 35, wherein the increased uptake is by at least 1-fold, 2-fold, 3-fold, 4-fold, 5-fold, 6-fold, 7-fold, 8-fold, 9-fold, 10-fold, 20 fold, 30-fold, 50-fold, 100-fold, or more.

Embodiment 37: The engineered VLP of embodiment 35, wherein the increased uptake is by at least 10%, 15%, 20%, 25%, 30%, 40%, 50%, 60%, 70%, 80%, 90%, 100%, or more.

Embodiment 38: The engineered VLP of any one of the embodiments 1-37, wherein the VLP modulates activation of phagocytosis in the immune cell, optionally the macrophage.

Embodiment 39: The engineered VLP of any one of the embodiments 1-38, wherein the VLP modulates polarization of the macrophage toward a M1 phenotype.

Embodiment 40: The engineered VLP of any one of the embodiments 1-39, wherein the VLP modulates secretion of a cytokine from the immune cell, optionally the macrophage, thereby to induce an immunostimulation.

Embodiment 41: The engineered VLP of embodiment 40, wherein the cytokine is a pro-inflammatory cytokine.

Embodiment 42: The engineered VLP of embodiment 40 or 41, wherein the cytokine is TNFα, IFNγ, IL-1, IL-12, IL-18, or GM-CSF.

Embodiment 43: The engineered VLP of any one of embodiments 1-42, further comprising, or consisting essentially of, or yet further consisting of, an additional therapeutic agent encapsulated within the VLP.

Embodiment 44: The engineered VLP of embodiment 43, wherein the additional therapeutic agent is an agent for a cancer therapy.

Embodiment 45: The engineered VLP of embodiment 43 or 44, wherein the additional therapeutic agent comprises, or consists essentially of, or yet further consists of, chemotherapeutic agent, an immunotherapeutic agent, a targeted therapy, radiation therapy, or a combination thereof.

Embodiment 46: The engineered VLP of any one of the embodiments 43-45, wherein the additional therapeutic agent comprises, or consists essentially of, or yet further consists of, a cancer immunotherapeutic agent.

Embodiment 47: The engineered VLP of any one of the embodiments 43-46, wherein the additional therapeutic agent comprises, or consists essentially of, or yet further consists of, a checkpoint inhibitor.

Embodiment 48: The engineered VLP of any one of the embodiments 43-47, wherein the additional therapeutic agent comprises, or consists essentially of, or yet further consists of, pembrolizumab, nivolumab, tremelimumab, or ipilimumab.

Embodiment 49: The engineered VLP of any one of the embodiments 43-47, wherein the additional therapeutic agent comprises, or consists essentially of, or yet further consists of, alemtuzumab, trastuzumab, ibritumomab tiuxetan, brentuximab vedotin, ado-trastuzumab emtansine, or blinatumomab.

Embodiment 50: The engineered VLP of any one of the embodiments 43-49, wherein the additional therapeutic agent comprises, or consists essentially of, or yet further consists of, a first-line therapy.

Embodiment 51: The engineered VLP of any one of the embodiments 43-49, wherein the additional therapeutic agent comprises, or consists essentially of, or yet further consists of, a second-line therapy, a third-line therapy, a fourth-line therapy, or a fifth-line therapy.

Embodiment 52: The engineered VLP of embodiment 43, wherein the additional therapeutic agent comprises, or consists essentially of, or yet further consists of, an antibiotic.

Embodiment 53: The engineered VLP of embodiment 43, wherein the additional therapeutic agent comprises, or consists essentially of, or yet further consists of, a corticosteroid, a calcineurin inhibitor, a mTOR inhibitor, an EVIDH inhibitor, a biologic, or a monoclonal antibody.

Embodiment 54: A composition comprising, or consisting essentially of, or yet further consisting of, an engineered VLP of embodiments 1-53 and a carrier, optionally a pharmaceutically acceptable carrier.

Embodiment 55: The composition of embodiment 54, wherein the composition is formulated for in vitro or in vivo use, optionally systemic administration.

Embodiment 56: The composition of embodiment 54, wherein the composition is formulated for local administration.

Embodiment 57: The composition of any one of the embodiments 54-56, wherein the composition is formulated for parenteral administration.

Embodiment 58: The composition of any one of the embodiments 54-57, wherein the composition is formulated for intravenous, subcutaneous, intramuscular, intracerebral, intranasal, intra-arterial, intra-articular, intradermal, intravitreal, intraosseous infusion, intraperitoneal, or intrathecal administration.

Embodiment 59: A lyophilized formulation comprising, or consisting essentially of, or yet further consisting of, a composition of embodiments 54-58.

Embodiment 60: A method of treating a disease or condition or inducing an immune response in a subject in need thereof, comprising, or consisting essentially of, or yet further consisting of:

administering to the subject an engineered VLP of embodiments 1-53 or a composition of embodiments 54-58.

Embodiment 61: The method of embodiment 60, wherein the disease or condition is a cancer.

Embodiment 62: The method of embodiment 61, wherein the cancer is a solid tumor.

Embodiment 63: The method of embodiment 62, wherein the solid tumor is bladder cancer, bone cancer, brain cancer, breast cancer, colorectal cancer, colon cancer, esophageal cancer, eye cancer, head and neck cancer, kidney cancer, lung cancer, melanoma, ovarian cancer, pancreatic cancer, prostate cancer, or stomach cancer.

Embodiment 64: The method of embodiment 62, wherein the solid tumor is a colon cancer.

Embodiment 65: The method of embodiment 62, wherein the solid tumor is pancreatic cancer.

Embodiment 66: The method of embodiment 62, wherein the solid tumor is melanoma.

Embodiment 67: The method of embodiment 61, wherein the cancer is a hematologic malignancy.

Embodiment 68: The method of embodiment 67, wherein the hematologic malignancy is a lymphoma or leukemia.

Embodiment 69: The method of embodiment 67, wherein the hematologic malignancy is a B-cell lymphoma.

Embodiment 70: The method of embodiment 67, wherein the hematologic malignancy is a T-cell lymphoma.

Embodiment 71: The method of embodiment 67, wherein the hematologic malignancy is a Hodgkin's lymphoma.

Embodiment 72: The method of embodiment 67, wherein the hematologic malignancy is a non-Hodgkin's lymphoma.

Embodiment 73: The method of any one of the embodiments 61-72, wherein the cancer is a metastatic cancer.

Embodiment 74: The method of any one of the embodiments 61-72, wherein the cancer is a relapsed or refractory cancer.

Embodiment 75: The method of embodiment 60, wherein the disease or condition is an inflammatory condition.

Embodiment 76: The method of embodiment 60, wherein the disease or condition is an autoimmune disease.

Embodiment 77: The method of embodiment 60, wherein the disease or condition is an allergy, optionally an allergic asthma or allergic rhinosinusitis.

Embodiment 78: The method of embodiment 60, wherein the disease or condition is asthma.

Embodiment 79: The method of embodiment 60, wherein the disease or condition is a pathogenic infection.

Embodiment 80: The method of embodiment 79, wherein the pathogen is a virus.

Embodiment 81: The method of embodiment 80, wherein the virus is human immunodeficiency virus (HIV).

Embodiment 82: The method of embodiment 80, wherein the virus is a Hepatitis virus, optionally a Hepatitis B virus or a Hepatitis C virus.

Embodiment 83: The method of embodiment 79, wherein the pathogen is a bacterium, protozoan, helminth, prion, or fungus.

Embodiment 84: The method of embodiment 79, wherein the pathogen is *Vibrio parahaemolyticus*.

Embodiment 85: The method of embodiment 79, wherein the pathogen is rock bream iridovirus, *Edwardsiella tarda*, or *Vibrio vurificus*.

Embodiment 86: The method of any one of the embodiments 60-85, wherein the VLP comprise, or consists essentially of, or yet further consists of, s a surface polypeptide that preferentially homes to a TME.

Embodiment 87: The method of any one of the embodiments 60-86, wherein the VLP targets a TAM.

Embodiment 88: The method of any one of the embodiments 60-87, wherein the VLP modulates, impedes, or inhibits a tumor growth.

Embodiment 89: The method of any one of the embodiments 60-88, wherein the VLP modulates activation of phagocytosis in the immune cell.

Embodiment 90: The method of embodiment 89, wherein the immune cell is the macrophage.

Embodiment 91: The method of any one of the embodiments 60-90, wherein the VLP modulates polarization of the macrophage toward a M1 phenotype.

Embodiment 92: The method of any one of the embodiments 60-91, wherein the VLP decreases the macrophage toward a M2 polarization.

Embodiment 93: The method of any one of the embodiments 60-92, wherein the VLP promotes accumulation of tumor-infiltrating lymphocytes in the TME.

Embodiment 94: The method of any one of the embodiments 60-93, wherein the VLP modulates secretion of a cytokine from the immune cell, optionally the macrophage, thereby to induce an immunostimulation.

Embodiment 95: The method of embodiment 94, wherein the cytokine is a pro-inflammatory cytokine.

Embodiment 96: The method of embodiment 94 or 95, wherein the cytokine is TNFα, IFNγ, IL-1, IL-12, IL-18, or GM-CSF.

Embodiment 97: The method of embodiment 60, further comprising, or consisting essentially of, or yet further consisting of, administering an additional therapeutic agent to the subject.

Embodiment 98: The method of embodiment 97, wherein the additional therapeutic agent is an agent for a cancer therapy.

Embodiment 99: The method of embodiment 98, wherein the additional therapeutic agent comprise, or consists essentially of, or yet further consists of, s chemotherapeutic agent, an immunotherapeutic agent, a targeted therapy, radiation therapy, or a combination thereof.

Embodiment 100: The method of embodiment 98, wherein the additional therapeutic agent comprises, or consists essentially of, or yet further consists of, a cancer immunotherapeutic agent.

Embodiment 101: The method of any one of the embodiments 98-100, wherein the additional therapeutic agent comprises, or consists essentially of, or yet further consists of, a checkpoint inhibitor.

Embodiment 102: The method of any one of the embodiments 98-101, wherein the additional therapeutic agent comprises, or consists essentially of, or yet further consists of, pembrolizumab, nivolumab, tremelimumab, or ipilimumab.

Embodiment 103: The method of any one of the embodiments 98-101, wherein the additional therapeutic agent comprises, or consists essentially of, or yet further consists of, alemtuzumab, trastuzumab, ibritumomab tiuxetan, brentuximab vedotin, ado-trastuzumab emtansine, or blinatumomab.

Embodiment 104: The method of any one of the embodiments 98-103, wherein the additional therapeutic agent comprises, or consists essentially of, or yet further consists of, a first-line therapy.

Embodiment 105: The method of any one of the embodiments 98-103, wherein the additional therapeutic agent comprises, or consists essentially of, or yet further consists of, a second-line therapy, a third-line therapy, a fourth-line therapy, or a fifth-line therapy.

Embodiment 106: The method of embodiment 97, wherein the additional therapeutic agent comprise, or consists essentially of, or yet further consists of, s an antibiotic.

Embodiment 107: The method of embodiment 97, wherein the additional therapeutic agent comprises, or consists essentially of, or yet further consists of, a corticosteroid, a calcineurin inhibitor, a mTOR inhibitor, an EVIDH inhibitor, a biologic, or a monoclonal antibody.

Embodiment 108: The method of any one of the embodiments 60-107, wherein the VLP is a vaccine adjuvant.

Embodiment 109: The method of any one of the embodiments 60-108, wherein the VLP and the additional therapeutic agent are administered simultaneously.

Embodiment 110: The method of any one of the embodiments 60-108, wherein the VLP and the additional therapeutic agent are administered sequentially.

Embodiment 111: The method of embodiment 110, wherein the VLP is administered to the subject prior to administration of the additional therapeutic agent.

Embodiment 112: The method of embodiment 110, wherein the VLP is administered to the subject after administration of the additional therapeutic agent.

Embodiment 113: The method of any one of the embodiments 60-112, wherein the VLP is administered weekly.

Embodiment 114: The method of any one of the embodiments 60-113, further comprising, or consisting essentially of, or yet further consisting of, diagnosing the subject of having the disease or condition prior to administering the engineered VLP of embodiments 1-53 or the composition of embodiments 54-58.

Embodiment 115: The method of any one of the embodiments 60-114, further comprising, or consisting essentially of, or yet further consisting of, monitoring the subject for a progression of the disease or condition during a treatment course comprising, or consisting essentially of, or yet further consisting of, the engineered VLP of embodiments 1-53 or the composition of embodiments 54-58.

Embodiment 116: The method of any one of the embodiments 60-113, further comprising, or consisting essentially of, or yet further consisting of, monitoring the subject for development of an immune response after administration of the engineered VLP of embodiments 1-53 or the composition of embodiments 54-58.

Embodiment 117: A method of modulating phagocytosis in a target cell, comprising, or consisting essentially of, or yet further consisting of:

- contacting a plurality of cells comprising, or consisting essentially of, or yet further consisting of, a macrophage with an engineered VLP of embodiments 1-53 or a composition of embodiments 54-58 for a first time sufficient to activate phagocytic activity of the macrophage; and
- contacting the activated macrophage with the target cell for a second time sufficient to induce phagocytosis of the target cell.

Embodiment 118: The method of embodiment 117, wherein the macrophage has a M1 phenotype.

Embodiment 119: The method of embodiment 117, wherein the plurality of cells are located in a tumor microenvironment (TME).

Embodiment 120: The method of embodiment 117, wherein the plurality of cells comprise, or consists essentially of, or yet further consists of, antigen-presenting cells (APCs).

Embodiment 121: The method of embodiment 120, wherein the APCs further comprises, or consists essentially of, or yet further consists of, dendritic cells, B cells, or a combination thereof.

Embodiment 122: The method of embodiment 117, wherein the target cell is a cancer cell.

Embodiment 123: The method of embodiment 117, wherein the target cell is a cell infected by a pathogen.

Embodiment 124: A method of modulating M1 macrophage polarization, comprising, or consisting essentially of, or yet further consisting of:

- contacting a plurality of antigen presenting cells (APCs) comprising, or consisting essentially of, or yet further consisting of, at least one macrophage with an engineered VLP of embodiments 1-53 or a composition of embodiments 54-58 for a time sufficient to induce secretion of a plurality of cytokines by the plurality of APCs, whereby the secretion of the plurality of cytokines modulate M1 activation of the macrophage.

Embodiment 125: The method of embodiment 124, wherein the APCs are located within a tumor microenvironment.

Embodiment 126: The method of embodiment 124, wherein the plurality of cytokines comprise, or consists essentially of, or yet further consists of, IFNγ, TNFα, or a combination thereof.

Embodiment 127: The method of embodiment 124, wherein the VLP decreases M2 activation of the macrophage.

Embodiment 128: The method of embodiment 124, wherein the APCs further comprise, or consists essentially of, or yet further consists of, s dendritic cells, B cells, or a combination thereof.

Embodiment 129: The method of any one of the embodiments 117-128, wherein the method is an in vitro method.

Embodiment 130: The method of any one of the embodiments 117-128, wherein the method is an in vivo method.

Embodiment 131: The method of any one of the embodiments 117-128, wherein the method is an ex vivo method.

Embodiment 132: The method of any one of the embodiments 60-131, wherein the subject is a human.

Embodiment 133: A kit comprising, or consisting essentially of, or yet further consisting of, an engineered VLP of embodiments 1-53 or a composition of embodiments 54-58, and optionally instructions for use.

REFERENCES

1. Wooldridge, J. E.; Ballas, Z.; Krieg, A. M.; Weiner, G. J., Immunostimulatory oligodeoxynucleotides containing CpG motifs enhance the efficacy of monoclonal antibody therapy of lymphoma. *Blood* 1997, 89 (8), 2994-8.
2. Krieg, A. M., CpG motifs in bacterial DNA and their immune effects. *Annu Rev Immunol* 2002, 20, 709-60.
3. Krieg, A. M.; Yi, A. K.; Matson, S.; Waldschmidt, T. J.; Bishop, G. A.; Teasdale, R.; Koretzky, G. A.; Klinman, D. M., CpG motifs in bacterial DNA trigger direct B-cell activation. *Nature* 1995, 374 (6522), 546-9.
4. Krieg, A. M., Toll-like receptor 9 (TLR9) agonists in the treatment of cancer. *Oncogene* 2008, 27 (2), 161-7.
5. Krieg, A. M., Therapeutic potential of Toll-like receptor 9 activation. *Nat Rev Drug Discov* 2006, 5 (6), 471-84.
6. Verthelyi, D.; Gursel, M.; Kenney, R. T.; Lifson, J. D.; Liu, S.; Mican, J.; Klinman, D. M., CpG oligodeoxynucleotides protect normal and SIV-infected macaques from *Leishmania* infection. *J Immunol* 2003, 170 (9), 4717-23.
7. Hanagata, N., CpG oligodeoxynucleotide nanomedicines for the prophylaxis or treatment of cancers, infectious diseases, and allergies. *Int J Nanomedicine* 2017, 12, 515-531.
8. Jahrsdorfer, B.; Weiner, G. J., CpG oligodeoxynucleotides as immunotherapy in cancer. *Update Cancer Ther* 2008, 3 (1), 27-32.
9. Adamus, T.; Kortylewski, M., The revival of CpG oligonucleotide-based cancer immunotherapies. *Contemp Oncol* (*Pozn*) 2018, 22 (1A), 56-60.
10. Krieg, A. M., Development of TLR9 agonists for cancer therapy. *J Clin Invest* 2007, 117 (5), 1184-94.
11. Valmori, D.; Souleimanian, N. E.; Tosello, V.; Bhardwaj, N.; Adams, S.; O'Neill, D.; Pavlick, A.; Escalon, J. B.; Cruz, C. M.; Angiulli, A.; Angiulli, F.; Mears, G.; Vogel, S. M.; Pan, L.; Jungbluth, A. A.; Hoffmann, E. W.; Venhaus, R.; Ritter, G.; Old, L. J.; Ayyoub, M., Vaccination with NY-ESO-1 protein and CpG in Montanide induces integrated antibody/Th1 responses and CD8 T cells through cross-priming. *Proc Natl Acad Sci USA* 2007, 104 (21), 8947-52.
12. Molenkamp, B. G.; van Leeuwen, P. A.; Meijer, S.; Sluijter, B. J.; Wijnands, P. G.; Baars, A.; van den Eertwegh, A. J.; Scheper, R. J.; de Gruijl, T. D., Intradermal CpG-B activates both plasmacytoid and myeloid dendritic cells in the sentinel lymph node of melanoma patients. *Clin Cancer Res* 2007, 13 (10), 2961-9.
13. Smith, D. A.; Conkling, P.; Richards, D. A.; Nemunaitis, J. J.; Boyd, T. E.; Mita, A. C.; de La Bourdonnaye, G.; Wages, D.; Bexon, A. S., Antitumor activity and safety of combination therapy with the Toll-like receptor 9 agonist IMO-2055, erlotinib, and bevacizumab in advanced or metastatic non-small cell lung cancer patients who have progressed following chemotherapy. *Cancer Immunol Immunother* 2014, 63 (8), 787-96.
14. Chan, E.; Kwak, E. L.; Hwang, J.; Heiskala, M.; de La Bourdonnaye, G.; Mita, M., Open-label phase 1b study of FOLFIRI plus cetuximab plus IMO-2055 in patients with colorectal cancer who have progressed following chemotherapy for advanced or metastatic disease. *Cancer Chemother Pharmacol* 2015, 75 (4), 701-9.
15. Krieg, A. M., CpG still rocks! Update on an accidental drug. *Nucleic Acid Ther* 2012, 22 (2), 77-89.
16. Mutwiri, G. K.; Nichani, A. K.; Babiuk, S.; Babiuk, L. A., Strategies for enhancing the immunostimulatory effects of CpG oligodeoxynucleotides. *J Control Release* 2004, 97 (1), 1-17.
17. Sands, H.; Gorey-Feret, L. J.; Cocuzza, A. J.; Hobbs, F. W.; Chidester, D.; Trainor, G. L., Biodistribution and metabolism of internally 3H-labeled oligonucleotides. I. Comparison of a phosphodiester and a phosphorothioate. *Mol Pharmacol* 1994, 45 (5), 932-43.
18. Liu, H.; Kwong, B.; Irvine, D. J., Membrane anchored immunostimulatory oligonucleotides for in vivo cell modification and localized immunotherapy. *Angew Chem Int Ed Engl* 2011, 50 (31), 7052-5.
19. Liu, H.; Moynihan, K. D.; Zheng, Y.; Szeto, G. L.; Li, A. V.; Huang, B.; Van Egeren, D. S.; Park, C.; Irvine, D. J., Structure-based programming of lymph-node targeting in molecular vaccines. *Nature* 2014, 507 (7493), 519-22.
20. Dalpke, A. H.; Zimmermann, S.; Albrecht, I.; Heeg, K., Phosphodiester CpG oligonucleotides as adjuvants: polyguanosine runs enhance cellular uptake and improve immunostimulative activity of phosphodiester CpG oligonucleotides in vitro and in vivo. *Immunology* 2002, 106 (1), 102-12.
21. Wei, M.; Chen, N.; Li, J.; Yin, M.; Liang, L.; He, Y.; Song, H.; Fan, C.; Huang, Q., Polyvalent immunostimulatory nanoagents with self-assembled CpG oligonucleotide-conjugated gold nanoparticles. *Angew Chem Int Ed Engl* 2012, 51 (5), 1202-6.
22. Lin, A. Y.; Almeida, J. P.; Bear, A.; Liu, N.; Luo, L.; Foster, A. E.; Drezek, R. A., Gold nanoparticle delivery of modified CpG stimulates macrophages and inhibits tumor growth for enhanced immunotherapy. *PLoS One* 2013, 8 (5), e63550.
23. Li, J.; Pei, H.; Zhu, B.; Liang, L.; Wei, M.; He, Y.; Chen, N.; Li, D.; Huang, Q.; Fan, C., Self-assembled multivalent DNA nanostructures for noninvasive intracellular delivery of immunostimulatory CpG oligonucleotides. *ACS Nano* 2011, 5 (11), 8783-9.
24. Nishikawa, M.; Ogawa, K.; Umeki, Y.; Mohri, K.; Kawasaki, Y.; Watanabe, H.; Takahashi, N.; Kusuki, E.; Takahashi, R.; Takahashi, Y.; Takakura, Y., Injectable, selfgelling, biodegradable, and immunomodulatory DNA hydrogel for antigen delivery. *J Control Release* 2014, 180, 25-32.
25. Zhang, L.; Zhu, G.; Mei, L.; Wu, C.; Qiu, L.; Cui, C.; Liu, Y.; Teng, I. T.; Tan, W., Self-Assembled DNA Immunonanoflowers as Multivalent CpG Nanoagents. *ACS Appl Mater Interfaces* 2015, 7 (43), 24069-74.
26. Rohovie, M. J.; Nagasawa, M.; Swartz, J. R., Virus-like particles: Next-generation nanoparticles for targeted therapeutic delivery. *Bioeng Transl Med* 2017, 2 (1), 43-57.
27. Storni, T.; Ruedl, C.; Schwarz, K.; Schwendener, R. A.; Renner, W. A.; Bachmann, M. F., Nonmethylated CG motifs packaged into virus-like particles induce protective cytotoxic T cell responses in the absence of systemic side effects. *J Immunol* 2004, 172 (3), 1777-85.
28. Wen, A. M.; Steinmetz, N. F., Design of virus-based nanomaterials for medicine, biotechnology, and energy. *Chem Soc Rev* 2016, 45 (15), 4074-126.

29. Lizotte, P. H.; Wen, A. M.; Sheen, M. R.; Fields, J.; Rojanasopondist, P.; Steinmetz, N. F.; Fiering, S., In situ vaccination with cowpea mosaic virus nanoparticles suppresses metastatic cancer. *Nat Nanotechnol* 2016, 11 (3), 295-303.
30. Wang, C.; Steinmetz, N. F., CD47 Blockade and Cowpea Mosaic Virus Nanoparticle In Situ Vaccination Triggers Phagocytosis and Tumor Killing. *Adv Healthc Mater* 2019, 8 (8), e1801288.
31. Wang, C.; Beiss, V.; Steinmetz, N. F., Cowpea mosaic virus nanoparticles and empty virus-like particles show distinct but overlapping immunostimulatory properties. *J Virol* 2019.
32. Cai, H.; Wang, C.; Shukla, S.; Steinmetz, N. F., Cowpea Mosaic Virus Immunotherapy Combined with Cyclophosphamide Reduces Breast Cancer Tumor Burden and Inhibits Lung Metastasis. *Adv Sci (Weinh)* 2019, 6 (16), 1802281.
33. Sokullu, E.; Soleymani Abyaneh, H.; Gauthier, M. A., Plant/Bacterial Virus-Based Drug Discovery, Drug Delivery, and Therapeutics. *Pharmaceutics* 2019, 11 (5).
34. Azizgolshani, O.; Garmann, R. F.; Cadena-Nava, R.; Knobler, C. M.; Gelbart, W. M., Reconstituted plant viral capsids can release genes to mammalian cells. *Virology* 2013, 441 (1), 12-7.
35. Lam, P.; Steinmetz, N. F., Delivery of siRNA therapeutics using cowpea chlorotic mottle virus-like particles. *Biomater Sci* 2019, 7 (8), 3138-3142.
36. Liu, M.; O'Connor, R. S.; Trefely, S.; Graham, K.; Snyder, N. W.; Beatty, G. L., Metabolic rewiring of macrophages by CpG potentiates clearance of cancer cells and overcomes tumor-expressed CD47-mediated 'don't-eat-me' signal. *Nat Immunol* 2019, 20 (3), 265-275.
37. Lavelle, L.; Michel, J. P.; Gingery, M., The disassembly, reassembly and stability of CCMV protein capsids. *J Virol Methods* 2007, 146 (1-2), 311-6.
38. Comas-Garcia, M.; Garmann, R. F.; Singaram, S. W.; Ben-Shaul, A.; Knobler, C. M.; Gelbart, W. M., Characterization of Viral Capsid Protein Self-Assembly around Short Single-Stranded RNA. *J Phys Chem B* 2014, 118 (27), 7510-7519.
39. Gao, M.; Ha, T.; Zhang, X.; Wang, X.; Liu, L.; Kalbfleisch, J.; Singh, K.; Williams, D.; Li, C., The Toll-like receptor 9 ligand, CpG oligodeoxynucleotide, attenuates cardiac dysfunction in polymicrobial sepsis, involving activation of both phosphoinositide 3 kinase/Akt and extracellular-signal-related kinase signaling. *J Infect Dis* 2013, 207 (9), 1471-9.
40. Mantovani, A.; Allavena, P.; Sica, A.; Balkwill, F., Cancer-related inflammation. *Nature* 2008, 454 (7203), 436-44.
41. Mantovani, A.; Marchesi, F.; Malesci, A.; Laghi, L.; Allavena, P., Tumourassociated macrophages as treatment targets in oncology. *Nat Rev Clin Oncol* 2017, 14 (7), 399-416.
42. Beatty, G. L.; Chiorean, E. G.; Fishman, M. P.; Saboury, B.; Teitelbaum, U. R.; Sun, W.; Huhn, R. D.; Song, W.; Li, D.; Sharp, L. L.; Torigian, D. A.; O'Dwyer, P. J.; Vonderheide, R. H., CD40 agonists alter tumor stroma and show efficacy against pancreatic carcinoma in mice and humans. *Science* 2011, 331 (6024), 1612-6.
43. Rolny, C.; Mazzone, M.; Tugues, S.; Laoui, D.; Johansson, I.; Coulon, C.; Squadrito, M. L.; Segura, I.; Li, X.; Knevels, E.; Costa, S.; Vinckier, S.; Dresselaer, T.; Akerud, P.; De Mol, M.; Salomaki, H.; Phillipson, M.; Wyns, S.; Larsson, E.; Buysschaert, I.; Botling, J.; Himmelreich, U.; Van Ginderachter, J. A.; De Palma, M.; Dewerchin, M.; Claesson-Welsh, L.; Carmeliet, P., HRG inhibits tumor growth and metastasis by inducing macrophage polarization and vessel normalization through downregulation of PlGF. *Cancer Cell* 2011, 19 (1), 31-44.
44. Chanmee, T.; Ontong, P.; Konno, K.; Itano, N., Tumor-associated macrophages as major players in the tumor microenvironment. *Cancers (Basel)* 2014, 6 (3), 1670-90.
45. Ali, A.; Roossinck, M. J., Rapid and efficient purification of Cowpea chlorotic mottle virus by sucrose cushion ultracentrifugation. *J Virol Methods* 2007, 141 (1), 84-6.

What is claimed is:

1. An engineered virus-like particle (VLP) derived from Cowpea chlorotic mottle virus (CCMV) comprising ODN1826 (SEQ ID NO: 4) encapsulated within the VLP, wherein the VLP increases uptake of the ODN1826 by a tumor-associated macrophage (TAM) compared to uptake of free ODN1826 by the TAM, and does not increase uptake of the ODN1826 by tumor cells.

2. The engineered VLP of claim 1, wherein the VLP comprises an extracellular or transmembrane polypeptide that specifically binds to a receptor expressed on an immune cell selected from an antigen presenting cell, a macrophage, a B cell, a dendritic cell, or a nature killer (NK) cell.

3. The engineered VLP of claim 2, wherein the macrophage is a tumor-associated macrophage (TAM).

4. The engineered VLP of claim 1, wherein the VLP increases uptake of the ODN in a macrophage, optionally a TAM, compared to uptake of an ODN by the macrophage, optionally the TAM, not encapsulated by the engineered VLP.

5. The engineered VLP of claim 1, wherein the VLP induces activation of phagocytosis in an immune cell, optionally a macrophage.

6. The engineered VLP of claim 1, wherein the VLP modulates polarization of a macrophage toward a M1 phenotype.

7. The engineered VLP of claim 1, wherein the VLP induces secretion of a cytokine from an immune cell, optionally a macrophage, thereby to induce an immunostimulation.

8. The engineered VLP of claim 1, further comprising an additional therapeutic agent encapsulated within the VLP, optionally an agent for cancer therapy.

9. A composition comprising the engineered VLP of claim 1 and a pharmaceutically acceptable carrier.

10. A method of treating a cancer or inducing an immune response in a subject in need thereof, comprising:

administering to the subject the engineered VLP of claim 1.

11. A method of inducing phagocytosis of a target cell, comprising:

firstly, contacting a plurality of cells comprising a macrophage with the engineered VLP of claim 1 for a time sufficient to activate phagocytic activity of the macrophage; and secondly, contacting the macrophage having activated phagocytic activity with the target cell for a time sufficient to induce phagocytosis of the target cell by the macrophage.

12. A method of modulating macrophage polarization, comprising:

contacting a plurality of antigen presenting cells (APCs) comprising at least one macrophage with the engineered VLP of claim 1 for a time sufficient to induce secretion of a plurality of cytokines by the plurality of APCs, whereby the secretion of the plurality of cytokines modulates polarization of the macrophage toward a M1 phenotype.

13. A kit comprising the engineered VLP of claim 1, and optionally instructions for use.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ggggtcaacg ttgagggggg                                                 20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gggggacgat cgtcgggggg                                                 20


<210> SEQ ID NO 3
```

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ggggacgacg tcgtgggggg g 21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
tccatgacgt tcctgacgtt 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tccatgacgt tcctgatgct 20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
tcgtcgtttt gtcgttttgt cgtt 24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tcgtcgttgt cgttttgtcg tt 22

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
tcgcgtgcgt tttgtcgttt tgacgtt 27

<210> SEQ ID NO 9
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

tcgacgttcg tcgttcgtcg ttc                                              23


<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

tcgcgacgtt cgcccgacgt tcggta                                           26


<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

tcgtcgtttt cggcgcgcgc cg                                               22


<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

tcgtcgtcgt tcgaacgacg ttgat                                            25


<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

tcgcgaacgt tcgccgcgtt cgaacgcgg                                        29


<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

tcgtcgtttt cgcgcgcgcg ccg                                              23


<210> SEQ ID NO 15
<211> LENGTH: 23
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 15
tcgtcgacga tcggcgcgcg ccg 23

<210> SEQ ID NO 16
<211> LENGTH: 190
<212> TYPE: PRT
<213> ORGANISM: Cowpea chlorotic mottle virus

<400> SEQUENCE: 16

```
Met Ser Thr Val Gly Thr Gly Lys Leu Thr Arg Ala Gln Arg Arg Ala
1               5                   10                  15

Ala Ala Arg Lys Asn Lys Arg Asn Thr Arg Val Val Gln Pro Val Ile
            20                  25                  30

Val Glu Pro Ile Ala Ser Gly Gln Gly Lys Ala Ile Lys Ala Trp Thr
        35                  40                  45

Gly Tyr Ser Val Ser Lys Trp Thr Ala Ser Cys Ala Ala Ala Glu Ala
    50                  55                  60

Lys Val Thr Ser Ala Ile Thr Ile Ser Leu Pro Asn Glu Leu Ser Ser
65                  70                  75                  80

Glu Arg Asn Lys Gln Leu Lys Val Gly Arg Val Leu Leu Trp Leu Gly
                85                  90                  95

Leu Leu Pro Ser Val Ser Gly Thr Val Lys Ser Cys Val Thr Glu Thr
            100                 105                 110

Gln Thr Thr Ala Ala Ala Ser Phe Gln Val Ala Leu Ala Val Ala Asp
        115                 120                 125

Asn Ser Lys Asp Val Val Ala Ala Met Tyr Pro Glu Ala Phe Lys Gly
    130                 135                 140

Ile Thr Leu Glu Gln Leu Thr Ala Asp Leu Thr Ile Tyr Leu Tyr Ser
145                 150                 155                 160

Ser Ala Ala Leu Thr Glu Gly Asp Val Ile Val His Leu Glu Val Glu
                165                 170                 175

His Val Arg Pro Thr Phe Asp Asp Ser Phe Thr Pro Val Tyr
            180                 185                 190
```

<210> SEQ ID NO 17
<211> LENGTH: 374
<212> TYPE: PRT
<213> ORGANISM: Cowpea mosaic virus

<400> SEQUENCE: 17

```
Met Glu Gln Asn Leu Phe Ala Leu Ser Leu Asp Asp Thr Ser Ser Val
1               5                   10                  15

Arg Gly Ser Leu Leu Asp Thr Lys Phe Ala Gln Thr Arg Val Leu Leu
            20                  25                  30

Ser Lys Ala Met Ala Gly Gly Asp Val Leu Leu Asp Glu Tyr Leu Tyr
        35                  40                  45

Asp Val Val Asn Gly Gln Asp Phe Arg Ala Thr Val Ala Phe Leu Arg
    50                  55                  60

Thr His Val Ile Thr Gly Lys Ile Lys Val Thr Ala Thr Thr Asn Ile
65                  70                  75                  80

Ser Asp Asn Ser Gly Cys Cys Leu Met Leu Ala Ile Asn Ser Gly Val
                85                  90                  95
```

```
Arg Gly Lys Tyr Ser Thr Asp Val Tyr Thr Ile Cys Ser Gln Asp Ser
            100                 105                 110

Met Thr Trp Asn Pro Gly Cys Lys Lys Asn Phe Ser Phe Thr Phe Asn
        115                 120                 125

Pro Asn Pro Cys Gly Asp Ser Trp Ser Ala Glu Met Ile Ser Arg Ser
    130                 135                 140

Arg Val Arg Met Thr Val Ile Cys Val Ser Gly Trp Thr Leu Ser Pro
145                 150                 155                 160

Thr Thr Asp Val Ile Ala Lys Leu Asp Trp Ser Ile Val Asn Glu Lys
                165                 170                 175

Cys Glu Pro Thr Ile Tyr His Leu Ala Asp Cys Gln Asn Trp Leu Pro
            180                 185                 190

Leu Asn Arg Trp Met Gly Lys Leu Thr Phe Pro Gln Gly Val Thr Ser
        195                 200                 205

Glu Val Arg Arg Met Pro Leu Ser Ile Gly Gly Gly Ala Gly Ala Thr
    210                 215                 220

Gln Ala Phe Leu Ala Asn Met Pro Asn Ser Trp Ile Ser Met Trp Arg
225                 230                 235                 240

Tyr Phe Arg Gly Glu Leu His Phe Glu Val Thr Lys Met Ser Ser Pro
                245                 250                 255

Tyr Ile Lys Ala Thr Val Thr Phe Leu Ile Ala Phe Gly Asn Leu Ser
            260                 265                 270

Asp Ala Phe Gly Phe Tyr Glu Ser Phe Pro His Arg Ile Val Gln Phe
        275                 280                 285

Ala Glu Val Glu Glu Lys Cys Thr Leu Val Phe Ser Gln Gln Glu Phe
    290                 295                 300

Val Thr Ala Trp Ser Thr Gln Val Asn Pro Arg Thr Thr Leu Glu Ala
305                 310                 315                 320

Asp Gly Cys Pro Tyr Leu Tyr Ala Ile Ile His Asp Ser Thr Thr Gly
                325                 330                 335

Thr Ile Ser Gly Asp Phe Asn Leu Gly Val Lys Leu Val Gly Ile Lys
            340                 345                 350

Asp Phe Cys Gly Ile Gly Ser Asn Pro Gly Ile Asp Gly Ser Arg Leu
        355                 360                 365

Leu Gly Ala Ile Ala Gln
    370


<210> SEQ ID NO 18
<211> LENGTH: 189
<212> TYPE: PRT
<213> ORGANISM: Cowpea mosaic virus

<400> SEQUENCE: 18

Gly Pro Val Cys Ala Glu Ala Ser Asp Val Tyr Ser Pro Cys Met Ile
1               5                   10                  15

Ala Ser Thr Pro Pro Ala Pro Phe Ser Asp Val Thr Ala Val Thr Phe
            20                  25                  30

Asp Leu Ile Asn Gly Lys Ile Thr Pro Val Gly Asp Asp Asn Trp Asn
        35                  40                  45

Thr His Ile Tyr Asn Pro Pro Ile Met Asn Val Leu Arg Thr Ala Ala
    50                  55                  60

Trp Lys Ser Gly Thr Ile His Val Gln Leu Asn Val Arg Gly Ala Gly
65                  70                  75                  80

Val Lys Arg Ala Asp Trp Asp Gly Gln Val Phe Val Tyr Leu Arg Gln
                85                  90                  95
```

Ser Met Asn Pro Glu Ser Tyr Asp Ala Arg Thr Phe Val Ile Ser Gln
100 105 110

Pro Gly Ser Ala Met Leu Asn Phe Ser Phe Asp Ile Ile Gly Pro Asn
115 120 125

Ser Gly Phe Glu Phe Ala Glu Ser Pro Trp Ala Asn Gln Thr Thr Trp
130 135 140

Tyr Leu Glu Cys Val Ala Thr Asn Pro Arg Gln Ile Gln Gln Phe Glu
145 150 155 160

Val Asn Met Arg Phe Asp Pro Asn Phe Arg Val Ala Gly Asn Ile Leu
165 170 175

Met Pro Pro Phe Pro Leu Ser Thr Glu Thr Pro Pro Leu
180 185

<210> SEQ ID NO 19
<211> LENGTH: 188
<212> TYPE: PRT
<213> ORGANISM: Physalis mottle virus

<400> SEQUENCE: 19

Met Asp Ser Ser Glu Val Val Lys Val Lys Gln Ala Ser Ile Pro Ala
1 5 10 15

Pro Gly Ser Ile Leu Ser Gln Pro Asn Thr Glu Gln Ser Pro Ala Ile
20 25 30

Val Leu Pro Phe Gln Phe Glu Ala Thr Thr Phe Gly Thr Ala Glu Thr
35 40 45

Ala Ala Gln Val Ser Leu Gln Thr Ala Asp Pro Ile Thr Lys Leu Thr
50 55 60

Ala Pro Tyr Arg His Ala Gln Ile Val Glu Cys Lys Ala Ile Leu Thr
65 70 75 80

Pro Thr Asp Leu Ala Val Ser Asn Pro Leu Thr Val Tyr Leu Ala Trp
85 90 95

Val Pro Ala Asn Ser Pro Ala Thr Pro Thr Gln Ile Leu Arg Val Tyr
100 105 110

Gly Gly Gln Ser Phe Val Leu Gly Gly Ala Ile Ser Ala Ala Lys Thr
115 120 125

Ile Glu Val Pro Leu Asn Leu Asp Ser Val Asn Arg Met Leu Lys Asp
130 135 140

Ser Val Thr Tyr Thr Asp Thr Pro Lys Leu Leu Ala Tyr Ser Arg Ala
145 150 155 160

Pro Thr Asn Pro Ser Lys Ile Pro Thr Ala Ser Ile Gln Ile Ser Gly
165 170 175

Arg Ile Arg Leu Ser Lys Pro Met Leu Ile Ala Asn
180 185

<210> SEQ ID NO 20
<211> LENGTH: 268
<212> TYPE: PRT
<213> ORGANISM: Sesbania mosaic virus

<400> SEQUENCE: 20

Met Ala Lys Arg Leu Ser Lys Gln Gln Leu Ala Lys Ala Ile Ala Asn
1 5 10 15

Thr Leu Glu Thr Pro Pro Gln Pro Lys Ala Gly Arg Arg Arg Asn Arg
20 25 30

Arg Arg Gln Arg Ser Ala Val Gln Gln Leu Gln Pro Thr Gln Ala Gly
35 40 45

-continued

```
Ile Ser Met Ala Pro Ser Ala Gln Gly Ala Met Val Arg Ile Arg Asn
    50                  55                  60

Pro Ala Val Ser Ser Ser Arg Gly Gly Ile Thr Val Leu Thr His Ser
65                  70                  75                  80

Glu Leu Ser Ala Glu Ile Gly Val Thr Asp Ser Ile Val Val Ser Ser
                85                  90                  95

Glu Leu Val Met Pro Tyr Thr Val Gly Thr Trp Leu Arg Gly Val Ala
            100                 105                 110

Ala Asn Trp Ser Lys Tyr Ser Trp Leu Ser Val Arg Tyr Thr Tyr Ile
        115                 120                 125

Pro Ser Cys Pro Ser Ser Thr Ala Gly Ser Ile His Met Gly Phe Gln
    130                 135                 140

Tyr Asp Met Ala Asp Thr Val Pro Val Ser Val Asn Gln Leu Ser Asn
145                 150                 155                 160

Leu Arg Gly Tyr Val Ser Gly Gln Val Trp Ser Gly Ser Ala Gly Leu
                165                 170                 175

Cys Phe Ile Asn Gly Thr Arg Cys Ser Asp Thr Ser Thr Ala Ile Ser
            180                 185                 190

Thr Thr Leu Asp Val Ser Lys Leu Gly Lys Lys Trp Tyr Pro Tyr Lys
        195                 200                 205

Thr Ser Ala Asp Tyr Ala Thr Ala Val Gly Val Asp Val Asn Ile Ala
    210                 215                 220

Thr Pro Leu Val Pro Ala Arg Leu Val Ile Ala Leu Leu Asp Gly Ser
225                 230                 235                 240

Ser Ser Thr Ala Val Ala Ala Gly Arg Ile Tyr Cys Thr Tyr Thr Ile
                245                 250                 255

Gln Met Ile Glu Pro Thr Ala Ser Ala Leu Asn Asn
            260                 265
```